(12) United States Patent
Christiansen et al.

(10) Patent No.: US 9,556,096 B2
(45) Date of Patent: *Jan. 31, 2017

(54) UNSYMMETRIC BISPHOSPHITE

(71) Applicant: EVONIK DEGUSSA GMBH, Essen (DE)

(72) Inventors: Andrea Christiansen, Rostock (DE); Robert Franke, Marl (DE); Dirk Fridag, Haltern am See (DE); Dieter Hess, Marl (DE); Katrin Marie Dyballa, Recklinghausen (DE); Bernd Hannebauer, Muehlheim (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/435,007

(22) PCT Filed: Sep. 27, 2013

(86) PCT No.: PCT/EP2013/070210
§ 371 (c)(1),
(2) Date: Apr. 10, 2015

(87) PCT Pub. No.: WO2014/056733
PCT Pub. Date: Apr. 17, 2014

(65) Prior Publication Data
US 2015/0290633 A1      Oct. 15, 2015

(30) Foreign Application Priority Data

Oct. 12, 2012   (DE) ..................... 10 2012 218 625
Oct. 12, 2012   (DE) ..................... 10 2012 218 627
Oct. 12, 2012   (DE) ..................... 10 2012 218 629
Oct. 12, 2012   (DE) ..................... 10 2012 218 630

(51) Int. Cl.
| | |
|---|---|
| *C07F 9/53* | (2006.01) |
| *C07C 45/50* | (2006.01) |
| *B01J 31/18* | (2006.01) |
| *C07F 9/6574* | (2006.01) |
| *B01J 31/02* | (2006.01) |
| *B01J 19/24* | (2006.01) |
| *C07C 67/38* | (2006.01) |

(Continued)

(52) U.S. Cl.
CPC .............. *C07C 45/505* (2013.01); *B01J 19/24* (2013.01); *B01J 31/0209* (2013.01); *B01J 31/0237* (2013.01); *B01J 31/0271* (2013.01); *B01J 31/185* (2013.01); *C07C 45/50* (2013.01); *C07C 67/38* (2013.01); *C07F 9/6571* (2013.01); *C07F 9/65746* (2013.01); *C07F 15/0073* (2013.01); *B01J 2219/24* (2013.01); *B01J 2231/321* (2013.01); *B01J 2531/822* (2013.01); *C07F 9/65683* (2013.01); *C07F 9/65685* (2013.01)

(58) Field of Classification Search
USPC ...................................... 568/12, 14
See application file for complete search history.

(56) References Cited

U.S. PATENT DOCUMENTS

| | | | |
|---|---|---|---|
| 4,067,890 A | 1/1978 | Rutledge | |
| 4,668,651 A * | 5/1987 | Billig .................... | B01J 31/185 502/158 |

(Continued)

FOREIGN PATENT DOCUMENTS

| | | |
|---|---|---|
| DE | 25 36 870 A1 | 3/1976 |
| DE | 10 2008 002 187 A1 | 12/2009 |

(Continued)

OTHER PUBLICATIONS

U.S. Appl. No. 14/434,988, filed Apr. 10, 2015, Christiansen, et al.
U.S. Appl. No. 14/434,879, filed Apr. 10, 2015, Christiansen, et al.
U.S. Appl. No. 14/434,827, filed Apr. 10, 2015, Christiansen, et al.
U.S. Appl. No. 14/435,052, filed Apr. 10, 2015, Fridag, et al.
International Search Report issued Jan. 7, 2014 in PCT/EP2013/070210.

*Primary Examiner* — Sudhakar Katakam
*Assistant Examiner* — Pancham Bakshi
(74) *Attorney, Agent, or Firm* — Oblon, McClelland, Maier & Neustadt, L.L.P.

(57) ABSTRACT

An unsymmetric bisphosphite of the formula (1)

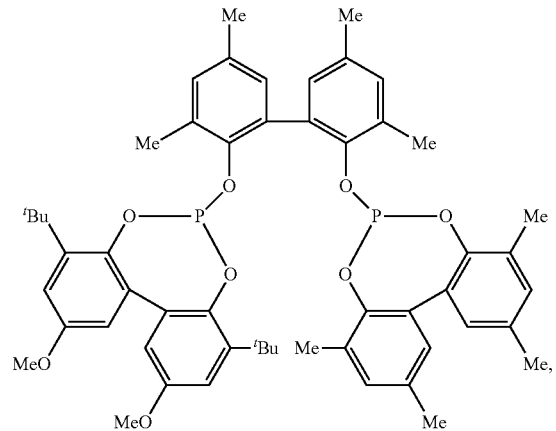

a process for preparation thereof, a reaction thereof with metals to give mixtures containing complexes of the unsymmetric bisphosphite and the metal, and a use thereof as a catalytically active composition in hydroformylation reactions, where the hydroformylation-active composition contains, as well as the complex of metal and unsymmetric bisphosphite, unbound bisphosphite and at least one further component.

18 Claims, 66 Drawing Sheets

(51) Int. Cl.
*C07F 9/6571* (2006.01)
*C07F 15/00* (2006.01)
*C07F 9/6568* (2006.01)

(56) References Cited

U.S. PATENT DOCUMENTS

| | | |
|---|---|---|
| 4,769,498 A | 9/1988 | Billig et al. |
| 5,202,297 A | 4/1993 | Lorz et al. |
| 5,288,918 A | 2/1994 | Maher et al. |
| 5,312,996 A | 5/1994 | Packett |
| 8,461,394 B2 | 6/2013 | Lueken et al. |
| 8,884,070 B2 | 11/2014 | Franke et al. |
| 2003/0195368 A1* | 10/2003 | Rottger et al. .............. 556/13 |
| 2011/0130595 A1 | 6/2011 | Lueken et al. |
| 2015/0018576 A1 | 1/2015 | Baumgarten et al. |

FOREIGN PATENT DOCUMENTS

| | | |
|---|---|---|
| EP | 1 294 731 B1 | 2/2004 |
| EP | 2 003 138 A1 | 12/2008 |
| WO | WO 95/28228 A1 | 10/1995 |
| WO | WO 2014/056735 A1 | 4/2014 |
| WO | WO 2014/056736 A1 | 4/2014 |
| WO | WO 2014/056737 A1 | 4/2014 |

* cited by examiner

| P  | 2.52954  | 0.07247  | 0.34123  |
|----|----------|----------|----------|
| C  | 1.08771  | -1.80868 | 2.94505  |
| C  | 0.69072  | -2.77268 | 0.28859  |
| Rh | 0.72431  | -1.06510 | 1.21707  |
| O  | 0.64091  | -3.83705 | -0.16664 |
| O  | 1.33139  | -2.19921 | 4.01007  |
| P  | -1.37328 | -0.32824 | 0.60927  |
| C  | -3.05546 | -0.28179 | -1.60715 |
| C  | -4.28433 | 0.00927  | -0.93489 |
| C  | -4.86541 | -2.52310 | 4.82271  |
| H  | -4.90132 | -1.66676 | 5.53217  |
| H  | -5.90501 | -2.76457 | 4.50942  |
| H  | -4.47662 | -3.39889 | 5.38740  |
| C  | 4.25101  | -1.58118 | -0.88482 |
| C  | 5.44973  | -1.52370 | -0.12944 |
| C  | 5.90441  | -0.26666 | 0.52336  |
| C  | 5.03709  | 0.56847  | 1.26336  |

Figure 2 - cont.

| | | | |
|---|---|---|---|
| C | 5.49245 | 1.73958 | 1.91201 |
| C | 6.85084 | 2.07626 | 1.78312 |
| H | 7.21575 | 2.99059 | 2.28341 |
| C | 7.75449 | 1.28595 | 1.04041 |
| C | 7.26265 | 0.12203 | 0.42774 |
| H | 7.94569 | -0.50401 | -0.17006 |
| C | 1.48851 | 2.25772 | -0.91537 |
| C | 1.80200 | 2.49264 | -2.27704 |
| C | -1.73794 | -1.08346 | -3.72048 |
| C | -1.99336 | -1.40397 | -5.21278 |
| H | -2.29440 | -0.50421 | -5.79375 |
| H | -1.05173 | -1.78493 | -5.66570 |
| H | -2.76720 | -2.19060 | -5.35282 |
| C | -1.04419 | 2.11637 | 1.77582 |
| C | 0.02443 | 2.76816 | 1.11676 |
| C | 0.26048 | 2.68604 | -0.35777 |
| C | -0.70053 | 3.26137 | -1.21804 |
| H | -1.65865 | 3.59034 | -0.78337 |
| C | -0.44356 | 3.47632 | -2.58300 |
| C | 0.82403 | 3.11087 | -3.07861 |
| H | 1.06711 | 3.31097 | -4.13695 |
| C | -6.65914 | -0.14524 | -5.17083 |
| H | -5.99292 | 0.55912 | -5.72494 |
| H | -6.37885 | -1.19236 | -5.43925 |
| H | -7.70916 | 0.03568 | -5.47866 |
| C | 0.53923 | 3.97977 | 3.20450 |
| C | -0.57027 | 3.35176 | 3.80527 |
| H | -0.82933 | 3.59519 | 4.85056 |
| C | -1.37521 | 2.42541 | 3.11857 |
| C | -3.93972 | -2.24744 | 3.61532 |
| C | -3.92619 | -3.53095 | 2.74014 |
| H | -3.23720 | -3.42923 | 1.87708 |
| H | -3.59303 | -4.40254 | 3.34785 |
| H | -4.94417 | -3.75364 | 2.34983 |
| C | -7.78107 | 1.31652 | 3.93607 |
| H | -7.03855 | 1.49664 | 4.75028 |

Figure 2 - cont.

| | | | |
|---|---|---|---|
| H | -8.58444 | 2.07805 | 4.00472 |
| H | -8.23046 | 0.30393 | 4.07624 |
| C | 6.26146 | -2.68003 | -0.09373 |
| H | 7.18149 | -2.65731 | 0.51370 |
| C | 5.92310 | -3.85359 | -0.79085 |
| C | 4.75230 | -3.84205 | -1.57615 |
| H | 4.48405 | -4.74042 | -2.15937 |
| C | 3.90525 | -2.72015 | -1.64815 |
| C | -1.28087 | -2.40564 | -3.05069 |
| H | -2.08153 | -3.17615 | -3.10926 |
| H | -0.38180 | -2.80673 | -3.57026 |
| H | -1.02130 | -2.25752 | -1.98471 |
| C | -0.60496 | -0.02946 | -3.67658 |
| H | -0.91654 | 0.90092 | -4.19969 |
| H | -0.32171 | 0.24100 | -2.64145 |
| H | 0.29885 | -0.42206 | -4.19544 |
| C | 0.80626 | 3.68321 | 1.85696 |
| H | 1.62581 | 4.20436 | 1.33533 |
| C | -5.44516 | 0.10693 | -1.73763 |
| H | -6.42622 | 0.27605 | -1.27395 |
| C | -5.41968 | -0.07401 | -3.12500 |
| C | -4.21225 | -0.43795 | -3.74379 |
| H | -4.20094 | -0.64657 | -4.81910 |
| C | -3.01836 | -0.57045 | -3.00553 |
| C | -2.51890 | -1.98737 | 4.17514 |
| H | -2.52172 | -1.14514 | 4.90128 |
| H | -2.15562 | -2.88984 | 4.71665 |
| H | -1.79040 | -1.75959 | 3.37177 |
| O | 3.44981 | -0.44777 | -0.98123 |
| O | 3.71715 | 0.18398 | 1.49482 |
| O | 2.46961 | 1.69141 | -0.09871 |
| H | 6.80747 | -5.65617 | -1.64787 |
| H | 9.30600 | 2.60523 | 0.25557 |
| O | -1.80853 | -0.27659 | -0.98518 |
| O | -2.64764 | -1.28632 | 1.16676 |
| O | -1.85410 | 1.20712 | 1.10207 |

Figure 2 - cont.

| | | | |
|---|---|---|---|
| O | -7.20455 | 1.46686 | 2.65303 |
| O | -6.61508 | 0.07314 | -3.77393 |
| C | -4.54644 | 0.08817 | 0.54538 |
| C | -5.64555 | 0.84018 | 1.00890 |
| C | -6.15274 | 0.66301 | 2.30726 |
| C | -5.60999 | -0.34001 | 3.13451 |
| C | -4.46174 | -1.06749 | 2.74943 |
| C | -3.88600 | -0.74305 | 1.49271 |
| H | -6.14843 | 1.56927 | 0.35739 |
| H | -6.07779 | -0.55349 | 4.10266 |
| H | 3.64238 | 2.85407 | 2.15519 |
| H | 3.00838 | -2.29901 | -3.57649 |
| C | -2.58268 | 1.80706 | 3.77151 |
| H | -2.51807 | 0.69945 | 3.78710 |
| H | -2.69522 | 2.16371 | 4.81699 |
| H | -3.51393 | 2.05188 | 3.21361 |
| C | 1.40626 | 4.94373 | 3.98435 |
| H | 2.18250 | 4.40157 | 4.57308 |
| H | 1.93839 | 5.65099 | 3.31253 |
| H | 0.80742 | 5.54005 | 4.70707 |
| C | 3.15396 | 2.12871 | -2.84296 |
| H | 3.97592 | 2.48389 | -2.18431 |
| H | 3.28861 | 2.57381 | -3.85139 |
| H | 3.27981 | 1.02773 | -2.92399 |
| C | -1.49360 | 4.08072 | -3.48878 |
| H | -2.14003 | 3.28926 | -3.93503 |
| H | -2.16421 | 4.77240 | -2.93456 |
| H | -1.03428 | 4.64436 | -4.32973 |
| C | 2.71543 | -2.70136 | -2.57832 |
| H | 2.31205 | -3.72375 | -2.73455 |
| H | 1.89944 | -2.05348 | -2.20128 |
| C | 6.77641 | -5.09909 | -0.68606 |
| H | 7.82120 | -4.85704 | -0.39486 |
| H | 6.37447 | -5.79935 | 0.08290 |
| C | 4.54093 | 2.56540 | 2.74178 |
| H | 4.17001 | 1.98852 | 3.61890 |

Figure 2 - cont.

| | | | |
|---|---|---|---|
| H | 5.03570 | 3.48640 | 3.11583 |
| C | 9.20357 | 1.69929 | 0.89660 |
| H | 9.65655 | 1.94858 | 1.88216 |
| H | 9.81441 | 0.89444 | 0.43506 |
| H | 0.71433 | 0.30181 | 2.08996 |

INTERATOMIC DISTANCES

| | P 1 | C 2 | C 3 | Rh 4 | O 5 | O 6 |
|---|---|---|---|---|---|---|
| P 1 | 0.0000 | | | | | |
| C 2 | 3.5210 | 0.0000 | | | | |
| C 3 | 3.3881 | 2.8537 | 0.0000 | | | |
| Rh 4 | 2.3065 | 1.9160 | 1.9440 | 0.0000 | | |
| O 5 | 4.3714 | 3.7412 | 1.1587 | 3.0992 | 0.0000 | |
| O 6 | 4.4785 | 1.1602 | 3.8195 | 3.0750 | 4.5392 | 0.0000 |
| P 7 | 3.9325 | 3.7019 | 3.2153 | 2.3048 | 4.1196 | 4.7309 |
| C 8 | 5.9257 | 6.3419 | 4.8818 | 4.7829 | 5.3271 | 7.3807 |
| C 9 | 6.9326 | 6.8715 | 5.8299 | 5.5562 | 6.2962 | 7.8017 |
| C 10 | 9.0281 | 6.2830 | 7.1757 | 6.8097 | 7.5458 | 6.2582 |
| H 11 | 9.2298 | 6.5255 | 7.7453 | 7.1155 | 8.2403 | 6.4379 |
| H 12 | 9.8267 | 7.2291 | 7.8307 | 7.5945 | 8.1157 | 7.2756 |
| H 13 | 9.3059 | 6.2814 | 7.2864 | 7.0631 | 7.5649 | 6.0884 |
| C 14 | 2.6835 | 4.9725 | 3.9335 | 4.1379 | 4.3171 | 5.7329 |
| C 15 | 3.3611 | 5.3442 | 4.9379 | 4.9349 | 5.3365 | 5.8781 |
| C 16 | 3.3968 | 5.6074 | 5.7895 | 5.2870 | 6.3975 | 6.0667 |
| C 17 | 2.7174 | 4.9068 | 5.5682 | 4.6120 | 6.3859 | 5.3793 |
| C 18 | 3.7450 | 5.7497 | 6.7862 | 5.5753 | 7.6783 | 6.1017 |
| C 19 | 4.9767 | 7.0467 | 7.9808 | 6.9082 | 8.7939 | 7.3283 |
| H 20 | 5.8522 | 7.8118 | 8.9314 | 7.7282 | 9.7902 | 8.0337 |
| C 21 | 5.4094 | 7.5928 | 8.1814 | 7.4150 | 8.8490 | 7.8881 |
| C 22 | 4.7342 | 6.9422 | 7.1826 | 6.6920 | 7.7379 | 7.3076 |
| H 23 | 5.4707 | 7.6445 | 7.6152 | 7.3748 | 8.0293 | 8.0060 |
| C 24 | 2.7273 | 5.6213 | 5.2336 | 4.0215 | 6.1988 | 6.6445 |
| C 25 | 3.6389 | 6.8031 | 5.9616 | 5.1017 | 6.7725 | 7.8589 |
| C 26 | 6.0038 | 7.2760 | 4.9824 | 5.5175 | 5.0864 | 8.3921 |
| C 27 | 7.3132 | 8.7297 | 6.2724 | 6.9888 | 6.1905 | 9.8360 |

Figure 2 - cont.

| | | | | | | | |
|---|---|---|---|---|---|---|---|
| H | 28 | 7.8257 | 9.4608 | 7.1451 | 7.6537 | 7.1686 | 10.5894 |
| H | 29 | 7.2359 | 8.8726 | 6.2821 | 7.1446 | 6.1087 | 9.9735 |
| H | 30 | 8.0993 | 9.1576 | 6.6424 | 7.5247 | 6.4205 | 10.2207 |
| C | 31 | 4.3597 | 4.6172 | 5.3967 | 3.6826 | 6.4851 | 5.4092 |
| C | 32 | 3.7608 | 5.0419 | 5.6419 | 3.8979 | 6.7569 | 5.8953 |
| C | 33 | 3.5310 | 5.6387 | 5.5137 | 4.0947 | 6.5370 | 6.6401 |
| C | 34 | 4.7993 | 6.7996 | 6.3730 | 5.1651 | 7.3002 | 7.8281 |
| H | 35 | 5.5840 | 7.1129 | 6.8671 | 5.5994 | 7.7996 | 8.0893 |
| C | 36 | 5.3830 | 7.7997 | 6.9701 | 6.0356 | 7.7782 | 8.8787 |
| C | 37 | 4.8822 | 7.7818 | 6.7803 | 5.9918 | 7.5357 | 8.8715 |
| H | 38 | 5.7167 | 8.7388 | 7.5325 | 6.9234 | 8.1877 | 9.8390 |
| C | 39 | 10.7174 | 11.3423 | 9.5252 | 9.8065 | 9.5897 | 12.3433 |
| H | 40 | 10.4722 | 11.4416 | 9.5882 | 9.7954 | 9.7071 | 12.4910 |
| H | 41 | 10.6945 | 11.2439 | 9.2350 | 9.7354 | 9.1691 | 12.2373 |
| H | 42 | 11.7772 | 12.3185 | 10.5691 | 10.8244 | 10.6273 | 13.2952 |
| C | 43 | 5.2370 | 5.8202 | 7.3567 | 5.4254 | 8.5134 | 6.2814 |
| C | 44 | 5.6888 | 5.4881 | 7.1740 | 5.2805 | 8.3019 | 5.8713 |
| H | 45 | 6.6352 | 6.0422 | 7.9795 | 6.1102 | 9.0869 | 6.2410 |
| C | 46 | 5.3383 | 4.9014 | 6.2687 | 4.4953 | 7.3536 | 5.4321 |
| C | 47 | 7.6127 | 5.0909 | 5.7257 | 5.3761 | 6.1492 | 5.2861 |
| C | 48 | 7.7728 | 5.3054 | 5.2821 | 5.4797 | 5.4223 | 5.5703 |
| H | 49 | 6.9193 | 4.7404 | 4.2875 | 4.6603 | 4.4026 | 5.1899 |
| H | 50 | 8.1579 | 5.3665 | 5.5105 | 5.8582 | 5.5315 | 5.4354 |
| H | 51 | 8.6331 | 6.3656 | 6.0797 | 6.3752 | 6.1264 | 6.6750 |
| C | 52 | 10.9900 | 9.4554 | 10.0894 | 9.2416 | 10.6921 | 9.7674 |
| H | 53 | 10.6309 | 8.9566 | 9.8932 | 8.9055 | 10.5640 | 9.1795 |
| H | 54 | 11.8728 | 10.4776 | 11.1071 | 10.2129 | 11.7259 | 10.7990 |
| H | 55 | 11.3922 | 9.6214 | 10.1685 | 9.4993 | 10.6701 | 9.8843 |
| C | 56 | 4.6575 | 6.0631 | 5.5846 | 5.9149 | 5.7389 | 6.4326 |
| H | 57 | 5.3965 | 6.6156 | 6.4957 | 6.6877 | 6.6809 | 6.8307 |
| C | 58 | 5.3115 | 6.4436 | 5.4508 | 6.2318 | 5.3190 | 6.8461 |
| C | 59 | 4.8929 | 6.1648 | 4.5954 | 5.6337 | 4.3463 | 6.7533 |
| H | 60 | 5.7652 | 6.7960 | 4.9248 | 6.2485 | 4.4223 | 7.3796 |
| C | 61 | 3.6944 | 5.4650 | 3.7533 | 4.5899 | 3.7548 | 6.2379 |
| C | 62 | 5.6715 | 6.4742 | 3.8952 | 4.9022 | 3.7497 | 7.5313 |
| H | 63 | 6.6122 | 6.9691 | 4.4038 | 5.5719 | 4.0629 | 7.9553 |

Figure 2 - cont.

| | | | | | | | |
|---|---|---|---|---|---|---|---|
| H | 64 | 5.6626 | 6.7531 | 4.0053 | 5.2130 | 3.7003 | 7.7952 |
| H | 65 | 4.8422 | 5.3807 | 2.8921 | 3.8367 | 2.9263 | 6.4402 |
| C | 66 | 5.0969 | 7.0623 | 4.9927 | 5.1756 | 5.3263 | 8.2184 |
| H | 67 | 5.7604 | 7.8998 | 6.0186 | 5.9916 | 6.4140 | 9.0589 |
| H | 68 | 4.1297 | 6.1153 | 4.3235 | 4.2057 | 4.8664 | 7.2753 |
| H | 69 | 5.0796 | 7.3165 | 5.0779 | 5.4672 | 5.2925 | 8.4590 |
| C | 70 | 4.2784 | 5.6057 | 6.6447 | 4.7919 | 7.7895 | 6.2861 |
| H | 71 | 4.3448 | 6.2480 | 7.1168 | 5.3473 | 8.2395 | 6.9460 |
| C | 72 | 8.2413 | 8.2629 | 7.0744 | 6.9402 | 7.4205 | 9.1802 |
| H | 73 | 9.1025 | 8.8660 | 7.8986 | 7.6899 | 8.2515 | 9.7071 |
| C | 74 | 8.6733 | 9.0665 | 7.5015 | 7.5884 | 7.7229 | 10.0500 |
| C | 75 | 7.8993 | 8.6434 | 6.7639 | 7.0266 | 6.9212 | 9.6931 |
| H | 76 | 8.5115 | 9.4659 | 7.3849 | 7.8018 | 7.4343 | 10.5343 |
| C | 77 | 6.5110 | 7.3350 | 5.4276 | 5.6642 | 5.6675 | 8.4138 |
| C | 78 | 6.6655 | 3.8148 | 5.1013 | 4.4854 | 5.6795 | 3.8597 |
| H | 79 | 6.9132 | 4.1587 | 5.8520 | 4.9109 | 6.5523 | 4.0929 |
| H | 80 | 7.0619 | 3.8505 | 5.2653 | 4.8858 | 5.7065 | 3.6243 |
| H | 81 | 5.5859 | 2.9100 | 4.0851 | 3.3836 | 4.7694 | 3.2166 |
| O | 82 | 1.6931 | 4.7799 | 3.8249 | 3.5556 | 4.4767 | 5.6981 |
| O | 83 | 1.6594 | 3.6039 | 4.3996 | 3.2549 | 5.3284 | 4.2069 |
| O | 84 | 1.6787 | 4.8399 | 4.8211 | 3.5179 | 5.8235 | 5.7719 |
| H | 85 | 7.4212 | 8.2833 | 7.0341 | 8.1419 | 6.5977 | 8.5994 |
| H | 86 | 7.2348 | 9.7086 | 10.1561 | 9.3830 | 10.8058 | 10.0386 |
| O | 87 | 4.5497 | 5.1169 | 3.7549 | 3.4477 | 4.3985 | 6.2055 |
| O | 88 | 5.4158 | 4.1699 | 3.7583 | 3.3796 | 4.3702 | 4.9750 |
| O | 89 | 4.5916 | 4.5985 | 4.7934 | 3.4387 | 5.7687 | 5.4961 |
| O | 90 | 10.1016 | 8.9205 | 9.2682 | 8.4463 | 9.8810 | 9.3885 |
| O | 91 | 10.0279 | 10.3932 | 8.8305 | 8.9483 | 8.9973 | 11.3534 |
| C | 92 | 7.0789 | 6.4109 | 5.9731 | 5.4371 | 6.5439 | 7.1962 |
| C | 93 | 8.2382 | 7.4901 | 7.3294 | 6.6520 | 7.9232 | 8.1806 |
| C | 94 | 8.9217 | 7.6772 | 7.9191 | 7.1742 | 8.5161 | 8.1917 |
| C | 95 | 8.6154 | 6.8595 | 7.3291 | 6.6577 | 7.8867 | 7.2392 |
| C | 96 | 7.4818 | 5.6021 | 5.9591 | 5.4077 | 6.4970 | 6.0358 |
| C | 97 | 6.5689 | 5.2899 | 5.1493 | 4.6298 | 5.7288 | 5.9732 |
| H | 98 | 8.8061 | 8.3945 | 8.1013 | 7.4104 | 8.6947 | 9.1374 |
| H | 99 | 9.4142 | 7.3661 | 8.0799 | 7.4065 | 8.6110 | 7.5903 |

Figure 2 - cont.

| | | | | | | |
|---|---|---|---|---|---|---|
| H 100 | 3.5023 | 5.3751 | 6.6225 | 4.9755 | 7.6923 | 5.8581 |
| H 101 | 4.6045 | 6.8161 | 4.5315 | 5.4514 | 4.4269 | 7.7703 |
| C 102 | 6.3961 | 5.2181 | 6.6197 | 5.0706 | 7.5998 | 5.6060 |
| H 103 | 6.1437 | 4.4723 | 5.8815 | 4.4980 | 6.7964 | 4.8239 |
| H 104 | 7.1905 | 5.7961 | 7.5059 | 5.9227 | 8.4838 | 5.9916 |
| H 105 | 6.9780 | 6.0126 | 7.0364 | 5.6271 | 7.9604 | 6.4949 |
| C 106 | 6.1857 | 6.8394 | 8.5857 | 6.6505 | 9.7426 | 7.1434 |
| H 107 | 6.0638 | 6.5128 | 8.4884 | 6.5783 | 9.6289 | 6.6792 |
| H 108 | 6.3481 | 7.5170 | 9.0365 | 7.1394 | 10.1888 | 7.9045 |
| H 109 | 7.2056 | 7.5622 | 9.4148 | 7.4709 | 10.5693 | 7.7882 |
| C 110 | 3.8415 | 7.2989 | 6.3165 | 5.7085 | 7.0049 | 8.3076 |
| H 111 | 3.7796 | 7.2855 | 6.6738 | 5.8939 | 7.4261 | 8.2034 |
| H 112 | 4.9407 | 8.3810 | 7.2438 | 6.7459 | 7.8541 | 9.4029 |
| H 113 | 3.4838 | 6.8772 | 5.6096 | 5.2971 | 6.1833 | 7.8924 |
| C 114 | 6.8499 | 9.0963 | 8.1246 | 7.3174 | 8.8478 | 10.1809 |
| H 115 | 7.1020 | 9.1511 | 7.9120 | 7.3286 | 8.5275 | 10.2615 |
| H 116 | 7.4062 | 9.4051 | 8.6872 | 7.7237 | 9.4685 | 10.4427 |
| H 117 | 7.4445 | 9.9532 | 8.9060 | 8.1521 | 9.5954 | 11.0446 |
| C 118 | 4.0314 | 5.8270 | 3.5105 | 4.5877 | 3.3778 | 6.7509 |
| H 119 | 4.8907 | 6.1175 | 3.5599 | 5.0204 | 3.0659 | 6.9840 |
| H 120 | 3.3736 | 5.2157 | 2.8597 | 3.7474 | 2.9841 | 6.2390 |
| C 121 | 6.7703 | 7.5082 | 6.5877 | 7.5182 | 6.2855 | 7.7531 |
| H 122 | 7.2694 | 8.1109 | 7.4603 | 8.2063 | 7.2560 | 8.2816 |
| H 123 | 7.0234 | 7.2158 | 6.4427 | 7.4581 | 6.0652 | 7.3360 |
| C 124 | 4.0029 | 5.5766 | 7.0241 | 5.4838 | 8.0412 | 5.8831 |
| H 125 | 4.1359 | 4.9369 | 6.7724 | 5.1929 | 7.7924 | 5.0742 |
| H 126 | 5.0630 | 6.6071 | 8.1270 | 6.5505 | 9.1500 | 6.8445 |
| C 127 | 6.8919 | 9.0757 | 9.6352 | 8.9243 | 10.2519 | 9.3200 |
| H 128 | 7.5292 | 9.4166 | 10.2575 | 9.4504 | 10.9065 | 9.5415 |
| H 129 | 7.3317 | 9.4743 | 9.8342 | 9.3317 | 10.3394 | 9.7115 |
| H 130 | 2.5309 | 2.3075 | 3.5634 | 1.6219 | 4.7146 | 3.2129 |

| | P 7 | C 8 | C 9 | C 10 | H 11 | H 12 |
|---|---|---|---|---|---|---|
| P 7 | 0.0000 | | | | | |
| C 8 | 2.7829 | 0.0000 | | | | |

Figure 2 - cont.

| | | | | | | |
|---|---|---|---|---|---|---|
| C | 9 | 3.3125 | 1.4307 | 0.0000 | | |
| C | 10 | 5.8962 | 7.0457 | 6.3167 | 0.0000 | |
| H | 11 | 6.2027 | 7.5030 | 6.7091 | 1.1126 | 0.0000 |
| H | 12 | 6.4563 | 7.1900 | 6.3215 | 1.1123 | 1.8052 | 0.0000 |
| H | 13 | 6.4722 | 7.7884 | 7.1850 | 1.1122 | 1.7893 | 1.7926 |
| C | 14 | 5.9527 | 7.4562 | 8.6824 | 10.7969 | 11.1781 | 11.5604 |
| C | 15 | 6.9662 | 8.7215 | 9.8869 | 11.4858 | 11.7991 | 12.3284 |
| C | 16 | 7.2785 | 9.2097 | 10.2963 | 11.8138 | 11.9922 | 12.7118 |
| C | 17 | 6.5058 | 8.6286 | 9.5934 | 10.9675 | 11.0450 | 11.8902 |
| C | 18 | 7.2877 | 9.4624 | 10.3288 | 11.5727 | 11.5212 | 12.5274 |
| C | 19 | 8.6485 | 10.7326 | 11.6470 | 12.9485 | 12.8910 | 13.9132 |
| H | 20 | 9.3589 | 11.4605 | 12.3084 | 13.5205 | 13.3817 | 14.4994 |
| C | 21 | 9.2794 | 11.2393 | 12.2664 | 13.7141 | 13.7501 | 14.6637 |
| C | 22 | 8.6496 | 10.5246 | 11.6277 | 13.1682 | 13.3123 | 14.0847 |
| H | 23 | 9.3532 | 11.0968 | 12.2647 | 13.8971 | 14.1037 | 14.7936 |
| C | 24 | 4.1475 | 5.2512 | 6.1953 | 9.8058 | 9.8895 | 10.4554 |
| C | 25 | 5.1352 | 5.6339 | 6.7091 | 10.9553 | 11.1004 | 11.5366 |
| C | 26 | 4.4102 | 2.6162 | 3.9291 | 9.2109 | 9.7959 | 9.3767 |
| C | 27 | 5.9530 | 3.9227 | 5.0543 | 10.4982 | 11.1346 | 10.5676 |
| H | 28 | 6.4713 | 4.2610 | 5.2756 | 11.1083 | 11.6801 | 11.1490 |
| H | 29 | 6.4499 | 4.7693 | 6.0041 | 11.1846 | 11.8417 | 11.3158 |
| H | 30 | 6.3998 | 4.2139 | 5.1633 | 10.3949 | 11.1046 | 10.3653 |
| C | 31 | 2.7286 | 4.6088 | 4.7208 | 6.7387 | 6.5803 | 7.4111 |
| C | 32 | 3.4349 | 5.1193 | 5.5124 | 8.1020 | 7.9641 | 8.7909 |
| C | 33 | 3.5623 | 4.6222 | 5.3060 | 8.9581 | 8.9600 | 9.5610 |
| C | 34 | 4.0837 | 4.2721 | 4.8477 | 9.3433 | 9.3541 | 9.8083 |
| H | 35 | 4.1685 | 4.1980 | 4.4431 | 8.8930 | 8.8339 | 9.2968 |
| C | 36 | 5.0527 | 4.6795 | 5.4303 | 10.5067 | 10.5915 | 10.9123 |
| C | 37 | 5.5006 | 5.3596 | 6.3491 | 11.2491 | 11.3908 | 11.7209 |
| H | 38 | 6.4596 | 6.0252 | 7.0564 | 12.2273 | 12.4053 | 12.6603 |
| C | 39 | 7.8348 | 5.0700 | 4.8587 | 10.4280 | 10.9526 | 10.0567 |
| H | 40 | 7.8899 | 5.1276 | 5.1153 | 11.0465 | 11.5269 | 10.7609 |
| H | 41 | 7.8985 | 5.1535 | 5.1108 | 10.4580 | 11.0806 | 10.0833 |
| H | 42 | 8.7942 | 6.0619 | 5.6900 | 10.9888 | 11.4900 | 10.5289 |
| C | 43 | 5.3807 | 7.3644 | 7.4944 | 8.6091 | 8.1793 | 9.4190 |
| C | 44 | 4.9398 | 6.9766 | 6.8873 | 7.3483 | 6.8502 | 8.1465 |

Figure 2 - cont.

| | | | | | | | |
|---|---|---|---|---|---|---|---|
| H | 45 | 5.8032 | 7.8542 | 7.6333 | 7.3297 | 6.6883 | 8.1440 |
| C | 46 | 3.7255 | 5.6995 | 5.5436 | 6.2907 | 5.9165 | 7.0278 |
| C | 47 | 4.3939 | 5.6498 | 5.0908 | 1.5462 | 2.2218 | 2.2202 |
| C | 48 | 4.6168 | 5.4967 | 5.1154 | 2.4970 | 3.4959 | 2.7629 |
| H | 49 | 3.8338 | 4.6989 | 4.5637 | 3.4855 | 4.3858 | 3.8063 |
| H | 50 | 5.3877 | 6.4670 | 6.1874 | 2.7067 | 3.7373 | 3.0623 |
| H | 51 | 5.2454 | 5.5927 | 5.0383 | 2.7633 | 3.8058 | 2.5623 |
| C | 52 | 7.4049 | 7.4574 | 6.1370 | 4.9020 | 4.4430 | 4.5281 |
| H | 53 | 7.2507 | 7.7100 | 6.4899 | 4.5701 | 3.8969 | 4.4160 |
| H | 54 | 8.3259 | 8.2238 | 6.8681 | 5.9725 | 5.4701 | 5.5574 |
| H | 55 | 7.7098 | 7.7087 | 6.3852 | 4.4579 | 4.1336 | 3.8744 |
| C | 56 | 8.0196 | 9.7389 | 10.9157 | 12.1657 | 12.5413 | 13.0084 |
| H | 57 | 8.8667 | 10.7208 | 11.8606 | 12.7951 | 13.1210 | 13.6833 |
| C | 58 | 8.2235 | 9.6974 | 10.9149 | 12.2341 | 12.7252 | 13.0070 |
| C | 59 | 7.3923 | 8.5812 | 9.8440 | 11.6269 | 12.1841 | 12.3196 |
| H | 60 | 7.8384 | 8.7766 | 10.0471 | 11.8776 | 12.5177 | 12.5024 |
| C | 61 | 6.2193 | 7.3756 | 8.6619 | 10.9012 | 11.4115 | 11.5827 |
| C | 62 | 4.2094 | 3.1215 | 4.3965 | 8.6518 | 9.3445 | 8.8694 |
| H | 63 | 4.7371 | 3.4033 | 4.4415 | 8.4316 | 9.2143 | 8.5342 |
| H | 64 | 4.9593 | 4.1686 | 5.4868 | 9.5197 | 10.2264 | 9.7872 |
| H | 65 | 3.2519 | 2.8607 | 4.1095 | 7.8223 | 8.4798 | 8.1413 |
| C | 66 | 4.3644 | 3.2173 | 4.5887 | 9.8289 | 10.2927 | 10.1283 |
| H | 67 | 4.9845 | 3.5630 | 4.7745 | 10.4270 | 10.8250 | 10.6850 |
| H | 68 | 3.4637 | 2.9693 | 4.3207 | 9.1651 | 9.5614 | 9.5573 |
| H | 69 | 5.0882 | 4.2391 | 5.6412 | 10.6024 | 11.1003 | 10.9430 |
| C | 70 | 4.7327 | 6.5295 | 6.8707 | 8.9153 | 8.6433 | 9.6773 |
| H | 71 | 5.4833 | 7.1203 | 7.5949 | 9.9778 | 9.7307 | 10.7403 |
| C | 72 | 4.7199 | 2.4246 | 1.4147 | 7.0916 | 7.5028 | 6.8908 |
| H | 73 | 5.4262 | 3.4328 | 2.1849 | 6.8877 | 7.2404 | 6.5547 |
| C | 74 | 5.5121 | 2.8172 | 2.4683 | 8.3350 | 8.8177 | 8.1092 |
| C | 75 | 5.1982 | 2.4347 | 2.8452 | 8.8408 | 9.3823 | 8.7404 |
| H | 76 | 6.1290 | 3.4295 | 3.9401 | 9.8452 | 10.4250 | 9.7165 |
| C | 77 | 3.9789 | 1.4283 | 2.4953 | 8.2768 | 8.8113 | 8.3439 |
| C | 78 | 4.0964 | 6.0524 | 5.7633 | 2.4925 | 2.7605 | 3.4902 |
| H | 79 | 4.5175 | 6.5871 | 6.2049 | 2.7199 | 2.5165 | 3.7713 |
| H | 80 | 4.9035 | 6.8994 | 6.6990 | 2.7365 | 3.1145 | 3.7572 |

Figure 2 - cont.

| | | | | | | |
|---|---|---|---|---|---|---|
| H 81 | 3.1391 | 5.3455 | 5.2817 | 3.4848 | 3.7886 | 4.3857 |
| O 82 | 5.0800 | 6.5374 | 7.7478 | 10.3506 | 10.6608 | 11.0918 |
| O 83 | 5.1922 | 7.4637 | 8.3641 | 9.5950 | 9.6955 | 10.5056 |
| O 84 | 4.3986 | 6.0577 | 7.0103 | 9.7870 | 9.8648 | 10.5463 |
| H 85 | 10.0203 | 11.2322 | 12.4753 | 13.7091 | 14.3026 | 14.4181 |
| H 86 | 11.0805 | 12.8301 | 13.8872 | 15.7476 | 15.7461 | 16.6825 |
| O 87 | 1.6536 | 1.3935 | 2.4928 | 6.9371 | 7.3467 | 7.2912 |
| O 88 | 1.6890 | 2.9783 | 2.9621 | 4.4513 | 4.9275 | 4.8958 |
| O 89 | 1.6827 | 3.3166 | 3.3897 | 6.0684 | 6.0968 | 6.6177 |
| O 90 | 6.4345 | 6.1985 | 4.8503 | 5.1087 | 4.8388 | 4.8000 |
| O 91 | 6.8447 | 4.1823 | 3.6738 | 9.1490 | 9.6212 | 8.7847 |
| C 92 | 3.2010 | 2.6445 | 1.5054 | 5.0216 | 5.2985 | 5.0693 |
| C 93 | 4.4471 | 3.8485 | 2.5143 | 5.1445 | 5.2248 | 5.0314 |
| C 94 | 5.1681 | 5.0802 | 3.7987 | 4.2586 | 4.1706 | 4.0816 |
| C 95 | 4.9322 | 5.3863 | 4.2941 | 2.8584 | 2.8304 | 2.8028 |
| C 96 | 3.8295 | 4.6449 | 3.8425 | 2.5652 | 2.8803 | 2.8391 |
| C 97 | 2.6956 | 3.2422 | 2.5725 | 3.9009 | 4.2663 | 4.1549 |
| H 98 | 5.1445 | 4.1052 | 2.7529 | 6.1913 | 6.2294 | 6.0067 |
| H 99 | 5.8640 | 6.4661 | 5.3768 | 2.4223 | 2.1603 | 2.2548 |
| H 100 | 6.1379 | 8.2976 | 8.9707 | 10.4121 | 10.2390 | 11.3254 |
| H 101 | 6.3721 | 6.6871 | 8.0926 | 11.5149 | 12.0802 | 12.0436 |
| C 102 | 4.0027 | 5.7894 | 5.3177 | 5.0066 | 4.5325 | 5.6993 |
| H 103 | 3.5306 | 5.5090 | 5.0885 | 4.1191 | 3.7847 | 4.8982 |
| H 104 | 5.0658 | 6.8833 | 6.3444 | 5.1649 | 4.4778 | 5.8894 |
| H 105 | 4.1267 | 5.3755 | 4.6878 | 5.0345 | 4.5966 | 5.5312 |
| C 106 | 6.8491 | 8.8588 | 8.9961 | 9.7873 | 9.2671 | 10.6371 |
| H 107 | 7.1223 | 9.3576 | 9.5629 | 9.8836 | 9.3768 | 10.8058 |
| H 108 | 7.3502 | 9.1837 | 9.4123 | 10.7419 | 10.2595 | 11.5660 |
| H 109 | 7.4823 | 9.4173 | 9.3993 | 9.8594 | 9.2309 | 10.6800 |
| C 110 | 6.2008 | 6.7746 | 7.9662 | 12.0296 | 12.2244 | 12.6517 |
| H 111 | 6.6578 | 7.5778 | 8.7130 | 12.3425 | 12.4731 | 13.0378 |
| H 112 | 7.0748 | 7.3102 | 8.5107 | 12.9502 | 13.1571 | 13.5249 |
| H 113 | 5.9978 | 6.6019 | 7.8873 | 11.7883 | 12.0705 | 12.4096 |
| C 114 | 6.0206 | 5.0011 | 5.5576 | 11.1382 | 11.2260 | 11.4145 |
| H 115 | 5.8587 | 4.3600 | 4.9353 | 10.8586 | 11.0370 | 11.0514 |
| H 116 | 6.2611 | 5.3010 | 5.5840 | 10.9862 | 10.9836 | 11.2344 |

Figure 2 - cont.

| | | | | | | |
|---|---|---|---|---|---|---|
| H 117 | 7.0168 | 5.9803 | 6.6009 | 12.2400 | 12.3305 | 12.5199 |
| C 118 | 5.7018 | 6.3325 | 7.6841 | 10.5960 | 11.1743 | 11.1603 |
| H 119 | 6.0243 | 6.4752 | 7.7902 | 10.4914 | 11.1626 | 10.9962 |
| H 120 | 4.6461 | 5.2956 | 6.6406 | 9.7632 | 10.3056 | 10.3174 |
| C 121 | 9.5319 | 10.9873 | 12.1859 | 13.1345 | 13.6681 | 13.9019 |
| H 122 | 10.2984 | 11.8619 | 13.0582 | 13.9147 | 14.3934 | 14.7255 |
| H 123 | 9.4994 | 11.0555 | 12.1814 | 12.6307 | 13.1877 | 13.4011 |
| C 124 | 6.9209 | 9.2046 | 9.8963 | 10.8951 | 10.7170 | 11.8596 |
| H 125 | 6.7196 | 9.2018 | 9.8046 | 10.1707 | 9.9655 | 11.1755 |
| H 126 | 7.8683 | 10.0982 | 10.7407 | 11.7072 | 11.4516 | 12.6774 |
| C 127 | 10.7733 | 12.6680 | 13.7162 | 15.2046 | 15.2239 | 16.1632 |
| H 128 | 11.3341 | 13.3696 | 14.3543 | 15.4768 | 15.4378 | 16.4705 |
| H 129 | 11.2557 | 13.0839 | 14.1928 | 15.6980 | 15.7827 | 16.6460 |
| H 130 | 2.6358 | 5.3123 | 5.8499 | 6.8251 | 6.8746 | 7.6858 |

| | H 13 | C 14 | C 15 | C 16 | C 17 | C 18 |
|---|---|---|---|---|---|---|
| H 13 | 0.0000 | | | | | |
| C 14 | 10.9003 | 0.0000 | | | | |
| C 15 | 11.5102 | 1.4180 | 0.0000 | | | |
| C 16 | 11.8843 | 2.5386 | 1.4876 | 0.0000 | | |
| C 17 | 11.1022 | 3.1390 | 2.5470 | 1.4133 | 0.0000 | |
| C 18 | 11.7416 | 4.5156 | 3.8495 | 2.4745 | 1.4141 | 0.0000 |
| C 19 | 13.0874 | 5.2205 | 4.3105 | 2.8235 | 2.4152 | 1.4054 |
| H 20 | 13.6811 | 6.3030 | 5.4147 | 3.9277 | 3.4137 | 2.1617 |
| C 21 | 13.8001 | 4.9195 | 3.8177 | 2.4700 | 2.8194 | 2.4662 |
| C 22 | 13.2214 | 3.7005 | 2.5111 | 1.4160 | 2.4188 | 2.8201 |
| H 23 | 13.9133 | 3.9143 | 2.6965 | 2.1689 | 3.4154 | 3.9226 |
| C 24 | 10.3588 | 4.7296 | 5.5325 | 5.2861 | 4.4937 | 4.9289 |
| C 25 | 11.5271 | 4.9530 | 5.8352 | 5.6821 | 5.1675 | 5.6333 |
| C 26 | 9.7885 | 6.6450 | 8.0469 | 8.7797 | 8.5714 | 9.5903 |
| C 27 | 11.0684 | 7.5997 | 9.0141 | 9.8271 | 9.7600 | 10.8019 |
| H 28 | 11.7541 | 8.2523 | 9.6486 | 10.3529 | 10.2325 | 11.1825 |
| H 29 | 11.6836 | 7.1426 | 8.5433 | 9.4338 | 9.5197 | 10.6146 |
| H 30 | 10.9423 | 8.3420 | 9.7594 | 10.6503 | 10.5969 | 11.6810 |
| C 31 | 7.4326 | 6.9850 | 7.6845 | 7.4519 | 6.2961 | 6.5489 |

Figure 2 - cont.

| | | | | | | |
|---|---|---|---|---|---|---|
| C | 32 | 8.7482 | 6.3865 | 7.0290 | 6.6435 | 5.4760 | 5.6205 |
| C | 33 | 9.6163 | 5.8661 | 6.6860 | 6.4303 | 5.4707 | 5.7811 |
| C | 34 | 10.1119 | 6.9339 | 7.8681 | 7.6880 | 6.8066 | 7.1039 |
| H | 35 | 9.7401 | 7.8536 | 8.7812 | 8.5898 | 7.6259 | 7.8631 |
| C | 36 | 11.2721 | 7.1064 | 8.1087 | 7.9973 | 7.2998 | 7.6458 |
| C | 37 | 11.9225 | 6.2107 | 7.1815 | 7.0846 | 6.5625 | 6.9700 |
| H | 38 | 12.9023 | 6.6818 | 7.6578 | 7.6103 | 7.2419 | 7.6579 |
| C | 39 | 11.2617 | 11.8095 | 13.1887 | 13.7943 | 13.3682 | 14.1909 |
| H | 40 | 11.8932 | 11.5302 | 12.9067 | 13.4636 | 13.0575 | 13.8431 |
| H | 41 | 11.2118 | 11.5710 | 12.9699 | 13.6853 | 13.3547 | 14.2676 |
| H | 42 | 11.8455 | 12.9137 | 14.2899 | 14.8810 | 14.4293 | 15.2252 |
| C | 43 | 9.1852 | 7.8373 | 8.0942 | 7.3489 | 5.9696 | 5.5878 |
| C | 44 | 7.9583 | 8.3412 | 8.6886 | 8.1108 | 6.7565 | 6.5529 |
| H | 45 | 7.9062 | 9.2466 | 9.5095 | 8.8872 | 7.5129 | 7.2141 |
| C | 46 | 6.9777 | 7.9834 | 8.5279 | 8.1838 | 6.9288 | 7.0065 |
| C | 47 | 2.1804 | 9.3693 | 10.1345 | 10.5067 | 9.6976 | 10.3809 |
| C | 48 | 2.7071 | 9.1547 | 10.0086 | 10.5929 | 9.9663 | 10.8247 |
| H | 49 | 3.7228 | 8.1925 | 9.1170 | 9.7675 | 9.2099 | 10.1452 |
| H | 50 | 2.4388 | 9.3490 | 10.1070 | 10.7371 | 10.1752 | 11.0604 |
| H | 51 | 3.0937 | 9.9867 | 10.9157 | 11.5407 | 10.9310 | 11.8021 |
| C | 52 | 5.9381 | 13.2819 | 14.1297 | 14.1931 | 13.1152 | 13.4336 |
| H | 53 | 5.5620 | 12.9877 | 13.7438 | 13.7294 | 12.6032 | 12.8507 |
| H | 54 | 6.9845 | 14.2143 | 15.0672 | 15.0846 | 13.9764 | 14.2356 |
| H | 55 | 5.4334 | 13.5629 | 14.4283 | 14.5857 | 13.5650 | 13.9665 |
| C | 56 | 12.0775 | 2.4239 | 1.4133 | 2.5165 | 3.7274 | 4.9140 |
| H | 57 | 12.6576 | 3.4208 | 2.1674 | 2.7104 | 3.9454 | 4.9133 |
| C | 58 | 12.1050 | 2.8229 | 2.4678 | 3.8201 | 4.9557 | 6.2269 |
| C | 59 | 11.5698 | 2.4168 | 2.8203 | 4.3033 | 5.2533 | 6.6234 |
| H | 60 | 11.7918 | 3.4146 | 3.9243 | 5.4064 | 6.3408 | 7.7190 |
| C | 61 | 10.9643 | 1.4140 | 2.4745 | 3.8382 | 4.5357 | 5.9231 |
| C | 62 | 9.0775 | 5.9977 | 7.3900 | 8.3053 | 8.2081 | 9.3642 |
| H | 63 | 8.8306 | 6.8988 | 8.2662 | 9.2432 | 9.1551 | 10.3316 |
| H | 64 | 9.8670 | 5.4933 | 6.8915 | 7.9200 | 8.0075 | 9.2321 |
| H | 65 | 8.2213 | 5.4281 | 6.7716 | 7.6302 | 7.4324 | 8.5785 |
| C | 66 | 10.4163 | 5.8122 | 7.1746 | 7.7503 | 7.5228 | 8.4581 |
| H | 67 | 11.0939 | 6.6221 | 7.9357 | 8.3783 | 8.0871 | 8.8956 |

Figure 2 - cont.

| | | | | | | |
|---|---|---|---|---|---|---|
| H 68 | 9.7455 | 5.2265 | 6.5371 | 7.0027 | 6.6386 | 7.5355 |
| H 69 | 11.1129 | 5.2843 | 6.6541 | 7.3290 | 7.2959 | 8.3034 |
| C 70 | 9.5147 | 6.8628 | 7.2539 | 6.5857 | 5.2871 | 5.0736 |
| H 71 | 10.5578 | 6.7300 | 7.0412 | 6.2415 | 4.9862 | 4.6215 |
| C 72 | 7.9997 | 9.8789 | 11.1330 | 11.5786 | 10.9131 | 11.6455 |
| H 73 | 7.8536 | 10.8445 | 12.0660 | 12.4727 | 11.7444 | 12.4236 |
| C 74 | 9.1872 | 10.0405 | 11.3675 | 11.8988 | 11.3585 | 12.1546 |
| C 75 | 9.6029 | 9.0060 | 10.3729 | 10.9811 | 10.5657 | 11.4416 |
| H 76 | 10.5747 | 9.3695 | 10.7656 | 11.4370 | 11.1272 | 12.0401 |
| C 77 | 8.9760 | 7.6396 | 8.9938 | 9.6001 | 9.1875 | 10.0971 |
| C 78 | 2.7009 | 8.4617 | 9.0688 | 9.3407 | 8.4914 | 9.1211 |
| H 79 | 3.0228 | 8.9185 | 9.4337 | 9.5361 | 8.5619 | 9.0269 |
| H 80 | 2.4690 | 8.6101 | 9.1210 | 9.4567 | 8.6960 | 9.3697 |
| H 81 | 3.7371 | 7.3925 | 8.0457 | 8.3398 | 7.5153 | 8.2107 |
| O 82 | 10.5876 | 1.3913 | 2.4255 | 2.8847 | 2.9309 | 4.1627 |
| O 83 | 9.7533 | 3.0106 | 2.9251 | 2.4354 | 1.3942 | 2.3970 |
| O 84 | 10.2107 | 3.8080 | 4.3839 | 4.0024 | 3.1158 | 3.6308 |
| H 85 | 13.4878 | 4.8707 | 4.6072 | 5.8802 | 7.0962 | 8.3126 |
| H 86 | 15.8854 | 6.6618 | 5.6628 | 4.4599 | 4.8361 | 4.2469 |
| O 87 | 7.5814 | 6.1992 | 7.4142 | 7.8591 | 7.2548 | 8.1094 |
| O 88 | 5.0618 | 7.2033 | 8.2039 | 8.6366 | 7.9060 | 8.7162 |
| O 89 | 6.8159 | 6.9996 | 7.8943 | 7.9184 | 6.9226 | 7.4102 |
| O 90 | 6.2124 | 12.3708 | 13.2972 | 13.3935 | 12.3530 | 12.7215 |
| O 91 | 10.0279 | 11.3647 | 12.7040 | 13.2408 | 12.7040 | 13.4796 |
| C 92 | 5.9674 | 9.0679 | 10.1478 | 10.4569 | 9.6224 | 10.2652 |
| C 93 | 6.2054 | 10.3630 | 11.4013 | 11.6130 | 10.6891 | 11.2107 |
| C 94 | 5.3662 | 11.1114 | 12.0556 | 12.2238 | 11.2388 | 11.7015 |
| C 95 | 3.9644 | 10.7208 | 11.5919 | 11.8070 | 10.8484 | 11.3615 |
| C 96 | 3.5206 | 9.4543 | 10.3312 | 10.6327 | 9.7526 | 10.3763 |
| C 97 | 4.7509 | 8.5186 | 9.5077 | 9.8498 | 9.0219 | 9.7105 |
| H 98 | 7.2649 | 10.9369 | 12.0134 | 12.1930 | 11.2667 | 11.7455 |
| H 99 | 3.5086 | 11.5159 | 12.3181 | 12.5087 | 11.5265 | 11.9970 |
| H 100 | 10.7455 | 5.4114 | 5.2584 | 4.1855 | 2.8222 | 2.1735 |
| H 101 | 11.7297 | 3.0503 | 4.2946 | 5.4154 | 5.9802 | 7.2529 |
| C 102 | 5.7706 | 8.9365 | 9.5305 | 9.3210 | 8.1170 | 8.2867 |
| H 103 | 4.8159 | 8.5351 | 9.1525 | 9.0843 | 7.9666 | 8.2925 |

Figure 2 - cont.

| | | | | | | |
|---|---|---|---|---|---|---|
| H 104 | 5.8687 | 9.7358 | 10.2178 | 9.9144 | 8.6580 | 8.6981 |
| H 105 | 5.9467 | 9.5021 | 10.2131 | 10.0657 | 8.8952 | 9.1053 |
| C 106 | 10.3042 | 8.6241 | 8.6661 | 7.7045 | 6.3031 | 5.5909 |
| H 107 | 10.2885 | 8.3583 | 8.2400 | 7.2142 | 5.8134 | 5.0123 |
| H 108 | 11.2853 | 8.6758 | 8.6979 | 7.6503 | 6.2955 | 5.4673 |
| H 109 | 10.4062 | 9.6871 | 9.7386 | 8.7864 | 7.3801 | 6.6487 |
| C 110 | 12.5107 | 4.3360 | 5.0965 | 4.9634 | 4.7794 | 5.3132 |
| H 111 | 12.7821 | 4.2766 | 4.7387 | 4.3146 | 4.0843 | 4.4310 |
| H 112 | 13.4658 | 5.1952 | 5.9425 | 5.8352 | 5.7653 | 6.2265 |
| H 113 | 12.1998 | 3.4508 | 4.3621 | 4.5220 | 4.5643 | 5.3656 |
| C 114 | 11.9846 | 8.4758 | 9.5344 | 9.4725 | 8.8073 | 9.1353 |
| H 115 | 11.7089 | 8.5948 | 9.7597 | 9.8608 | 9.2702 | 9.7388 |
| H 116 | 11.8900 | 9.2588 | 10.2704 | 10.1219 | 9.3356 | 9.5557 |
| H 117 | 13.0754 | 8.8634 | 9.8858 | 9.7886 | 9.2064 | 9.4866 |
| C 118 | 10.7548 | 2.5457 | 3.8549 | 5.0713 | 5.5534 | 6.8990 |
| H 119 | 10.5905 | 3.4310 | 4.6338 | 5.9557 | 6.4678 | 7.8456 |
| H 120 | 10.0026 | 2.7361 | 4.1446 | 5.1630 | 5.3594 | 6.6495 |
| C 121 | 12.8999 | 4.3351 | 3.8540 | 5.0572 | 6.2407 | 7.4274 |
| H 122 | 13.6674 | 4.8701 | 4.0994 | 5.0585 | 6.3196 | 7.3661 |
| H 123 | 12.3145 | 4.8206 | 4.3797 | 5.5701 | 6.6130 | 7.8076 |
| C 124 | 11.1305 | 5.5164 | 5.0784 | 3.8472 | 2.5337 | 1.5086 |
| H 125 | 10.3400 | 5.7474 | 5.2937 | 4.2043 | 2.8839 | 2.1735 |
| H 126 | 11.9604 | 6.5039 | 5.9837 | 4.6434 | 3.4563 | 2.1701 |
| C 127 | 15.2744 | 6.2018 | 5.0529 | 3.8586 | 4.3328 | 3.8477 |
| H 128 | 15.5122 | 7.0239 | 5.8138 | 4.5642 | 4.8608 | 4.1695 |
| H 129 | 15.7223 | 6.2307 | 5.0216 | 4.0797 | 4.8595 | 4.6449 |
| H 130 | 7.1773 | 4.9903 | 5.5392 | 5.4511 | 4.4092 | 4.9929 |

| | C 19 | H 20 | C 21 | C 22 | H 23 | C 24 |
|---|---|---|---|---|---|---|
| C 19 | 0.0000 | | | | | |
| H 20 | 1.1043 | 0.0000 | | | | |
| C 21 | 1.4117 | 2.1774 | 0.0000 | | | |
| C 22 | 2.4136 | 3.4168 | 1.4043 | 0.0000 | | |
| H 23 | 3.4163 | 4.3318 | 2.1693 | 1.1026 | 0.0000 | |
| C 24 | 6.0058 | 6.6008 | 6.6357 | 6.3013 | 7.0624 | 0.0000 |

Figure 2 - cont.

| | | | | | | | |
|---|---|---|---|---|---|---|---|
| C | 25 | 6.4922 | 7.0961 | 6.9205 | 6.5387 | 7.1529 | 1.4169 |
| C | 26 | 10.6790 | 11.5245 | 10.8806 | 9.9836 | 10.3303 | 5.4261 |
| C | 27 | 11.8015 | 12.6615 | 11.8894 | 10.9461 | 11.1814 | 6.6332 |
| H | 28 | 12.1533 | 12.9575 | 12.2838 | 11.4209 | 11.6827 | 6.7629 |
| H | 29 | 11.5258 | 12.4236 | 11.4870 | 10.4831 | 10.6206 | 6.7351 |
| H | 30 | 12.7136 | 13.5947 | 12.7932 | 11.8051 | 12.0196 | 7.5888 |
| C | 31 | 7.8951 | 8.3216 | 8.8683 | 8.6486 | 9.5640 | 3.6983 |
| C | 32 | 6.8937 | 7.2887 | 7.8713 | 7.7375 | 8.6666 | 2.5561 |
| C | 33 | 6.9561 | 7.4461 | 7.7508 | 7.4981 | 8.3231 | 1.4151 |
| C | 34 | 8.2119 | 8.6603 | 8.9716 | 8.7164 | 9.4886 | 2.4271 |
| H | 35 | 9.0161 | 9.4085 | 9.8612 | 9.6481 | 10.4586 | 3.4202 |
| C | 36 | 8.6158 | 9.0875 | 9.2269 | 8.9276 | 9.5940 | 2.8282 |
| C | 37 | 7.8121 | 8.3438 | 8.2661 | 7.9173 | 8.4997 | 2.4185 |
| H | 38 | 8.3680 | 8.8955 | 8.6964 | 8.3301 | 8.8094 | 3.4155 |
| C | 39 | 15.3562 | 16.0596 | 15.7601 | 15.0077 | 15.4414 | 9.5009 |
| H | 40 | 14.9544 | 15.6370 | 15.3391 | 14.6204 | 15.0423 | 9.0548 |
| H | 41 | 15.4231 | 16.1849 | 15.7442 | 14.9077 | 15.2784 | 9.7090 |
| H | 42 | 16.3979 | 17.0802 | 16.8281 | 16.0950 | 16.5393 | 10.5051 |
| C | 43 | 6.7439 | 6.8120 | 8.0000 | 8.2339 | 9.2923 | 4.5651 |
| C | 44 | 7.7967 | 7.9416 | 9.0119 | 9.1211 | 10.1583 | 5.2650 |
| H | 45 | 8.4084 | 8.4664 | 9.6712 | 9.8542 | 10.9092 | 6.3567 |
| C | 46 | 8.3411 | 8.6499 | 9.4323 | 9.3359 | 10.3090 | 4.9499 |
| C | 47 | 11.7681 | 12.3958 | 12.4848 | 11.8856 | 12.5949 | 8.3839 |
| C | 48 | 12.1861 | 12.9183 | 12.7487 | 11.9951 | 12.5926 | 8.7287 |
| H | 49 | 11.4929 | 12.2737 | 11.9896 | 11.1785 | 11.7390 | 7.9039 |
| H | 50 | 12.3894 | 13.1385 | 12.9015 | 12.1180 | 12.6774 | 9.3998 |
| H | 51 | 13.1693 | 13.9051 | 13.7247 | 12.9507 | 13.5299 | 9.3903 |
| C | 52 | 14.8090 | 15.1802 | 15.8031 | 15.4935 | 16.3556 | 10.5046 |
| H | 53 | 14.2146 | 14.5431 | 15.2526 | 15.0033 | 15.8978 | 10.2659 |
| H | 54 | 15.5943 | 15.9199 | 16.6245 | 16.3631 | 17.2436 | 11.2118 |
| H | 55 | 15.3572 | 15.7803 | 16.3003 | 15.9180 | 16.7437 | 11.0992 |
| C | 56 | 5.1471 | 6.2223 | 4.3869 | 3.0209 | 2.7527 | 6.9165 |
| H | 57 | 4.9120 | 5.9188 | 4.0193 | 2.7819 | 2.3850 | 7.6557 |
| C | 58 | 6.5306 | 7.6135 | 5.7552 | 4.3686 | 3.9618 | 7.5518 |
| C | 59 | 7.1214 | 8.2249 | 6.4928 | 5.1021 | 4.8288 | 6.9495 |
| H | 60 | 8.2227 | 9.3257 | 7.5665 | 6.1691 | 5.8213 | 7.7133 |

Figure 2 - cont.

| | | | | | | | |
|---|---|---|---|---|---|---|---|
| C | 61 | 6.5921 | 7.6830 | 6.1720 | 4.8641 | 4.8395 | 5.5818 |
| C | 62 | 10.4679 | 11.3914 | 10.5831 | 9.5645 | 9.8511 | 5.8289 |
| H | 63 | 11.4591 | 12.3915 | 11.5705 | 10.5215 | 10.7854 | 6.8619 |
| H | 64 | 10.2378 | 11.2070 | 10.2082 | 9.1104 | 9.2850 | 6.0162 |
| H | 65 | 9.7442 | 10.6587 | 9.9359 | 8.9502 | 9.3153 | 5.2754 |
| C | 66 | 9.4779 | 10.2862 | 9.6882 | 8.8751 | 9.2539 | 4.1519 |
| H | 67 | 9.8746 | 10.6081 | 10.1387 | 9.4297 | 9.8362 | 4.2909 |
| H | 68 | 8.6250 | 9.4142 | 8.9372 | 8.1827 | 8.6610 | 3.2130 |
| H | 69 | 9.2148 | 10.0730 | 9.2692 | 8.3764 | 8.6420 | 4.3995 |
| C | 70 | 6.2550 | 6.4609 | 7.3954 | 7.5106 | 8.5213 | 3.1911 |
| H | 71 | 5.6595 | 5.7982 | 6.7945 | 7.0188 | 8.0235 | 2.9789 |
| C | 72 | 12.9408 | 13.5935 | 13.5402 | 12.8910 | 13.4961 | 7.3060 |
| H | 73 | 13.7429 | 14.3571 | 14.4038 | 13.7951 | 14.4353 | 8.1669 |
| C | 74 | 13.3895 | 14.0818 | 13.8838 | 13.1720 | 13.6949 | 7.6186 |
| C | 75 | 12.6198 | 13.3672 | 13.0024 | 12.2225 | 12.6725 | 6.9112 |
| H | 76 | 13.1585 | 13.9289 | 13.4537 | 12.6307 | 13.0067 | 7.4862 |
| C | 77 | 11.2844 | 12.0578 | 11.6563 | 10.8612 | 11.3250 | 5.7166 |
| C | 78 | 10.4894 | 11.0960 | 11.2287 | 10.6851 | 11.4275 | 7.7455 |
| H | 79 | 10.3897 | 10.8984 | 11.2435 | 10.8329 | 11.6489 | 7.8419 |
| H | 80 | 10.6950 | 11.3280 | 11.3650 | 10.7782 | 11.4721 | 8.4556 |
| H | 81 | 9.5869 | 10.2401 | 10.2867 | 9.7039 | 10.4361 | 6.7283 |
| O | 82 | 5.0576 | 6.0550 | 5.0619 | 4.1046 | 4.5688 | 3.3423 |
| O | 83 | 3.6720 | 4.5540 | 4.2096 | 3.7031 | 4.5963 | 3.8828 |
| O | 84 | 4.7838 | 5.4670 | 5.4214 | 5.0708 | 5.9002 | 1.3965 |
| H | 85 | 8.4596 | 9.5073 | 7.5045 | 6.1565 | 5.4794 | 9.5633 |
| H | 86 | 2.9396 | 2.9377 | 2.1826 | 3.2204 | 3.4204 | 7.9123 |
| O | 87 | 9.3906 | 10.1388 | 9.8993 | 9.1892 | 9.7909 | 4.1591 |
| O | 88 | 10.0949 | 10.8086 | 10.7162 | 10.0371 | 10.7060 | 5.8312 |
| O | 89 | 8.7747 | 9.3187 | 9.6091 | 9.2058 | 10.0291 | 4.0431 |
| O | 90 | 14.0955 | 14.5053 | 15.0468 | 14.6990 | 15.5365 | 9.4302 |
| O | 91 | 14.7046 | 15.3784 | 15.2031 | 14.4999 | 15.0112 | 8.8663 |
| C | 92 | 11.6354 | 12.2390 | 12.3690 | 11.8097 | 12.5266 | 6.5773 |
| C | 93 | 12.5812 | 13.1020 | 13.4075 | 12.9412 | 13.7083 | 7.5238 |
| C | 94 | 13.0906 | 13.5696 | 13.9787 | 13.5572 | 14.3619 | 8.4449 |
| C | 95 | 12.7647 | 13.2784 | 13.6249 | 13.1623 | 13.9536 | 8.5755 |
| C | 96 | 11.7810 | 12.3713 | 12.5577 | 12.0111 | 12.7587 | 7.7391 |

Figure 2 - cont.

|   |     |         |         |         |         |         |        |
|---|-----|---------|---------|---------|---------|---------|--------|
| C | 97  | 11.1046 | 11.7394 | 11.8247 | 11.2328 | 11.9504 | 6.6098 |
| H | 98  | 13.0870 | 13.5769 | 13.9226 | 13.4891 | 14.2556 | 7.7728 |
| H | 99  | 13.3957 | 13.8776 | 14.2861 | 13.8538 | 14.6600 | 9.5043 |
| H | 100 | 3.3223  | 3.5783  | 4.5400  | 4.8533  | 5.9331  | 3.7978 |
| H | 101 | 7.9141  | 8.9454  | 7.5295  | 6.3241  | 6.2612  | 5.4914 |
| C | 102 | 9.6446  | 9.9812  | 10.7046 | 10.5333 | 11.4771 | 6.2245 |
| H | 103 | 9.6793  | 10.1123 | 10.6496 | 10.3577 | 11.2516 | 6.3714 |
| H | 104 | 10.0169 | 10.2630 | 11.1458 | 11.0722 | 12.0506 | 7.0974 |
| H | 105 | 10.4630 | 10.8108 | 11.5016 | 11.2969 | 12.2190 | 6.4896 |
| C | 106 | 6.5354  | 6.3607  | 7.8960  | 8.3783  | 9.4711  | 5.5883 |
| H | 107 | 5.9147  | 5.7067  | 7.2962  | 7.8298  | 8.9318  | 5.9330 |
| H | 108 | 6.2650  | 5.9989  | 7.6186  | 8.1999  | 9.2790  | 5.4398 |
| H | 109 | 7.5545  | 7.3103  | 8.9333  | 9.4519  | 10.5486 | 6.5460 |
| C | 110 | 5.9220  | 6.5970  | 6.0791  | 5.6219  | 6.0857  | 2.5507 |
| H | 111 | 4.9165  | 5.5420  | 5.1099  | 4.8170  | 5.3613  | 2.8015 |
| H | 112 | 6.6847  | 7.2960  | 6.7478  | 6.3336  | 6.6868  | 3.4584 |
| H | 113 | 6.0007  | 6.8163  | 5.9838  | 5.2837  | 5.6303  | 2.9591 |
| C | 114 | 10.0718 | 10.5052 | 10.6701 | 10.3770 | 11.0061 | 4.3404 |
| H | 115 | 10.7240 | 11.2378 | 11.2548 | 10.8386 | 11.4143 | 4.8320 |
| H | 116 | 10.5260 | 10.8805 | 11.2399 | 11.0362 | 11.7343 | 4.8727 |
| H | 117 | 10.3023 | 10.7019 | 10.8333 | 10.5794 | 11.1556 | 4.8701 |
| C | 118 | 7.6779  | 8.7343  | 7.3747  | 6.1388  | 6.1631  | 5.3725 |
| H | 119 | 8.6400  | 9.7113  | 8.3047  | 7.0213  | 6.9772  | 6.3060 |
| H | 120 | 7.5794  | 8.5918  | 7.4794  | 6.3568  | 6.5638  | 4.5176 |
| C | 121 | 7.5887  | 8.6287  | 6.6863  | 5.3607  | 4.7695  | 9.0630 |
| H | 122 | 7.3318  | 8.3141  | 6.3088  | 5.0774  | 4.3606  | 9.5391 |
| H | 123 | 8.0711  | 9.1002  | 7.2817  | 5.9975  | 5.5293  | 9.4755 |
| C | 124 | 2.5483  | 2.7469  | 3.8547  | 4.3281  | 5.4307  | 4.7735 |
| H | 125 | 3.2503  | 3.4734  | 4.4711  | 4.8199  | 5.9012  | 5.2747 |
| H | 126 | 2.6569  | 2.3857  | 4.0671  | 4.8481  | 5.9320  | 5.5084 |
| C | 127 | 2.5423  | 2.7463  | 1.5137  | 2.5446  | 2.7522  | 7.9446 |
| H | 128 | 2.8104  | 2.6841  | 2.1830  | 3.3440  | 3.6268  | 8.6394 |
| H | 129 | 3.4636  | 3.8162  | 2.1824  | 2.6661  | 2.4112  | 8.5442 |
| H | 130 | 6.3953  | 7.0381  | 7.1857  | 6.7584  | 7.6190  | 3.6684 |

| | | | | | | | |
|---|---|---|---|---|---|---|---|
| H | 60 | 7.7152 | 7.3840 | 7.9001 | 8.7807 | 7.1885 | 8.3235 |
| C | 61 | 5.6562 | 6.2305 | 7.0166 | 7.7802 | 6.4488 | 7.6503 |
| C | 62 | 5.8392 | 1.5510 | 2.4871 | 3.4881 | 2.6974 | 2.7487 |
| H | 63 | 6.9217 | 2.2070 | 2.7519 | 3.7936 | 3.0873 | 2.5446 |
| H | 64 | 5.8758 | 2.1980 | 2.6949 | 3.7288 | 2.4256 | 3.0409 |
| H | 65 | 5.5336 | 2.2147 | 3.4776 | 4.3822 | 3.7113 | 3.7943 |
| C | 66 | 3.7567 | 1.5481 | 2.4853 | 2.7499 | 2.6903 | 3.4865 |
| H | 67 | 3.6906 | 2.2005 | 2.7383 | 2.5326 | 3.0629 | 3.7831 |
| H | 68 | 3.1165 | 2.2191 | 3.4802 | 3.7926 | 3.7126 | 4.3869 |
| H | 69 | 3.7994 | 2.1935 | 2.6932 | 3.0473 | 2.4173 | 3.7240 |
| C | 70 | 4.4158 | 7.7654 | 9.1487 | 9.2565 | 9.4838 | 9.9625 |
| H | 71 | 4.0013 | 8.0521 | 9.3504 | 9.4001 | 9.5945 | 10.2433 |
| C | 72 | 7.6488 | 4.3695 | 5.1259 | 5.1723 | 6.1896 | 5.0517 |
| H | 73 | 8.5804 | 5.4602 | 6.1634 | 6.1733 | 7.2402 | 6.0092 |
| C | 74 | 7.7110 | 3.8638 | 4.2270 | 4.1322 | 5.3349 | 4.0594 |
| C | 75 | 6.8491 | 2.5572 | 2.8310 | 2.8080 | 3.9366 | 2.7837 |
| H | 76 | 7.2355 | 2.7321 | 2.3669 | 2.1460 | 3.4540 | 2.1736 |
| C | 77 | 5.7575 | 1.5536 | 2.5724 | 2.8814 | 3.5241 | 2.8632 |
| C | 78 | 8.9650 | 7.9855 | 9.4207 | 10.0811 | 9.9517 | 9.5334 |
| H | 79 | 9.1354 | 8.6575 | 10.1312 | 10.7166 | 10.6879 | 10.3102 |
| H | 80 | 9.6719 | 8.6384 | 10.0413 | 10.7786 | 10.4992 | 10.1122 |
| H | 81 | 7.9307 | 7.1246 | 8.5943 | 9.2648 | 9.0676 | 8.7897 |
| O | 82 | 3.6111 | 5.9009 | 6.9605 | 7.4940 | 6.6330 | 7.7974 |
| O | 83 | 4.8192 | 7.6527 | 8.9512 | 9.4729 | 8.8256 | 9.7250 |
| O | 84 | 2.4151 | 6.2065 | 7.4601 | 7.7427 | 7.4482 | 8.3726 |
| H | 85 | 9.5840 | 9.9111 | 10.4041 | 11.2506 | 9.6383 | 10.8356 |
| H | 86 | 7.9207 | 12.3038 | 13.1777 | 13.4474 | 12.7129 | 14.1498 |
| O | 87 | 4.7301 | 2.8527 | 4.3792 | 4.8384 | 4.9754 | 4.8640 |
| O | 88 | 6.7779 | 4.9753 | 6.4141 | 7.0132 | 7.0341 | 6.5831 |
| O | 89 | 5.1418 | 5.3402 | 6.8348 | 7.1186 | 7.4430 | 7.3515 |
| O | 90 | 10.3187 | 8.7755 | 9.8625 | 9.9671 | 10.8459 | 9.8570 |
| O | 91 | 8.8849 | 5.0127 | 5.0609 | 4.8043 | 6.1630 | 4.7353 |
| C | 92 | 7.3519 | 5.2400 | 6.4731 | 6.7533 | 7.3688 | 6.5687 |
| C | 93 | 8.3063 | 6.4294 | 7.5554 | 7.7015 | 8.5173 | 7.6120 |
| C | 94 | 9.3617 | 7.6729 | 8.8388 | 9.0485 | 9.7765 | 8.8477 |
| C | 95 | 9.6045 | 7.9080 | 9.1591 | 9.5254 | 10.0154 | 9.1401 |

Figure 2 - cont.

| | | | | | | |
|---|---|---|---|---|---|---|
| C 96 | 8.7849 | 7.0199 | 8.3428 | 8.8318 | 9.1081 | 8.3534 |
| C 97 | 7.5521 | 5.6487 | 6.9988 | 7.4621 | 7.7693 | 7.0858 |
| H 98 | 8.4263 | 6.5665 | 7.5585 | 7.5491 | 8.5735 | 7.6273 |
| H 99 | 10.5863 | 8.9620 | 10.2070 | 10.5951 | 11.0543 | 10.1512 |
| H 100 | 4.8127 | 8.8868 | 10.2068 | 10.4742 | 10.2333 | 11.0861 |
| H 101 | 5.1092 | 4.9016 | 5.3382 | 6.0214 | 4.5949 | 6.0435 |
| C 102 | 7.5020 | 8.0746 | 9.5590 | 9.8448 | 10.2131 | 9.9634 |
| H 103 | 7.6585 | 7.7557 | 9.2573 | 9.6588 | 9.8832 | 9.5892 |
| H 104 | 8.4059 | 9.1842 | 10.6685 | 10.9484 | 11.3216 | 11.0630 |
| H 105 | 7.6551 | 7.8145 | 9.2336 | 9.4421 | 9.9813 | 9.5885 |
| C 106 | 6.7357 | 10.2751 | 11.6807 | 11.7892 | 12.0183 | 12.4699 |
| H 107 | 7.1213 | 10.6882 | 12.1204 | 12.3118 | 12.3922 | 12.9027 |
| H 108 | 6.4216 | 10.4082 | 11.7436 | 11.7783 | 12.0350 | 12.5985 |
| H 109 | 7.6846 | 11.0170 | 12.4285 | 12.5069 | 12.8338 | 13.1811 |
| C 110 | 1.5101 | 5.9177 | 6.6776 | 6.7323 | 6.4010 | 7.7470 |
| H 111 | 2.1759 | 6.9090 | 7.7408 | 7.8278 | 7.4579 | 8.7955 |
| H 112 | 2.1668 | 6.2176 | 6.7509 | 6.6646 | 6.4132 | 7.8503 |
| H 113 | 2.1791 | 5.5018 | 6.2416 | 6.4540 | 5.8472 | 7.2680 |
| C 114 | 3.8537 | 5.1751 | 5.7709 | 5.1938 | 6.2722 | 6.6653 |
| H 115 | 4.3501 | 4.3964 | 4.8663 | 4.2272 | 5.4706 | 5.6949 |
| H 116 | 4.6217 | 5.9237 | 6.5854 | 6.0029 | 7.1899 | 7.3956 |
| H 117 | 4.1095 | 5.8030 | 6.1872 | 5.4990 | 6.5666 | 7.1251 |
| C 118 | 5.2823 | 4.8739 | 5.5494 | 6.3455 | 4.9561 | 6.1659 |
| H 119 | 6.2540 | 4.9341 | 5.4827 | 6.3987 | 4.8647 | 5.9165 |
| H 120 | 4.5478 | 4.0595 | 4.9644 | 5.7354 | 4.5589 | 5.6328 |
| C 121 | 9.2147 | 9.8908 | 10.5382 | 11.3790 | 9.8519 | 11.0145 |
| H 122 | 9.6846 | 10.8017 | 11.4657 | 12.2646 | 10.7679 | 11.9919 |
| H 123 | 9.7588 | 10.1251 | 10.8344 | 11.7355 | 10.2132 | 11.2312 |
| C 124 | 5.7180 | 9.7211 | 11.0330 | 11.3578 | 10.9949 | 11.8975 |
| H 125 | 6.3737 | 9.9100 | 11.2914 | 11.6876 | 11.3008 | 12.0864 |
| H 126 | 6.3661 | 10.6537 | 11.9453 | 12.2080 | 11.9147 | 12.8387 |
| C 127 | 8.0923 | 12.1975 | 13.1273 | 13.4841 | 12.6639 | 14.0530 |
| H 128 | 8.9044 | 13.0544 | 14.0463 | 14.4139 | 13.6226 | 14.9609 |
| H 129 | 8.6086 | 12.4353 | 13.2893 | 13.6886 | 12.7464 | 14.1885 |
| H 130 | 5.0053 | 6.4571 | 7.9732 | 8.4767 | 8.2234 | 8.5865 |

Figure 2 - cont.

|      | C 31    | C 32    | C 33   | C 34   | H 35    | C 36   |
|------|---------|---------|--------|--------|---------|--------|
| C 31 | 0.0000  |         |        |        |         |        |
| C 32 | 1.4146  | 0.0000  |        |        |         |        |
| C 33 | 2.5649  | 1.4956  | 0.0000 |        |         |        |
| C 34 | 3.2237  | 2.4940  | 1.4123 | 0.0000 |         |        |
| H 35 | 3.0166  | 2.6682  | 2.1638 | 1.1023 | 0.0000  |        |
| C 36 | 4.6054  | 3.7959  | 2.4641 | 1.4055 | 2.1744  | 0.0000 |
| C 37 | 5.2957  | 4.2846  | 2.8109 | 2.4101 | 3.4149  | 1.4093 |
| H 38 | 6.3911  | 5.3836  | 3.9145 | 3.4128 | 4.3306  | 2.1735 |
| C 39 | 9.2140  | 9.6277  | 8.8917 | 7.9205 | 7.6295  | 7.6450 |
| H 40 | 9.1201  | 9.3754  | 8.5109 | 7.4581 | 7.2383  | 7.0126 |
| H 41 | 9.5637  | 9.9834  | 9.2165 | 8.3605 | 8.1751  | 8.0736 |
| H 42 | 10.0687 | 10.5249 | 9.8368 | 8.8136 | 8.4433  | 8.5447 |
| C 43 | 2.8321  | 2.4681  | 3.8002 | 4.6489 | 4.5701  | 5.8919 |
| C 44 | 2.4227  | 2.8147  | 4.2970 | 5.0258 | 4.7220  | 6.3907 |
| H 45 | 3.4186  | 3.9184  | 5.3982 | 6.0791 | 5.6946  | 7.4445 |
| C 46 | 1.4171  | 2.4665  | 3.8508 | 4.4677 | 4.0820  | 5.8720 |
| C 47 | 5.5507  | 6.8639  | 7.6004 | 8.0125 | 7.6571  | 9.1326 |
| C 48 | 6.4131  | 7.6106  | 8.1102 | 8.4975 | 8.2625  | 9.4639 |
| H 49 | 5.9643  | 7.0444  | 7.3909 | 7.7961 | 7.6710  | 8.6824 |
| H 50 | 7.1738  | 8.3356  | 8.8786 | 9.3781 | 9.2030  | 10.3523 |
| H 51 | 7.0708  | 8.2910  | 8.7114 | 8.9414 | 8.6340  | 9.8418 |
| C 52 | 7.1198  | 8.4251  | 9.2184 | 8.9711 | 8.0578  | 10.0500 |
| H 53 | 6.7204  | 8.0439  | 8.9879 | 8.8829 | 7.9968  | 10.0593 |
| H 54 | 7.8629  | 9.1065  | 9.8810 | 9.5307 | 8.5545  | 10.5654 |
| H 55 | 7.7601  | 9.1090  | 9.8707 | 9.6683 | 8.8094  | 10.7259 |
| C 56 | 8.9372  | 8.3695  | 8.0546 | 9.2214 | 10.1253 | 9.4369 |
| H 57 | 9.5939  | 9.0013  | 8.7870 | 10.0078| 10.9025 | 10.2641 |
| C 58 | 9.5274  | 9.0709  | 8.6614 | 9.7302 | 10.6252 | 9.8729 |
| C 59 | 8.9631  | 8.5615  | 8.0173 | 8.9622 | 9.8473  | 9.0316 |
| H 60 | 9.6469  | 9.3274  | 8.7314 | 9.5810 | 10.4416 | 9.5904 |
| C 61 | 7.7209  | 7.2682  | 6.6465 | 7.5615 | 8.4574  | 7.6277 |
| C 62 | 6.6181  | 6.7705  | 5.9626 | 5.9842 | 6.4215  | 5.9596 |
| H 63 | 7.2767  | 7.5914  | 6.8863 | 6.8502 | 7.1676  | 6.8713 |
| H 64 | 7.2977  | 7.2947  | 6.3956 | 6.5159 | 7.0936  | 6.3604 |

Figure 2 - cont.

| | | | | | | |
|---|---|---|---|---|---|---|
| H 65 | 5.7683 | 5.9975 | 5.3599 | 5.5811 | 6.0039 | 5.7938 |
| C 66 | 5.8759 | 5.5856 | 4.3746 | 4.1089 | 4.7523 | 3.6759 |
| H 67 | 6.0992 | 5.7129 | 4.3969 | 3.8090 | 4.4108 | 3.0774 |
| H 68 | 4.8530 | 4.5421 | 3.3959 | 3.3604 | 4.0568 | 3.2381 |
| H 69 | 6.6260 | 6.2026 | 4.9386 | 4.8406 | 5.6190 | 4.2835 |
| C 70 | 2.4261 | 1.4130 | 2.4894 | 3.4502 | 3.6133 | 4.6172 |
| H 71 | 3.4180 | 2.1621 | 2.6525 | 3.5806 | 3.9565 | 4.4906 |
| C 72 | 5.9792 | 6.7191 | 6.4117 | 5.7212 | 5.2328 | 6.0896 |
| H 73 | 6.4540 | 7.3169 | 7.1665 | 6.4575 | 5.8271 | 6.9100 |
| C 74 | 6.9254 | 7.4638 | 6.8949 | 6.0854 | 5.7494 | 6.1368 |
| C 75 | 6.8576 | 7.2009 | 6.4210 | 5.6918 | 5.6136 | 5.5563 |
| H 76 | 7.8161 | 8.0467 | 7.1354 | 6.3634 | 6.3798 | 6.0097 |
| C 77 | 5.8290 | 6.1154 | 5.3260 | 4.8219 | 4.9091 | 4.8150 |
| C 78 | 4.9772 | 6.1998 | 7.0790 | 7.7422 | 7.5125 | 8.9348 |
| H 79 | 4.7528 | 6.0099 | 7.0765 | 7.7576 | 7.4488 | 9.0383 |
| H 80 | 5.9115 | 7.0516 | 7.9169 | 8.6704 | 8.5141 | 9.8359 |
| H 81 | 4.2576 | 5.3739 | 6.1546 | 6.8894 | 6.7753 | 8.0429 |
| O 82 | 5.8628 | 5.1456 | 4.5146 | 5.5713 | 6.5147 | 5.7552 |
| O 83 | 5.1462 | 4.5230 | 4.6520 | 6.0287 | 6.7596 | 6.6918 |
| O 84 | 4.0052 | 2.9353 | 2.4365 | 3.7105 | 4.5954 | 4.2242 |
| H 85 | 11.5664 | 11.1634 | 10.6827 | 11.6652 | 12.5666 | 11.6985 |
| H 86 | 10.4727 | 9.3229 | 9.0666 | 10.1357 | 11.0577 | 10.1917 |
| O 87 | 3.7328 | 4.1290 | 3.6676 | 3.7147 | 3.8751 | 4.3012 |
| O 88 | 3.8106 | 4.8561 | 5.1537 | 5.4918 | 5.3444 | 6.4499 |
| O 89 | 1.3916 | 2.4425 | 2.9648 | 3.3066 | 3.0451 | 4.5518 |
| O 90 | 6.2563 | 7.5041 | 8.1411 | 7.7787 | 6.8611 | 8.7844 |
| O 91 | 8.1246 | 8.6755 | 8.1099 | 7.1888 | 6.7735 | 7.1476 |
| C 92 | 4.2301 | 5.3293 | 5.5381 | 5.2887 | 4.7297 | 6.1725 |
| C 93 | 4.8362 | 5.9898 | 6.3369 | 5.9392 | 5.1644 | 6.8492 |
| C 94 | 5.3378 | 6.6337 | 7.2336 | 6.9933 | 6.1902 | 8.0265 |
| C 95 | 5.3597 | 6.7438 | 7.4710 | 7.4845 | 6.8125 | 8.5992 |
| C 96 | 4.7712 | 6.1240 | 6.7855 | 6.9733 | 6.4833 | 8.0763 |
| C 97 | 4.0413 | 5.2689 | 5.6900 | 5.7906 | 5.3777 | 6.8018 |
| H 98 | 5.3258 | 6.3339 | 6.5447 | 5.9182 | 5.0541 | 6.6954 |
| H 99 | 6.1546 | 7.5621 | 8.4002 | 8.4722 | 7.7829 | 9.6272 |
| H 100 | 4.7594 | 3.7650 | 4.2167 | 5.5141 | 6.1056 | 6.2875 |

Figure 2 - cont.

| | | | | | | |
|---|---|---|---|---|---|---|
| H 101 | 8.0353 | 7.5238 | 6.5392 | 7.0877 | 8.0167 | 6.8013 |
| C 102 | 2.5388 | 3.8430 | 5.0899 | 5.5275 | 4.9780 | 6.9096 |
| H 103 | 2.8680 | 4.2278 | 5.3709 | 5.9092 | 5.4759 | 7.2521 |
| H 104 | 3.4608 | 4.6318 | 5.9822 | 6.4502 | 5.8714 | 7.8456 |
| H 105 | 2.8585 | 4.1749 | 5.2348 | 5.3868 | 4.6674 | 6.7124 |
| C 106 | 4.3447 | 3.8556 | 5.0263 | 5.8595 | 5.8272 | 6.9789 |
| H 107 | 4.8434 | 4.3899 | 5.5633 | 6.5688 | 6.6411 | 7.6787 |
| H 108 | 4.8735 | 4.0982 | 5.0077 | 5.7620 | 5.8276 | 6.7201 |
| H 109 | 4.8726 | 4.6029 | 5.8393 | 6.5248 | 6.3268 | 7.6791 |
| C 110 | 6.2416 | 5.0875 | 3.8547 | 4.3336 | 5.4350 | 3.8504 |
| H 111 | 6.4046 | 5.1568 | 4.1451 | 4.8381 | 5.9106 | 4.5470 |
| H 112 | 7.1167 | 5.9477 | 4.6247 | 4.8291 | 5.9094 | 4.0438 |
| H 113 | 6.4785 | 5.4731 | 4.2956 | 4.8726 | 5.9613 | 4.4694 |
| C 114 | 5.6371 | 5.0238 | 3.8504 | 2.5410 | 2.7544 | 1.5127 |
| H 115 | 5.9321 | 5.5206 | 4.3501 | 3.0749 | 3.2024 | 2.1774 |
| H 116 | 5.5224 | 5.0220 | 4.1075 | 2.7151 | 2.5061 | 2.1827 |
| H 117 | 6.6082 | 5.8571 | 4.6139 | 3.4215 | 3.7520 | 2.1827 |
| C 118 | 7.5036 | 7.1282 | 6.3231 | 7.0052 | 7.8702 | 6.9385 |
| H 119 | 8.1065 | 7.8874 | 7.1375 | 7.7568 | 8.5481 | 7.7109 |
| H 120 | 6.4707 | 6.1460 | 5.3430 | 5.9978 | 6.8208 | 6.0178 |
| C 121 | 10.9218 | 10.5230 | 10.1574 | 11.2288 | 12.1106 | 11.3694 |
| H 122 | 11.4863 | 11.0099 | 10.6801 | 11.7986 | 12.7034 | 11.9390 |
| H 123 | 10.9800 | 10.7142 | 10.4679 | 11.5691 | 12.3874 | 11.8165 |
| C 124 | 5.6858 | 4.8042 | 5.2862 | 6.6059 | 7.2050 | 7.3504 |
| H 125 | 5.5318 | 4.9045 | 5.6200 | 6.9813 | 7.4779 | 7.8716 |
| H 126 | 6.3748 | 5.4429 | 5.9590 | 7.1929 | 7.7478 | 7.9056 |
| C 127 | 10.2939 | 9.2438 | 9.0844 | 10.2471 | 11.1529 | 10.4083 |
| H 128 | 10.7026 | 9.6972 | 9.6875 | 10.8905 | 11.7403 | 11.1483 |
| H 129 | 11.0091 | 9.9910 | 9.7527 | 10.9041 | 11.8484 | 11.0000 |
| H 130 | 2.5463 | 2.7397 | 3.4470 | 4.6587 | 4.9701 | 5.7667 |

| | C 37 | H 38 | C 39 | H 40 | H 41 | H 42 |
|---|---|---|---|---|---|---|
| C 37 | 0.0000 | | | | | |
| H 38 | 1.1042 | 0.0000 | | | | |
| C 39 | 8.4248 | 8.5270 | 0.0000 | | | |

Figure 2 - cont.

| | | | | | | |
|---|---|---|---|---|---|---|
| H | 40 | 7.7450 | 7.7420 | 1.1167 | 0.0000 | |
| H | 41 | 8.7162 | 8.7988 | 1.1167 | 1.8161 | 0.0000 |
| H | 42 | 9.3826 | 9.4631 | 1.1091 | 1.8111 | 1.8109 | 0.0000 |
| C | 43 | 6.3493 | 7.3907 | 11.7889 | 11.5804 | 12.2199 | 12.6091 |
| C | 44 | 7.0278 | 8.1093 | 11.3962 | 11.3150 | 11.8258 | 12.1718 |
| H | 45 | 8.1142 | 9.1898 | 12.1822 | 12.1541 | 12.6332 | 12.9110 |
| C | 46 | 6.6115 | 7.7066 | 10.1608 | 10.1496 | 10.5528 | 10.9427 |
| C | 47 | 9.8089 | 10.7732 | 9.4346 | 9.9666 | 9.4365 | 10.1055 |
| C | 48 | 10.0268 | 10.9105 | 9.0286 | 9.6259 | 8.8536 | 9.7252 |
| H | 49 | 9.1556 | 10.0063 | 8.4951 | 9.0162 | 8.2706 | 9.2796 |
| H | 50 | 10.8287 | 11.7148 | 10.0047 | 10.6157 | 9.7611 | 10.7027 |
| H | 51 | 10.4815 | 11.3191 | 8.5160 | 9.2142 | 8.3240 | 9.1263 |
| C | 52 | 11.2460 | 12.1426 | 9.2915 | 9.8543 | 9.8060 | 9.5017 |
| H | 53 | 11.2124 | 12.1646 | 10.0632 | 10.5689 | 10.5590 | 10.3545 |
| H | 54 | 11.8220 | 12.6870 | 9.6354 | 10.1828 | 10.2347 | 9.7402 |
| H | 55 | 11.8766 | 12.7649 | 9.3904 | 10.0566 | 9.8088 | 9.5729 |
| C | 56 | 8.4859 | 8.9006 | 14.1118 | 13.8698 | 13.8045 | 15.2168 |
| H | 57 | 9.3056 | 9.7280 | 15.1719 | 14.9275 | 14.8818 | 16.2755 |
| C | 58 | 8.9296 | 9.2794 | 13.8293 | 13.6312 | 13.4174 | 14.9312 |
| C | 59 | 8.1260 | 8.4442 | 12.5223 | 12.3306 | 12.0767 | 13.6218 |
| H | 60 | 8.7111 | 8.9672 | 12.4240 | 12.2705 | 11.8890 | 13.5094 |
| C | 61 | 6.7484 | 7.1150 | 11.4300 | 11.1959 | 11.0666 | 12.5364 |
| C | 62 | 5.9045 | 6.2748 | 6.2073 | 6.1761 | 5.7591 | 7.2923 |
| H | 63 | 6.9260 | 7.2837 | 5.8644 | 6.0077 | 5.2755 | 6.8993 |
| H | 64 | 6.0592 | 6.3124 | 7.0036 | 6.8888 | 6.4857 | 8.0877 |
| H | 65 | 5.7811 | 6.3247 | 6.8116 | 6.8293 | 6.4631 | 7.8863 |
| C | 66 | 3.5016 | 3.7638 | 6.2369 | 5.7942 | 6.1479 | 7.3295 |
| H | 67 | 3.0282 | 3.1220 | 5.9174 | 5.3116 | 5.9796 | 6.9659 |
| H | 68 | 3.1209 | 3.6865 | 6.8345 | 6.4631 | 6.8243 | 7.9162 |
| H | 69 | 3.7423 | 3.8117 | 7.0315 | 6.5489 | 6.8361 | 8.1231 |
| C | 70 | 4.9687 | 6.0111 | 10.9444 | 10.6524 | 11.3416 | 11.8164 |
| H | 71 | 4.6175 | 5.5728 | 11.3969 | 11.0082 | 11.7938 | 12.2862 |
| C | 72 | 7.0799 | 7.6441 | 3.6502 | 4.0501 | 4.0326 | 4.3733 |
| H | 73 | 7.9912 | 8.5766 | 3.9265 | 4.4810 | 4.4168 | 4.4027 |
| C | 74 | 7.0092 | 7.3865 | 2.3931 | 2.7366 | 2.7434 | 3.2853 |
| C | 75 | 6.1968 | 6.4870 | 2.8477 | 2.8443 | 2.8527 | 3.9322 |

Figure 2 - cont.

| | | | | | | | |
|---|---|---|---|---|---|---|---|
| H | 76 | 6.5114 | 6.6242 | 2.5333 | 2.3421 | 2.3293 | 3.6343 |
| C | 77 | 5.3218 | 5.7478 | 4.2573 | 4.1856 | 4.1956 | 5.3374 |
| C | 78 | 9.4755 | 10.4892 | 10.3866 | 10.7965 | 10.3908 | 11.1457 |
| H | 79 | 9.6429 | 10.6970 | 10.9346 | 11.3080 | 11.0366 | 11.6639 |
| H | 80 | 10.2788 | 11.2793 | 11.2061 | 11.6468 | 11.1292 | 11.9727 |
| H | 81 | 8.4949 | 9.5004 | 9.9643 | 10.2853 | 9.9504 | 10.7974 |
| O | 82 | 4.8947 | 5.4556 | 10.9469 | 10.6152 | 10.8181 | 12.0409 |
| O | 83 | 6.1525 | 6.9655 | 12.3372 | 12.1058 | 12.3250 | 13.3870 |
| O | 84 | 3.6882 | 4.5714 | 10.6035 | 10.2250 | 10.7300 | 11.6315 |
| H | 85 | 10.7102 | 10.9342 | 14.9710 | 14.8021 | 14.4284 | 16.0563 |
| H | 86 | 9.1278 | 9.3633 | 17.0850 | 16.5532 | 17.1134 | 18.1383 |
| O | 87 | 4.7736 | 5.5744 | 6.4082 | 6.3775 | 6.4471 | 7.4234 |
| O | 88 | 7.0293 | 7.9413 | 7.5868 | 7.8799 | 7.5875 | 8.4574 |
| O | 89 | 5.3174 | 6.3566 | 8.0166 | 8.0099 | 8.3078 | 8.8859 |
| O | 90 | 10.0006 | 10.8593 | 8.0068 | 8.5137 | 8.5579 | 8.2721 |
| O | 91 | 8.0655 | 8.3445 | 1.4146 | 2.1047 | 2.1049 | 2.0260 |
| C | 92 | 7.1493 | 7.9889 | 6.0986 | 6.4522 | 6.3885 | 6.8040 |
| C | 93 | 7.9824 | 8.8116 | 6.3394 | 6.7486 | 6.8006 | 6.8552 |
| C | 94 | 9.1474 | 10.0332 | 7.5387 | 8.0345 | 7.9688 | 7.9647 |
| C | 95 | 9.5869 | 10.5256 | 8.3736 | 8.9132 | 8.6503 | 8.8732 |
| C | 96 | 8.9087 | 9.8570 | 8.2710 | 8.7639 | 8.4110 | 8.9143 |
| C | 97 | 7.6114 | 8.5242 | 7.2423 | 7.6308 | 7.3803 | 7.9889 |
| H | 98 | 7.9245 | 8.6774 | 5.8105 | 6.1676 | 6.4250 | 6.2328 |
| H | 99 | 10.6129 | 11.5704 | 9.3007 | 9.8907 | 9.5680 | 9.7371 |
| H | 100 | 5.9499 | 6.8141 | 12.9918 | 12.6571 | 13.2089 | 13.9670 |
| H | 101 | 5.8554 | 5.9628 | 10.0320 | 9.6855 | 9.6340 | 11.1326 |
| C | 102 | 7.7608 | 8.8389 | 10.0197 | 10.1671 | 10.4041 | 10.7231 |
| H | 103 | 8.0077 | 9.0810 | 9.9049 | 10.1278 | 10.1789 | 10.6415 |
| H | 104 | 8.6961 | 9.7798 | 10.9909 | 11.1616 | 11.4028 | 11.6477 |
| H | 105 | 7.7157 | 8.7523 | 9.2206 | 9.3953 | 9.6750 | 9.8601 |
| C | 106 | 7.3201 | 8.2907 | 13.2199 | 12.9709 | 13.6771 | 14.0260 |
| H | 107 | 7.8778 | 8.8486 | 13.9209 | 13.6986 | 14.3121 | 14.7629 |
| H | 108 | 6.9671 | 7.8568 | 13.3971 | 13.0579 | 13.8781 | 14.2089 |
| H | 109 | 8.1559 | 9.1243 | 13.6252 | 13.4120 | 14.1392 | 14.3729 |
| C | 110 | 2.5394 | 2.7253 | 10.3386 | 9.7178 | 10.4233 | 11.3726 |
| H | 111 | 3.3357 | 3.5997 | 11.3550 | 10.7526 | 11.4600 | 12.3850 |

Figure 2 - cont.

| | | | | | | |
|---|---|---|---|---|---|---|
| H 112 | 2.6381 | 2.3580 | 10.3967 | 9.6807 | 10.4960 | 11.4036 |
| H 113 | 3.2240 | 3.4030 | 10.2570 | 9.6979 | 10.2247 | 11.3255 |
| C 114 | 2.5456 | 2.7513 | 6.8826 | 6.1356 | 7.4482 | 7.6782 |
| H 115 | 3.0905 | 3.2136 | 5.8091 | 5.0500 | 6.3494 | 6.6320 |
| H 116 | 3.4221 | 3.7447 | 7.0277 | 6.3401 | 7.7211 | 7.7237 |
| H 117 | 2.7148 | 2.4962 | 7.4355 | 6.5745 | 7.9914 | 8.1923 |
| C 118 | 6.1327 | 6.4261 | 10.0567 | 9.8167 | 9.6524 | 11.1613 |
| H 119 | 7.0032 | 7.2804 | 9.9611 | 9.8111 | 9.4475 | 11.0494 |
| H 120 | 5.3476 | 5.7634 | 9.2579 | 9.0295 | 8.9306 | 10.3649 |
| C 121 | 10.4191 | 10.7347 | 15.0056 | 14.8479 | 14.5230 | 16.0987 |
| H 122 | 10.9385 | 11.2400 | 15.9590 | 15.7662 | 15.5086 | 17.0580 |
| H 123 | 10.9633 | 11.3566 | 15.1475 | 15.0703 | 14.6412 | 16.2274 |
| C 124 | 6.9275 | 7.7421 | 13.9785 | 13.6628 | 14.1524 | 14.9680 |
| H 125 | 7.5705 | 8.4575 | 14.1097 | 13.8793 | 14.2635 | 15.0895 |
| H 126 | 7.5000 | 8.2694 | 14.7860 | 14.4346 | 15.0124 | 15.7545 |
| C 127 | 9.3814 | 9.7024 | 17.0834 | 16.6156 | 17.0680 | 18.1508 |
| H 128 | 10.1967 | 10.5766 | 17.8978 | 17.4558 | 17.9054 | 18.9581 |
| H 129 | 9.9038 | 10.1616 | 17.4323 | 16.9685 | 17.3518 | 18.5145 |
| H 130 | 5.8836 | 6.9249 | 10.3579 | 10.3017 | 10.4515 | 11.3274 |

| | C 43 | C 44 | H 45 | C 46 | C 47 | C 48 |
|---|---|---|---|---|---|---|
| C 43 | 0.0000 | | | | | |
| C 44 | 1.4094 | 0.0000 | | | | |
| H 45 | 2.1749 | 1.1041 | 0.0000 | | | |
| C 46 | 2.4675 | 1.4063 | 2.1601 | 0.0000 | | |
| C 47 | 7.6817 | 6.5376 | 6.7333 | 5.3534 | 0.0000 | |
| C 48 | 8.7502 | 7.7310 | 8.0515 | 6.4907 | 1.5535 | 0.0000 |
| H 49 | 8.4212 | 7.5374 | 7.9989 | 6.2678 | 2.2162 | 1.1090 |
| H 50 | 9.3466 | 8.3352 | 8.5942 | 7.1828 | 2.1991 | 1.1135 |
| H 51 | 9.5186 | 8.4697 | 8.7858 | 7.1770 | 2.2088 | 1.1127 |
| C 52 | 8.7667 | 7.4937 | 7.3726 | 6.5523 | 5.2498 | 6.3078 |
| H 53 | 8.1227 | 6.7951 | 6.5550 | 5.9664 | 4.9909 | 6.2453 |
| H 54 | 9.3541 | 8.1172 | 7.9473 | 7.2718 | 6.3588 | 7.3999 |
| H 55 | 9.5488 | 8.2487 | 8.1369 | 7.2396 | 5.0132 | 5.9176 |
| C 56 | 9.3795 | 9.9125 | 10.6819 | 9.7315 | 10.8632 | 10.6086 |

Figure 2 - cont.

| | | | | | | | |
|---|---|---|---|---|---|---|---|
| H | 57 | 9.7679 | 10.3457 | 11.0488 | 10.2877 | 11.5529 | 11.3623 |
| C | 58 | 10.3107 | 10.7334 | 11.5285 | 10.3911 | 10.9210 | 10.4681 |
| C | 59 | 10.0889 | 10.4422 | 11.3035 | 9.9432 | 10.2492 | 9.6976 |
| H | 60 | 10.9715 | 11.2520 | 12.1183 | 10.6554 | 10.5129 | 9.8082 |
| C | 61 | 8.9312 | 9.3080 | 10.2241 | 8.7796 | 9.4589 | 9.0137 |
| C | 62 | 9.1221 | 8.9809 | 9.9319 | 7.8363 | 7.1784 | 6.4651 |
| H | 63 | 9.8964 | 9.6285 | 10.5251 | 8.4061 | 7.0381 | 6.1436 |
| H | 64 | 9.6334 | 9.6105 | 10.5875 | 8.5500 | 8.0377 | 7.2738 |
| H | 65 | 8.2624 | 8.0741 | 9.0007 | 6.9353 | 6.3149 | 5.6907 |
| C | 66 | 8.0456 | 8.2105 | 9.2683 | 7.2659 | 8.3194 | 8.0290 |
| H | 67 | 8.1499 | 8.3789 | 9.4432 | 7.4894 | 8.9513 | 8.7670 |
| H | 68 | 6.9925 | 7.1623 | 8.2243 | 6.2497 | 7.6439 | 7.4954 |
| H | 69 | 8.6135 | 8.8887 | 9.9620 | 8.0253 | 9.0722 | 8.6959 |
| C | 70 | 1.4054 | 2.4084 | 3.4124 | 2.8165 | 7.7967 | 8.6730 |
| H | 71 | 2.1737 | 3.4132 | 4.3308 | 3.9180 | 8.8204 | 9.6246 |
| C | 72 | 8.6739 | 8.0633 | 8.7680 | 6.7470 | 6.0385 | 5.9659 |
| H | 73 | 9.0715 | 8.3397 | 8.9360 | 7.0304 | 6.0378 | 6.0709 |
| C | 74 | 9.5919 | 9.1259 | 9.9068 | 7.8477 | 7.2350 | 6.9700 |
| C | 75 | 9.5064 | 9.1986 | 10.0783 | 7.9586 | 7.5832 | 7.1896 |
| H | 76 | 10.4043 | 10.1759 | 11.0843 | 8.9682 | 8.5890 | 8.0955 |
| C | 77 | 8.4809 | 8.2319 | 9.1577 | 7.0128 | 6.8918 | 6.5270 |
| C | 78 | 6.7750 | 5.6956 | 5.8716 | 4.6794 | 1.5491 | 2.5342 |
| H | 79 | 6.2059 | 5.0231 | 5.0336 | 4.1523 | 2.2090 | 3.5121 |
| H | 80 | 7.5326 | 6.5040 | 6.6206 | 5.6049 | 2.1929 | 2.7299 |
| H | 81 | 6.1964 | 5.2728 | 5.6377 | 4.2132 | 2.2174 | 2.8457 |
| O | 82 | 6.7524 | 7.3149 | 8.2865 | 6.9530 | 8.8866 | 8.6182 |
| O | 83 | 5.2374 | 5.8099 | 6.6006 | 5.7959 | 8.3088 | 8.5891 |
| O | 84 | 4.4580 | 5.2191 | 6.2452 | 5.0668 | 8.3898 | 8.7315 |
| H | 85 | 12.4775 | 12.8573 | 13.6432 | 12.4494 | 12.4428 | 11.7891 |
| H | 86 | 9.3510 | 10.5213 | 11.1722 | 11.0597 | 14.5012 | 14.7958 |
| O | 87 | 6.4173 | 6.1357 | 7.0714 | 4.9325 | 5.4397 | 5.3808 |
| O | 88 | 6.4838 | 5.7262 | 6.3801 | 4.3824 | 2.9306 | 3.0247 |
| O | 89 | 4.2233 | 3.6817 | 4.5612 | 2.4041 | 4.7540 | 5.4246 |
| O | 90 | 8.1600 | 6.9924 | 7.0712 | 5.9259 | 5.0380 | 5.9777 |
| O | 91 | 10.7305 | 10.2339 | 10.9664 | 8.9720 | 8.1941 | 7.9153 |
| C | 92 | 6.9339 | 6.0900 | 6.6821 | 4.7054 | 3.9048 | 4.2778 |

Figure 2 - cont.

| | | | | | | |
|---|---|---|---|---|---|---|
| C 93 | 7.2752 | 6.3155 | 6.7487 | 5.0199 | 4.3860 | 5.0060 |
| C 94 | 7.5225 | 6.3747 | 6.5882 | 5.1565 | 3.8832 | 4.7680 |
| C 95 | 7.5152 | 6.2831 | 6.4254 | 5.0578 | 2.5805 | 3.6294 |
| C 96 | 7.1198 | 5.9823 | 6.2729 | 4.6758 | 1.5539 | 2.5210 |
| C 97 | 6.6946 | 5.7541 | 6.2800 | 4.3574 | 2.6022 | 3.0545 |
| H 98 | 7.6578 | 6.7957 | 7.2516 | 5.5804 | 5.4827 | 6.0521 |
| H 99 | 8.0711 | 6.7581 | 6.7318 | 5.6530 | 2.7710 | 3.9181 |
| H 100 | 3.4638 | 4.5516 | 5.2736 | 5.1272 | 9.2545 | 9.9194 |
| H 101 | 9.5656 | 9.9613 | 10.9766 | 9.2930 | 10.0000 | 9.4607 |
| C 102 | 3.8456 | 2.5371 | 2.7269 | 1.5055 | 4.2784 | 5.6003 |
| H 103 | 4.5218 | 3.2907 | 3.5168 | 2.1753 | 3.2764 | 4.5799 |
| H 104 | 4.0447 | 2.6364 | 2.3520 | 2.1669 | 4.7383 | 6.1853 |
| H 105 | 4.4883 | 3.2718 | 3.5026 | 2.1732 | 4.3390 | 5.6180 |
| C 106 | 1.5130 | 2.5442 | 2.7508 | 3.8507 | 8.9682 | 10.0898 |
| H 107 | 2.1797 | 3.0446 | 3.1302 | 4.3218 | 9.0889 | 10.1784 |
| H 108 | 2.1823 | 3.4384 | 3.7752 | 4.6284 | 9.8503 | 10.9100 |
| H 109 | 2.1827 | 2.7386 | 2.5460 | 4.1217 | 9.1854 | 10.4192 |
| C 110 | 6.8436 | 7.7178 | 8.7868 | 7.4927 | 10.5442 | 10.6457 |
| H 111 | 6.5641 | 7.5694 | 8.5916 | 7.5338 | 10.8940 | 11.0848 |
| H 112 | 7.7020 | 8.6093 | 9.6811 | 8.3877 | 11.4562 | 11.5226 |
| H 113 | 7.3337 | 8.0936 | 9.1608 | 7.7547 | 10.2767 | 10.2367 |
| C 114 | 6.9959 | 7.3883 | 8.3798 | 6.8126 | 9.8233 | 10.1319 |
| H 115 | 7.6569 | 7.8981 | 8.8881 | 7.1473 | 9.5342 | 9.7089 |
| H 116 | 6.7546 | 7.0699 | 7.9860 | 6.5400 | 9.7638 | 10.2104 |
| H 117 | 7.7254 | 8.2501 | 9.2423 | 7.7793 | 10.9116 | 11.1885 |
| C 118 | 9.1002 | 9.3908 | 10.3634 | 8.6874 | 9.1026 | 8.5490 |
| H 119 | 9.8873 | 10.0568 | 10.9986 | 9.2557 | 9.0324 | 8.3021 |
| H 120 | 8.2142 | 8.4495 | 9.4383 | 7.6867 | 8.2442 | 7.7807 |
| C 121 | 11.6818 | 12.0649 | 12.8098 | 11.7278 | 11.8941 | 11.3465 |
| H 122 | 12.0030 | 12.4676 | 13.1828 | 12.2455 | 12.6969 | 12.2306 |
| H 123 | 11.8079 | 12.0759 | 12.7626 | 11.7013 | 11.4663 | 10.8771 |
| C 124 | 4.2694 | 5.2796 | 5.8606 | 5.9298 | 9.7902 | 10.4335 |
| H 125 | 4.1617 | 4.9359 | 5.3937 | 5.5849 | 9.1494 | 9.8379 |
| H 126 | 4.5243 | 5.6498 | 6.1172 | 6.4981 | 10.6623 | 11.3886 |
| C 127 | 9.2519 | 10.3305 | 10.9493 | 10.8340 | 13.9898 | 14.2529 |
| H 128 | 9.4340 | 10.5002 | 11.0216 | 11.1111 | 14.3342 | 14.6715 |

| | | | | | | | |
|---|---|---|---|---|---|---|---|
| H | 80 | 3.0861 | 2.4956 | 3.7582 | 7.0674 | 6.5639 | 8.1558 |
| H | 81 | 2.6674 | 3.1993 | 3.8687 | 6.7579 | 6.3282 | 7.8286 |
| O | 82 | 7.8597 | 9.1642 | 9.6168 | 12.3865 | 12.1094 | 13.2689 |
| O | 83 | 7.8463 | 8.8266 | 9.5527 | 11.8089 | 11.3140 | 12.6971 |
| O | 84 | 7.9179 | 9.2612 | 9.5188 | 11.0225 | 10.6750 | 11.7975 |
| H | 85 | 10.8757 | 11.6060 | 12.5579 | 17.1063 | 16.8467 | 18.1296 |
| H | 86 | 14.0134 | 15.0019 | 15.7445 | 17.5264 | 16.9875 | 18.2867 |
| O | 87 | 4.4914 | 6.2436 | 5.7484 | 7.9011 | 7.9620 | 8.7382 |
| O | 88 | 2.3333 | 3.9194 | 3.5723 | 6.3872 | 6.3140 | 7.3904 |
| O | 89 | 4.8999 | 6.2877 | 5.9762 | 6.5706 | 6.3460 | 7.3812 |
| O | 90 | 6.3493 | 6.9265 | 5.6969 | 1.4146 | 2.1040 | 2.0260 |
| O | 91 | 7.4572 | 8.9378 | 7.4119 | 7.8962 | 8.6526 | 8.2708 |
| C | 92 | 3.9824 | 5.3786 | 4.2631 | 4.8444 | 5.0868 | 5.6773 |
| C | 93 | 4.9781 | 6.0967 | 4.8367 | 3.6545 | 4.0459 | 4.3754 |
| C | 94 | 5.0430 | 5.7702 | 4.5792 | 2.3941 | 2.7291 | 3.2859 |
| C | 95 | 4.0932 | 4.5407 | 3.5654 | 2.8461 | 2.8328 | 3.9309 |
| C | 96 | 2.7997 | 3.4979 | 2.7582 | 4.2555 | 4.1495 | 5.3354 |
| C | 97 | 2.7900 | 4.1133 | 3.3042 | 5.0382 | 5.0563 | 6.0286 |
| H | 98 | 5.9808 | 7.1509 | 5.8098 | 3.9416 | 4.4828 | 4.4154 |
| H | 99 | 4.6143 | 4.6432 | 3.8208 | 2.5349 | 2.3549 | 3.6356 |
| H | 100 | 9.3213 | 10.3166 | 10.8364 | 11.6632 | 11.0752 | 12.3902 |
| H | 101 | 8.3682 | 9.7954 | 10.0240 | 13.6353 | 13.5898 | 14.5268 |
| C | 102 | 5.6068 | 6.3055 | 6.2064 | 5.2241 | 4.5726 | 6.0124 |
| H | 103 | 4.6056 | 5.2325 | 5.2708 | 5.3011 | 4.6902 | 6.2248 |
| H | 104 | 6.3418 | 6.7882 | 6.7941 | 5.2306 | 4.3948 | 5.9456 |
| H | 105 | 5.6485 | 6.4563 | 6.0412 | 4.3899 | 3.8849 | 5.1319 |
| C | 106 | 9.8035 | 10.6184 | 10.8924 | 9.8775 | 9.1534 | 10.3936 |
| H | 107 | 9.8976 | 10.6005 | 11.0562 | 10.4497 | 9.6694 | 11.0295 |
| H | 108 | 10.5498 | 11.4748 | 11.6937 | 10.6604 | 9.9956 | 11.1344 |
| H | 109 | 10.2380 | 10.9575 | 11.1808 | 9.6018 | 8.8267 | 10.0342 |
| C | 110 | 9.6962 | 11.2475 | 11.2759 | 12.8915 | 12.7257 | 13.5898 |
| H | 111 | 10.1730 | 11.6326 | 11.7912 | 13.3060 | 13.0530 | 14.0083 |
| H | 112 | 10.5564 | 12.1596 | 12.0942 | 13.5928 | 13.4833 | 14.2455 |
| H | 113 | 9.2405 | 10.7731 | 10.8770 | 13.0187 | 12.8679 | 13.7794 |
| C | 114 | 9.3932 | 11.0956 | 10.3621 | 10.1144 | 10.2619 | 10.5092 |
| H | 115 | 8.9511 | 10.6918 | 9.8471 | 9.8827 | 10.1313 | 10.2974 |

Figure 2 - cont.

| | | | | | | |
|---|---|---|---|---|---|---|
| H 116 | 9.5692 | 11.2111 | 10.4089 | 9.5235 | 9.6719 | 9.8302 |
| H 117 | 10.4192 | 12.1383 | 11.4206 | 11.1766 | 11.3316 | 11.5349 |
| C 118 | 7.4709 | 8.8210 | 9.1686 | 12.9907 | 12.9024 | 13.9236 |
| H 119 | 7.2214 | 8.5045 | 8.8603 | 13.1062 | 13.0656 | 14.0646 |
| H 120 | 6.7016 | 8.1534 | 8.3927 | 11.9472 | 11.8666 | 12.8645 |
| C 121 | 10.4705 | 11.1482 | 12.1819 | 16.5664 | 16.2453 | 17.5918 |
| H 122 | 11.3793 | 12.0208 | 13.1036 | 17.3292 | 16.9604 | 18.3466 |
| H 123 | 10.0608 | 10.5812 | 11.7233 | 16.3053 | 15.9664 | 17.3552 |
| C 124 | 9.8581 | 10.7276 | 11.4040 | 12.4426 | 11.8009 | 13.1950 |
| H 125 | 9.3409 | 10.0590 | 10.8467 | 11.9742 | 11.2762 | 12.7606 |
| H 126 | 10.8536 | 11.6938 | 12.3532 | 13.0250 | 12.3458 | 13.7216 |
| C 127 | 13.4921 | 14.3873 | 15.2317 | 17.2587 | 16.6943 | 18.0615 |
| H 128 | 13.9703 | 14.7661 | 15.6817 | 17.5695 | 16.9457 | 18.3645 |
| H 129 | 13.8246 | 14.7072 | 15.5912 | 17.9454 | 17.4071 | 18.7793 |
| H 130 | 5.4388 | 6.5013 | 6.9665 | 8.7527 | 8.2832 | 9.6586 |

| | H 55 | C 56 | H 57 | C 58 | C 59 | H 60 |
|---|---|---|---|---|---|---|
| H 55 | 0.0000 | | | | | |
| C 56 | 15.3723 | 0.0000 | | | | |
| H 57 | 16.0931 | 1.1027 | 0.0000 | | | |
| C 58 | 15.5337 | 1.4063 | 2.1717 | 0.0000 | | |
| C 59 | 14.7544 | 2.4136 | 3.4164 | 1.4098 | 0.0000 | |
| H 60 | 15.0329 | 3.4163 | 4.3314 | 2.1749 | 1.1042 | 0.0000 |
| C 61 | 13.7546 | 2.8230 | 3.9257 | 2.4681 | 1.4076 | 2.1628 |
| C 62 | 10.3166 | 8.1059 | 9.1858 | 7.6877 | 6.3747 | 6.2833 |
| H 63 | 10.0773 | 8.8851 | 9.9598 | 8.3611 | 7.0353 | 6.8159 |
| H 64 | 11.3906 | 7.4990 | 8.5968 | 6.9694 | 5.6042 | 5.4228 |
| H 65 | 9.7605 | 7.5361 | 8.5842 | 7.2248 | 6.0010 | 6.0419 |
| C 66 | 10.8796 | 8.1860 | 9.2246 | 8.0973 | 6.9027 | 7.0988 |
| H 67 | 11.0608 | 9.0114 | 10.0227 | 9.0003 | 7.8431 | 8.0718 |
| H 68 | 10.3769 | 7.6395 | 8.6402 | 7.6934 | 6.5994 | 6.9385 |
| H 69 | 11.9037 | 7.5812 | 8.6338 | 7.4161 | 6.1960 | 6.3490 |
| C 70 | 9.8999 | 8.6055 | 9.0912 | 9.4866 | 9.1644 | 10.0307 |
| H 71 | 10.9486 | 8.4218 | 8.8670 | 9.3765 | 9.1102 | 10.0196 |
| C 72 | 6.4496 | 12.1455 | 13.1203 | 12.0756 | 10.9366 | 11.0573 |

Figure 2 - cont.

| | | | | | | |
|---|---|---|---|---|---|---|
| H 73 | 5.6463 | 13.0808 | 14.0346 | 13.0305 | 11.9168 | 12.0409 |
| C 74 | 7.7396 | 12.3462 | 13.3680 | 12.1816 | 10.9575 | 10.9905 |
| C 75 | 8.8232 | 11.3158 | 12.3640 | 11.0956 | 9.8311 | 9.8309 |
| H 76 | 9.8116 | 11.6587 | 12.7296 | 11.3582 | 10.0443 | 9.9631 |
| C 77 | 8.8364 | 9.9521 | 10.9899 | 9.7792 | 8.5516 | 8.6250 |
| C 78 | 6.1548 | 9.7876 | 10.3900 | 9.9705 | 9.4545 | 9.8360 |
| H 79 | 5.9473 | 10.2201 | 10.7559 | 10.5381 | 10.1065 | 10.5764 |
| H 80 | 6.8930 | 9.6970 | 10.2421 | 9.8248 | 9.3928 | 9.7360 |
| H 81 | 6.7992 | 8.8142 | 9.4588 | 9.0117 | 8.4632 | 8.8796 |
| O 82 | 12.7504 | 3.6981 | 4.5872 | 4.2134 | 3.6840 | 4.5700 |
| O 83 | 12.2239 | 4.1472 | 4.5866 | 5.1374 | 5.1683 | 6.1799 |
| O 84 | 11.5692 | 5.7868 | 6.4411 | 6.5691 | 6.1654 | 7.0479 |
| H 85 | 17.1589 | 3.4016 | 3.7156 | 2.1831 | 2.7422 | 2.5492 |
| H 86 | 18.0948 | 6.1094 | 5.6811 | 7.3658 | 8.1030 | 9.1127 |
| O 87 | 8.1973 | 8.4673 | 9.4199 | 8.5212 | 7.4904 | 7.8039 |
| O 88 | 6.4932 | 9.1051 | 9.9457 | 9.1586 | 8.2955 | 8.5939 |
| O 89 | 7.0936 | 9.0776 | 9.8449 | 9.4699 | 8.7356 | 9.2834 |
| O 90 | 2.1049 | 14.3553 | 15.1177 | 14.5775 | 13.7491 | 14.0824 |
| O 91 | 8.0180 | 13.6722 | 14.7032 | 13.4731 | 12.2220 | 12.2052 |
| C 92 | 5.1074 | 11.1751 | 12.0450 | 11.2665 | 10.3157 | 10.5915 |
| C 93 | 4.0470 | 12.4653 | 13.3045 | 12.6137 | 11.6928 | 11.9912 |
| C 94 | 2.7523 | 13.0787 | 13.8580 | 13.2599 | 12.4216 | 12.7393 |
| C 95 | 2.8580 | 12.5231 | 13.2612 | 12.6793 | 11.9093 | 12.2180 |
| C 96 | 4.2243 | 11.2103 | 11.9621 | 11.3199 | 10.5502 | 10.8450 |
| C 97 | 5.1619 | 10.4518 | 11.2744 | 10.5408 | 9.6769 | 9.9687 |
| H 98 | 4.4459 | 13.1250 | 13.9848 | 13.2834 | 12.3226 | 12.6173 |
| H 99 | 2.3173 | 13.2056 | 13.8966 | 13.3738 | 12.6631 | 12.9729 |
| H 100 | 12.2946 | 6.5225 | 6.7524 | 7.6729 | 7.7455 | 8.7750 |
| H 101 | 13.8438 | 4.7809 | 5.8543 | 4.3211 | 3.0698 | 3.1853 |
| C 102 | 5.8523 | 10.6439 | 11.2198 | 11.1896 | 10.6917 | 11.3130 |
| H 103 | 5.7334 | 10.1765 | 10.7733 | 10.6274 | 10.1118 | 10.6763 |
| H 104 | 5.8861 | 11.3048 | 11.8030 | 11.9135 | 11.5068 | 12.1605 |
| H 105 | 5.1034 | 11.3529 | 11.9941 | 11.8308 | 11.2255 | 11.7886 |
| C 106 | 10.6959 | 9.9159 | 10.1575 | 10.9817 | 10.9227 | 11.8744 |
| H 107 | 11.2012 | 9.4110 | 9.5549 | 10.5314 | 10.6007 | 11.5844 |
| H 108 | 11.5143 | 9.9849 | 10.2152 | 11.0929 | 11.0424 | 12.0168 |

Figure 2 - cont.

| | | | | | | |
|---|---|---|---|---|---|---|
| H 109 | 10.4641 | 10.9711 | 11.1987 | 12.0265 | 11.9610 | 12.8978 |
| C 110 | 13.4466 | 6.3513 | 7.0989 | 6.9041 | 6.3095 | 7.0300 |
| H 111 | 13.8904 | 6.0217 | 6.6323 | 6.7747 | 6.4024 | 7.2422 |
| H 112 | 14.1665 | 7.1106 | 7.8469 | 7.5907 | 6.9629 | 7.6020 |
| H 113 | 13.4912 | 5.5361 | 6.3734 | 5.9468 | 5.2630 | 5.9419 |
| C 114 | 10.8111 | 10.8340 | 11.6909 | 11.1911 | 10.2684 | 10.7384 |
| H 115 | 10.4970 | 10.9988 | 11.9182 | 11.2214 | 10.1943 | 10.5597 |
| H 116 | 10.2916 | 11.6018 | 12.4271 | 12.0170 | 11.1307 | 11.6316 |
| H 117 | 11.8863 | 11.1722 | 12.0113 | 11.5388 | 10.6342 | 11.1012 |
| C 118 | 13.1578 | 4.3299 | 5.4321 | 3.8486 | 2.5405 | 2.7315 |
| H 119 | 13.1816 | 4.8643 | 5.9498 | 4.1030 | 2.7038 | 2.4662 |
| H 120 | 12.1482 | 4.8848 | 5.9696 | 4.6281 | 3.4247 | 3.7285 |
| C 121 | 16.6457 | 2.5432 | 2.7506 | 1.5134 | 2.5435 | 2.7485 |
| H 122 | 17.4437 | 2.6950 | 2.4645 | 2.1832 | 3.4415 | 3.7767 |
| H 123 | 16.3249 | 3.1264 | 3.2725 | 2.1802 | 3.0356 | 3.1181 |
| C 124 | 13.0385 | 6.2060 | 6.2621 | 7.4561 | 7.7295 | 8.7977 |
| H 125 | 12.5227 | 6.3209 | 6.3478 | 7.5266 | 7.8309 | 8.8750 |
| H 126 | 13.6763 | 7.0589 | 7.0086 | 8.3621 | 8.7064 | 9.7884 |
| C 127 | 17.7765 | 5.3680 | 4.8182 | 6.6666 | 7.5256 | 8.5489 |
| H 128 | 18.0960 | 6.0708 | 5.4049 | 7.3992 | 8.3392 | 9.3718 |
| H 129 | 18.4180 | 5.0675 | 4.4219 | 6.2601 | 7.2183 | 8.1790 |
| H 130 | 9.1627 | 6.6656 | 7.2846 | 7.2593 | 6.8496 | 7.5955 |

| | C 61 | C 62 | H 63 | H 64 | H 65 | C 66 |
|---|---|---|---|---|---|---|
| C 61 | 0.0000 | | | | | |
| C 62 | 5.3816 | 0.0000 | | | | |
| H 63 | 6.1793 | 1.1127 | 0.0000 | | | |
| H 64 | 4.6990 | 1.1132 | 1.7995 | 0.0000 | | |
| H 65 | 4.9597 | 1.1071 | 1.7979 | 1.7957 | 0.0000 | |
| C 66 | 5.6299 | 2.5485 | 3.5219 | 2.7883 | 2.8284 | 0.0000 |
| H 67 | 6.5477 | 3.5194 | 4.3782 | 3.7985 | 3.8591 | 1.1119 |
| H 68 | 5.2557 | 2.8447 | 3.8720 | 3.1867 | 2.6764 | 1.1067 |
| H 69 | 4.9776 | 2.7822 | 3.7988 | 2.5575 | 3.1621 | 1.1137 |
| C 70 | 7.9305 | 8.0941 | 8.9473 | 8.5432 | 7.3069 | 6.8114 |
| H 71 | 7.8769 | 8.4485 | 9.3793 | 8.7892 | 7.7321 | 6.9297 |

Figure 2 - cont.

| | | | | | | |
|---|---|---|---|---|---|---|
| C | 72 | 9.7689 | 5.0377 | 4.8963 | 6.1225 | 5.0222 | 5.2159 |
| H | 73 | 10.7637 | 6.0682 | 5.8449 | 7.1632 | 6.0114 | 6.3050 |
| C | 74 | 9.8050 | 4.7510 | 4.5571 | 5.7486 | 5.0412 | 4.8464 |
| C | 75 | 8.6887 | 3.5979 | 3.5271 | 4.5071 | 4.0727 | 3.6310 |
| H | 76 | 8.9479 | 3.8404 | 3.7168 | 4.5620 | 4.5540 | 3.8233 |
| C | 77 | 7.3756 | 2.5276 | 2.7709 | 3.5030 | 2.8065 | 2.5627 |
| C | 78 | 8.7016 | 7.3430 | 7.3937 | 8.0765 | 6.3450 | 8.3154 |
| H | 79 | 9.3103 | 8.1463 | 8.2757 | 8.8942 | 7.1348 | 8.8599 |
| H | 80 | 8.7905 | 7.8314 | 7.8315 | 8.4750 | 6.8260 | 9.0018 |
| H | 81 | 7.6526 | 6.4749 | 6.6404 | 7.1605 | 5.4343 | 7.3538 |
| O | 82 | 2.4116 | 5.5223 | 6.5244 | 5.1912 | 4.9268 | 4.8868 |
| O | 83 | 4.2834 | 7.2352 | 8.1310 | 7.1694 | 6.3656 | 6.7431 |
| O | 84 | 4.8912 | 6.2902 | 7.3123 | 6.3573 | 5.5980 | 5.0215 |
| H | 85 | 4.1283 | 8.8292 | 9.3435 | 7.9687 | 8.5413 | 9.5247 |
| H | 86 | 7.8200 | 12.1705 | 13.2069 | 11.7380 | 11.6326 | 10.9832 |
| O | 87 | 6.2496 | 3.0129 | 3.6047 | 3.8884 | 2.3543 | 2.9586 |
| O | 88 | 7.2746 | 4.5725 | 4.7092 | 5.4667 | 3.6770 | 5.4046 |
| O | 89 | 7.4938 | 5.5341 | 6.0828 | 6.3332 | 4.7144 | 5.0917 |
| O | 90 | 12.6277 | 9.0895 | 9.0004 | 10.1756 | 8.5798 | 9.2659 |
| O | 91 | 11.0905 | 5.9263 | 5.6172 | 6.8694 | 6.3185 | 6.0118 |
| C | 92 | 9.1722 | 5.4603 | 5.4852 | 6.5317 | 4.9326 | 5.7770 |
| C | 93 | 10.5334 | 6.7872 | 6.7670 | 7.8725 | 6.3199 | 6.9367 |
| C | 94 | 11.3249 | 7.8651 | 7.7880 | 8.9380 | 7.2995 | 8.1892 |
| C | 95 | 10.9123 | 7.8272 | 7.7122 | 8.8528 | 7.1372 | 8.4580 |
| C | 96 | 9.5956 | 6.7491 | 6.6660 | 7.7207 | 5.9720 | 7.5661 |
| C | 97 | 8.6300 | 5.4948 | 5.5095 | 6.4940 | 4.7532 | 6.1641 |
| H | 98 | 11.1130 | 7.1490 | 7.1468 | 8.2359 | 6.8130 | 7.0398 |
| H | 99 | 11.7229 | 8.8097 | 8.6522 | 9.8181 | 8.0949 | 9.5259 |
| H | 100 | 6.7533 | 8.8884 | 9.8408 | 9.0011 | 8.0633 | 7.7694 |
| H | 101 | 2.1680 | 4.3227 | 5.1860 | 3.4280 | 4.3329 | 4.2681 |
| C | 102 | 9.5897 | 8.1230 | 8.5105 | 8.9461 | 7.2175 | 7.9220 |
| H | 103 | 9.0827 | 7.6110 | 7.9228 | 8.4254 | 6.6557 | 7.7394 |
| H | 104 | 10.4507 | 9.2076 | 9.5769 | 10.0201 | 8.2833 | 9.0178 |
| H | 105 | 10.0724 | 8.0061 | 8.3284 | 8.9128 | 7.1977 | 7.7633 |
| C | 106 | 9.8339 | 10.5226 | 11.3321 | 10.9699 | 9.6634 | 9.3524 |
| H | 107 | 9.6120 | 10.7914 | 11.6027 | 11.1736 | 9.8799 | 9.7704 |

Figure 2 - cont.

| | | | | | | |
|---|---|---|---|---|---|---|
| H 108 | 9.9274 | 10.7593 | 11.6326 | 11.1485 | 9.9682 | 9.3586 |
| H 109 | 10.8727 | 11.2995 | 12.0587 | 11.8151 | 10.4368 | 10.1637 |
| C 110 | 5.0501 | 6.3460 | 7.4581 | 6.1147 | 6.1162 | 4.4139 |
| H 111 | 5.2321 | 7.2313 | 8.3417 | 6.9929 | 6.8915 | 5.4340 |
| H 112 | 5.7672 | 6.8056 | 7.9026 | 6.5193 | 6.7381 | 4.6869 |
| H 113 | 4.0082 | 5.7100 | 6.8155 | 5.3412 | 5.4931 | 4.0958 |
| C 114 | 8.8762 | 6.5046 | 7.2905 | 6.9771 | 6.5314 | 4.2093 |
| H 115 | 8.8254 | 5.8268 | 6.5182 | 6.3550 | 5.9852 | 3.6657 |
| H 116 | 9.7279 | 7.2331 | 7.9509 | 7.8118 | 7.1853 | 5.1029 |
| H 117 | 9.2642 | 7.1693 | 7.9841 | 7.5181 | 7.2894 | 4.7387 |
| C 118 | 1.5104 | 4.0350 | 4.8496 | 3.2539 | 3.8095 | 4.4012 |
| H 119 | 2.1739 | 3.8401 | 4.4434 | 2.9658 | 3.7180 | 4.8004 |
| H 120 | 2.1849 | 3.3106 | 4.2347 | 2.7651 | 2.9359 | 3.5419 |
| C 121 | 3.8508 | 8.8185 | 9.3826 | 8.0507 | 8.4003 | 9.4408 |
| H 122 | 4.6338 | 9.7934 | 10.4047 | 9.0320 | 9.3528 | 10.2506 |
| H 123 | 4.3099 | 8.9410 | 9.4114 | 8.2431 | 8.4568 | 9.8050 |
| C 124 | 6.9002 | 9.5999 | 10.5384 | 9.6403 | 8.7486 | 8.6261 |
| H 125 | 7.0699 | 9.6698 | 10.5368 | 9.7672 | 8.7395 | 8.9497 |
| H 126 | 7.9054 | 10.6133 | 11.5670 | 10.6610 | 9.7824 | 9.5034 |
| C 127 | 7.3539 | 11.9313 | 12.9294 | 11.4951 | 11.3361 | 10.9595 |
| H 128 | 8.2059 | 12.7640 | 13.7463 | 12.3738 | 12.1103 | 11.8368 |
| H 129 | 7.2335 | 12.0891 | 13.0631 | 11.5630 | 11.5414 | 11.2393 |
| H 130 | 5.7695 | 6.1431 | 6.8516 | 6.5500 | 5.1152 | 5.9248 |

| | H 67 | H 68 | H 69 | C 70 | H 71 | C 72 |
|---|---|---|---|---|---|---|
| H 67 | 0.0000 | | | | | |
| H 68 | 1.7937 | 0.0000 | | | | |
| H 69 | 1.7965 | 1.7999 | 0.0000 | | | |
| C 70 | 6.8842 | 5.7755 | 7.3309 | 0.0000 | | |
| H 71 | 6.9291 | 5.9427 | 7.3317 | 1.1024 | 0.0000 | |
| C 72 | 5.2154 | 5.2043 | 6.2701 | 8.0493 | 8.7310 | 0.0000 |
| H 73 | 6.2695 | 6.2559 | 7.3654 | 8.5860 | 9.3314 | 1.0982 |
| C 74 | 4.7311 | 5.1305 | 5.8283 | 8.8147 | 9.3722 | 1.3993 |
| C 75 | 3.5864 | 4.1003 | 4.5337 | 8.5754 | 9.0239 | 2.4169 |
| H 76 | 3.6832 | 4.5363 | 4.5483 | 9.4015 | 9.7652 | 3.4075 |

Figure 2 - cont.

| | | | | | | |
|---|---|---|---|---|---|---|
| C | 77 | 2.8300 | 2.8395 | 3.5273 | 7.5077 | 7.9505 | 2.8206 |
| C | 78 | 9.0026 | 7.5006 | 8.9698 | 6.9704 | 7.9737 | 6.9217 |
| H | 79 | 9.4652 | 7.9784 | 9.5514 | 6.6073 | 7.6508 | 7.3613 |
| H | 80 | 9.7676 | 8.2041 | 9.5676 | 7.7560 | 8.7212 | 7.8396 |
| H | 81 | 8.0727 | 6.5052 | 7.9635 | 6.2178 | 7.1684 | 6.5534 |
| O | 82 | 5.5895 | 4.1779 | 4.5012 | 5.6664 | 5.5078 | 8.9443 |
| O | 83 | 7.3765 | 5.7814 | 6.6657 | 4.5661 | 4.5346 | 9.7161 |
| O | 84 | 5.3767 | 4.0448 | 5.0953 | 3.2494 | 3.0139 | 8.2365 |
| H | 85 | 10.4483 | 9.3053 | 8.7320 | 11.6414 | 11.5317 | 13.5406 |
| H | 86 | 11.2807 | 10.3284 | 10.4931 | 8.7162 | 7.9189 | 15.0934 |
| O | 87 | 3.5377 | 2.2851 | 3.8429 | 5.5313 | 6.1040 | 3.7334 |
| O | 88 | 6.0481 | 4.7165 | 6.1792 | 6.0911 | 6.9598 | 4.2665 |
| O | 89 | 5.3927 | 4.1588 | 5.9458 | 3.7119 | 4.5987 | 4.7085 |
| O | 90 | 9.3177 | 8.7697 | 10.3330 | 8.3498 | 9.3384 | 4.9217 |
| O | 91 | 5.7741 | 6.3966 | 6.9444 | 9.9908 | 10.5396 | 2.3487 |
| C | 92 | 6.0293 | 5.2941 | 6.7980 | 6.5800 | 7.4608 | 2.4536 |
| C | 93 | 7.0354 | 6.4828 | 8.0009 | 7.1013 | 8.0185 | 2.8498 |
| C | 94 | 8.3555 | 7.6595 | 9.2242 | 7.5995 | 8.6018 | 4.1438 |
| C | 95 | 8.7954 | 7.8527 | 9.4154 | 7.6803 | 8.7318 | 4.8954 |
| C | 96 | 8.0457 | 6.9220 | 8.4446 | 7.1496 | 8.1762 | 4.7413 |
| C | 97 | 6.6275 | 5.5465 | 7.0690 | 6.4608 | 7.4082 | 3.6863 |
| H | 98 | 6.9704 | 6.6864 | 8.1401 | 7.4219 | 8.2667 | 2.6499 |
| H | 99 | 9.8835 | 8.9021 | 10.4660 | 8.3895 | 9.4679 | 5.9115 |
| H | 100 | 8.0612 | 6.7491 | 7.8894 | 2.9698 | 2.5616 | 10.2608 |
| H | 101 | 5.1022 | 4.2913 | 3.3537 | 8.3761 | 8.2663 | 8.9795 |
| C | 102 | 8.1937 | 6.9779 | 8.7604 | 4.3209 | 5.4216 | 6.4370 |
| H | 103 | 8.1483 | 6.8088 | 8.5390 | 4.8662 | 5.9554 | 6.2802 |
| H | 104 | 9.2768 | 8.0597 | 9.8425 | 4.8302 | 5.9125 | 7.3997 |
| H | 105 | 7.9390 | 6.9102 | 8.6921 | 4.8131 | 5.8803 | 5.6593 |
| C | 106 | 9.4190 | 8.3068 | 9.8452 | 2.5445 | 2.7590 | 10.1527 |
| H | 107 | 9.9408 | 8.6966 | 10.1834 | 3.1285 | 3.2912 | 10.7912 |
| H | 108 | 9.3353 | 8.3562 | 9.7949 | 2.6968 | 2.4698 | 10.5241 |
| H | 109 | 10.1894 | 9.1299 | 10.7266 | 3.4016 | 3.7179 | 10.4951 |
| C | 110 | 4.4629 | 3.9603 | 4.0605 | 5.4788 | 4.9093 | 8.9025 |
| H | 111 | 5.5230 | 4.8692 | 5.1000 | 5.2742 | 4.5685 | 9.7266 |
| H | 112 | 4.5391 | 4.4655 | 4.2464 | 6.3228 | 5.6856 | 9.3184 |

Figure 2 - cont.

| | | | | | | |
|---|---|---|---|---|---|---|
| H 113 | 4.3878 | 3.6973 | 3.5503 | 6.0023 | 5.5649 | 8.8533 |
| C 114 | 3.3090 | 4.1030 | 4.8977 | 5.8330 | 5.7461 | 5.8713 |
| H 115 | 2.6965 | 3.7778 | 4.4486 | 6.5102 | 6.5418 | 5.0872 |
| H 116 | 4.2598 | 4.9004 | 5.8855 | 5.7418 | 5.7375 | 5.8278 |
| H 117 | 3.7475 | 4.7694 | 5.2406 | 6.5258 | 6.2740 | 6.8383 |
| C 118 | 5.3662 | 4.2292 | 3.6946 | 8.0050 | 8.0120 | 8.6711 |
| H 119 | 5.8273 | 4.7607 | 4.1338 | 8.8438 | 8.9381 | 8.7087 |
| H 120 | 4.5444 | 3.2236 | 3.0332 | 7.1115 | 7.1933 | 7.6698 |
| C 121 | 10.3695 | 9.0953 | 8.7264 | 10.9196 | 10.8245 | 13.3257 |
| H 122 | 11.1346 | 9.8663 | 9.5236 | 11.2790 | 11.1124 | 14.2281 |
| H 123 | 10.7886 | 9.4206 | 9.1724 | 11.1387 | 11.1442 | 13.3380 |
| C 124 | 8.9855 | 7.6176 | 8.6629 | 3.9975 | 3.6280 | 11.2174 |
| H 125 | 9.3908 | 7.9007 | 9.0477 | 4.1583 | 4.0740 | 11.1662 |
| H 126 | 9.7791 | 8.5077 | 9.5482 | 4.4172 | 3.9132 | 12.0343 |
| C 127 | 11.3590 | 10.2653 | 10.4749 | 8.6818 | 7.9931 | 14.9686 |
| H 128 | 12.2424 | 11.0880 | 11.4072 | 9.0187 | 8.3594 | 15.6383 |
| H 129 | 11.6891 | 10.6129 | 10.6640 | 9.5366 | 8.8780 | 15.4336 |
| H 130 | 6.5252 | 4.8439 | 6.3406 | 3.3907 | 4.0780 | 7.2545 |

| | H 73 | C 74 | C 75 | H 76 | C 77 | C 78 |
|---|---|---|---|---|---|---|
| H 73 | 0.0000 | | | | | |
| C 74 | 2.1359 | 0.0000 | | | | |
| C 75 | 3.3929 | 1.4047 | 0.0000 | | | |
| H 76 | 4.2862 | 2.1641 | 1.0954 | 0.0000 | | |
| C 77 | 3.9152 | 2.4550 | 1.4099 | 2.1664 | 0.0000 | |
| C 78 | 7.0769 | 8.0850 | 8.2448 | 9.2479 | 7.3362 | 0.0000 |
| H 79 | 7.4430 | 8.6004 | 8.8372 | 9.8770 | 7.9432 | 1.1120 |
| H 80 | 8.0093 | 8.9484 | 9.0455 | 10.0073 | 8.1090 | 1.1134 |
| H 81 | 6.8715 | 7.6303 | 7.6317 | 8.6105 | 6.6024 | 1.1082 |
| O 82 | 9.9068 | 9.1325 | 8.1449 | 8.5617 | 6.7787 | 8.0364 |
| O 83 | 10.5149 | 10.2416 | 9.5239 | 10.1613 | 8.1357 | 7.1265 |
| O 84 | 9.0841 | 8.6323 | 7.9037 | 8.4997 | 6.6094 | 7.5289 |
| H 85 | 14.5073 | 13.5220 | 12.3716 | 12.5035 | 11.1470 | 11.5909 |
| H 86 | 15.9771 | 15.3444 | 14.4222 | 14.7907 | 13.1381 | 13.2772 |
| O 87 | 4.6596 | 4.2024 | 3.6625 | 4.5343 | 2.3732 | 5.4827 |

Figure 2 - cont.

| | | | | | | |
|---|---|---|---|---|---|---|
| O 88 | 4.7619 | 5.2510 | 5.2231 | 6.2171 | 4.2495 | 3.0917 |
| O 89 | 5.2361 | 5.6765 | 5.6347 | 6.6336 | 4.6247 | 4.4822 |
| O 90 | 4.1767 | 6.2406 | 7.3145 | 8.3259 | 7.3276 | 6.0170 |
| O 91 | 2.5153 | 1.3681 | 2.4568 | 2.7273 | 3.7338 | 9.1767 |
| C 92 | 2.6228 | 3.7763 | 4.3342 | 5.4256 | 3.9215 | 4.6469 |
| C 93 | 2.4777 | 4.2398 | 5.1260 | 6.1857 | 5.0008 | 5.2722 |
| C 94 | 3.6124 | 5.5308 | 6.4492 | 7.5040 | 6.2906 | 4.8701 |
| C 95 | 4.5255 | 6.2681 | 7.0196 | 8.0833 | 6.6686 | 3.6540 |
| C 96 | 4.6746 | 6.0344 | 6.5284 | 7.5847 | 5.9540 | 2.5794 |
| C 97 | 3.8917 | 4.9115 | 5.2555 | 6.3204 | 4.5844 | 3.2577 |
| H 98 | 2.1002 | 3.9190 | 4.9596 | 5.9581 | 5.0680 | 6.3560 |
| H 99 | 5.4514 | 7.2734 | 8.0660 | 9.1175 | 7.7387 | 3.8376 |
| H 100 | 10.9445 | 10.8892 | 10.3600 | 11.0640 | 9.0954 | 8.0920 |
| H 101 | 10.0471 | 8.7285 | 7.4585 | 7.4999 | 6.2957 | 9.5255 |
| C 102 | 6.5248 | 7.6908 | 8.0109 | 9.0795 | 7.1952 | 3.8164 |
| H 103 | 6.4084 | 7.5362 | 7.8024 | 8.8719 | 6.9284 | 2.7147 |
| H 104 | 7.3880 | 8.6894 | 9.0751 | 10.1498 | 8.2929 | 4.2041 |
| H 105 | 5.6368 | 6.9519 | 7.4224 | 8.5017 | 6.7676 | 4.2697 |
| C 106 | 10.5254 | 11.0596 | 10.9660 | 11.8403 | 9.9419 | 7.9677 |
| H 107 | 11.1945 | 11.7083 | 11.5535 | 12.4276 | 10.4501 | 7.9423 |
| H 108 | 10.9495 | 11.3295 | 11.1668 | 11.9781 | 10.1584 | 8.8857 |
| H 109 | 10.7614 | 11.4733 | 11.5044 | 12.4139 | 10.5574 | 8.2468 |
| C 110 | 9.8830 | 8.8566 | 7.8524 | 8.1057 | 6.7387 | 9.9185 |
| H 111 | 10.6728 | 9.7829 | 8.8326 | 9.1435 | 7.6762 | 10.1300 |
| H 112 | 10.3102 | 9.1309 | 8.0836 | 8.2098 | 7.0979 | 10.9067 |
| H 113 | 9.8739 | 8.7713 | 7.6780 | 7.8966 | 6.4983 | 9.6495 |
| C 114 | 6.6115 | 5.7278 | 5.2796 | 5.6077 | 4.9185 | 9.8290 |
| H 115 | 5.8764 | 4.7670 | 4.2688 | 4.5299 | 4.0661 | 9.6830 |
| H 116 | 6.4140 | 5.8414 | 5.6566 | 6.0881 | 5.4112 | 9.8167 |
| H 117 | 7.5824 | 6.5533 | 6.0227 | 6.1856 | 5.7345 | 10.8865 |
| C 118 | 9.7024 | 8.5663 | 7.3807 | 7.5551 | 6.1319 | 8.5742 |
| H 119 | 9.7206 | 8.5588 | 7.3744 | 7.4989 | 6.1992 | 8.6080 |
| H 120 | 8.6950 | 7.6381 | 6.5071 | 6.7858 | 5.1991 | 7.7579 |
| C 121 | 14.2670 | 13.4143 | 12.3218 | 12.5463 | 11.0375 | 10.9415 |
| H 122 | 15.1694 | 14.3406 | 13.2494 | 13.4846 | 11.9451 | 11.6635 |
| H 123 | 14.2341 | 13.4971 | 12.4686 | 12.7444 | 11.1850 | 10.5057 |

| | | | | | | |
|---|---|---|---|---|---|---|
| H 105 | 3.7488 | 5.3409 | 4.1860 | 8.5052 | 7.6637 | 6.8487 |
| C 106 | 7.3037 | 8.6364 | 7.4517 | 7.6093 | 5.8475 | 5.3273 |
| H 107 | 7.2803 | 8.4856 | 7.4288 | 7.4815 | 5.4423 | 5.4086 |
| H 108 | 8.2828 | 9.5749 | 8.2960 | 7.6102 | 6.0296 | 5.2533 |
| H 109 | 7.4708 | 8.9355 | 7.8623 | 8.6714 | 6.8900 | 6.3773 |
| C 110 | 10.1442 | 10.5131 | 8.8424 | 3.1925 | 4.7870 | 2.8619 |
| H 111 | 10.2759 | 10.6816 | 9.0624 | 3.2123 | 4.3466 | 2.6920 |
| H 112 | 11.1445 | 11.5283 | 9.8361 | 4.1706 | 5.8717 | 3.9411 |
| H 113 | 9.9807 | 10.1622 | 8.5506 | 2.4455 | 4.5198 | 3.0132 |
| C 114 | 9.9378 | 10.7869 | 9.0147 | 7.1577 | 8.1959 | 5.7366 |
| H 115 | 9.8939 | 10.6317 | 8.8883 | 7.3442 | 8.5693 | 6.2064 |
| H 116 | 9.8258 | 10.8282 | 9.0872 | 7.9109 | 8.6754 | 6.2455 |
| H 117 | 10.9974 | 11.8262 | 10.0447 | 7.5663 | 8.7405 | 6.2369 |
| C 118 | 9.2625 | 8.7738 | 7.5228 | 2.8581 | 5.0911 | 5.0503 |
| H 119 | 9.3979 | 8.7279 | 7.6142 | 3.8860 | 5.9272 | 6.0247 |
| H 120 | 8.4154 | 8.0623 | 6.6903 | 2.5437 | 4.6874 | 4.3324 |
| C 121 | 11.5459 | 10.6701 | 10.0503 | 5.7261 | 6.4828 | 8.0625 |
| H 122 | 12.1985 | 11.3813 | 10.7780 | 6.2366 | 6.7695 | 8.4622 |
| H 123 | 11.1365 | 10.1341 | 9.6851 | 6.1908 | 6.6974 | 8.4494 |
| C 124 | 8.2651 | 8.8602 | 7.6934 | 4.9123 | 2.8115 | 3.6225 |
| H 125 | 7.4996 | 8.0633 | 7.0453 | 5.2550 | 2.8237 | 4.0988 |
| H 126 | 9.0418 | 9.7434 | 8.6129 | 5.8973 | 3.9080 | 4.4878 |
| C 127 | 12.7126 | 12.8329 | 11.7880 | 6.4220 | 5.7232 | 6.8071 |
| H 128 | 12.9227 | 13.0756 | 12.1244 | 7.2433 | 6.2081 | 7.4594 |
| H 129 | 13.2773 | 13.2640 | 12.2613 | 6.6570 | 6.2293 | 7.4072 |
| H 130 | 4.5243 | 5.0322 | 3.4880 | 4.1805 | 3.0635 | 3.1309 |

| | H 85 | H 86 | O 87 | O 88 | O 89 | O 90 |
|---|---|---|---|---|---|---|
| H 85 | 0.0000 | | | | | |
| H 86 | 8.8384 | 0.0000 | | | | |
| O 87 | 10.1791 | 11.5489 | 0.0000 | | | |
| O 88 | 10.7897 | 12.6041 | 2.5208 | 0.0000 | | |
| O 89 | 11.3881 | 11.2791 | 2.5613 | 2.6175 | 0.0000 | |
| O 90 | 16.2964 | 16.7225 | 6.7375 | 5.5276 | 5.5768 | 0.0000 |
| O 91 | 14.7482 | 16.6171 | 5.5680 | 6.4807 | 6.9086 | 6.6027 |

Figure 2 - cont.

| | | | | | | |
|---|---|---|---|---|---|---|
| C 92 | 12.9120 | 14.0822 | 3.1578 | 2.4250 | 2.9683 | 3.6618 |
| C 93 | 14.2947 | 15.0742 | 4.4661 | 3.6789 | 3.8103 | 2.3508 |
| C 94 | 14.9513 | 15.7148 | 5.5313 | 4.1697 | 4.4974 | 1.3682 |
| C 95 | 14.3292 | 15.4742 | 5.6060 | 3.6801 | 4.5421 | 2.4575 |
| C 96 | 12.9378 | 14.4658 | 4.6489 | 2.4174 | 3.8324 | 3.7357 |
| C 97 | 12.1800 | 13.6664 | 3.2670 | 1.3910 | 2.8433 | 4.1524 |
| H 98 | 14.9694 | 15.4894 | 4.9035 | 4.5897 | 4.3734 | 2.5290 |
| H 99 | 15.0045 | 16.1691 | 6.6475 | 4.5741 | 5.4720 | 2.7300 |
| H 100 | 9.8440 | 5.9789 | 7.0268 | 7.5950 | 5.8338 | 10.9466 |
| H 101 | 5.4243 | 8.8542 | 5.8316 | 7.4508 | 7.6043 | 12.5416 |
| C 102 | 13.1622 | 12.4234 | 5.2504 | 4.0445 | 2.8314 | 4.7674 |
| H 103 | 12.5259 | 12.4865 | 4.9225 | 3.2903 | 2.8121 | 4.8824 |
| H 104 | 13.9013 | 12.8464 | 6.3566 | 5.0229 | 3.9272 | 5.0500 |
| H 105 | 13.7688 | 13.1684 | 5.0951 | 4.0104 | 2.8155 | 3.7785 |
| C 106 | 13.1626 | 9.0431 | 7.8919 | 7.9490 | 5.7358 | 9.3812 |
| H 107 | 12.6984 | 8.5213 | 8.2890 | 8.2028 | 6.2086 | 10.0208 |
| H 108 | 13.2727 | 8.5383 | 8.2247 | 8.5885 | 6.2464 | 10.0765 |
| H 109 | 14.2036 | 10.0327 | 8.5486 | 8.4303 | 6.2333 | 9.2196 |
| C 110 | 8.6822 | 6.9047 | 5.8192 | 7.8357 | 6.4415 | 11.7449 |
| H 111 | 8.6352 | 5.8632 | 6.5206 | 8.3256 | 6.8132 | 12.2244 |
| H 112 | 9.2179 | 7.2854 | 6.5054 | 8.6788 | 7.2699 | 12.3951 |
| H 113 | 7.6647 | 6.9938 | 5.5992 | 7.5646 | 6.5267 | 11.8835 |
| C 114 | 12.9269 | 11.5251 | 5.0352 | 7.1980 | 5.4280 | 8.7846 |
| H 115 | 12.8573 | 12.2082 | 4.6397 | 6.8718 | 5.4580 | 8.5072 |
| H 116 | 13.8167 | 12.1012 | 5.4239 | 7.3323 | 5.3946 | 8.2190 |
| H 117 | 13.2207 | 11.4937 | 6.0001 | 8.2454 | 6.4801 | 9.8452 |
| C 118 | 5.1324 | 8.9234 | 5.3744 | 6.6926 | 7.0500 | 11.9644 |
| H 119 | 5.0124 | 9.8951 | 5.6500 | 6.7646 | 7.5093 | 12.1051 |
| H 120 | 6.1135 | 9.0883 | 4.2878 | 5.7104 | 5.9693 | 10.9014 |
| C 121 | 1.1119 | 8.1635 | 9.8513 | 10.3336 | 10.8375 | 15.8028 |
| H 122 | 1.7990 | 7.6363 | 10.6799 | 11.1707 | 11.5163 | 16.5848 |
| H 123 | 1.7899 | 8.9028 | 9.9299 | 10.1460 | 10.8554 | 15.6139 |
| C 124 | 9.5917 | 5.3748 | 7.8919 | 8.3061 | 6.7402 | 11.7971 |
| H 125 | 9.6507 | 6.1702 | 7.8785 | 7.9510 | 6.5753 | 11.4274 |
| H 126 | 10.4603 | 5.2147 | 8.8217 | 9.2526 | 7.5313 | 12.4144 |
| C 127 | 8.1436 | 1.1145 | 11.3451 | 12.2245 | 11.0705 | 16.5035 |

Figure 2 - cont.

| | | | | | | |
|---|---|---|---|---|---|---|
| H 128 | 8.8550 | 1.7888 | 12.0258 | 12.7424 | 11.5609 | 16.8856 |
| H 129 | 7.5027 | 1.7937 | 11.7678 | 12.6726 | 11.6917 | 17.1724 |
| H 130 | 9.3057 | 9.0823 | 4.0194 | 3.8311 | 2.8970 | 8.0239 |

| | O 91 | C 92 | C 93 | C 94 | C 95 | C 96 |
|---|---|---|---|---|---|---|
| O 91 | 0.0000 | | | | | |
| C 92 | 4.7891 | 0.0000 | | | | |
| C 93 | 4.9400 | 1.4101 | 0.0000 | | | |
| C 94 | 6.1272 | 2.4525 | 1.4051 | 0.0000 | | |
| C 95 | 6.9934 | 2.8316 | 2.4315 | 1.4089 | 0.0000 | |
| C 96 | 6.9636 | 2.4901 | 2.8408 | 2.4596 | 1.4128 | 0.0000 |
| C 97 | 5.9876 | 1.4229 | 2.4159 | 2.7890 | 2.4146 | 1.4199 |
| H 98 | 4.4186 | 2.1898 | 1.0995 | 2.1502 | 3.4129 | 3.9395 |
| H 99 | 7.9197 | 3.9257 | 3.4206 | 2.1700 | 1.0962 | 2.1696 |
| H 100 | 12.1698 | 8.7920 | 9.5726 | 10.0383 | 9.8370 | 9.0227 |
| H 101 | 9.9135 | 8.9311 | 10.2845 | 11.2835 | 11.0974 | 9.8659 |
| C 102 | 8.7293 | 4.1496 | 4.2365 | 4.0247 | 3.7657 | 3.5831 |
| H 103 | 8.6225 | 3.8726 | 4.1856 | 3.9245 | 3.3266 | 2.8243 |
| H 104 | 9.6716 | 5.0972 | 4.9958 | 4.5283 | 4.1947 | 4.2233 |
| H 105 | 7.8967 | 3.4701 | 3.2974 | 3.1167 | 3.1813 | 3.2931 |
| C 106 | 12.1760 | 8.4165 | 8.6845 | 8.8474 | 8.8243 | 8.4908 |
| H 107 | 12.8765 | 8.9502 | 9.3094 | 9.4121 | 9.2344 | 8.7967 |
| H 108 | 12.4295 | 8.9808 | 9.2718 | 9.5581 | 9.6386 | 9.2961 |
| H 109 | 12.5263 | 8.7009 | 8.7981 | 8.8311 | 8.8448 | 8.6750 |
| C 110 | 10.0263 | 8.6568 | 9.6917 | 10.7372 | 10.8918 | 9.9744 |
| H 111 | 10.9776 | 9.2640 | 10.2699 | 11.2285 | 11.3205 | 10.3994 |
| H 112 | 10.2148 | 9.3219 | 10.3173 | 11.4332 | 11.6824 | 10.8119 |
| H 113 | 9.9771 | 8.6122 | 9.7552 | 10.7922 | 10.8446 | 9.8239 |
| C 114 | 6.5093 | 6.4447 | 6.9260 | 8.1843 | 8.9641 | 8.6156 |
| H 115 | 5.5132 | 6.0093 | 6.5368 | 7.8718 | 8.6713 | 8.3099 |
| H 116 | 6.5267 | 6.3029 | 6.5676 | 7.7635 | 8.6512 | 8.4670 |
| H 117 | 7.2353 | 7.5406 | 8.0148 | 9.2790 | 10.0745 | 9.7205 |
| C 118 | 9.8074 | 8.3829 | 9.7630 | 10.6692 | 10.3694 | 9.0866 |
| H 119 | 9.7566 | 8.5046 | 9.9079 | 10.7850 | 10.4237 | 9.1112 |
| H 120 | 8.9159 | 7.3267 | 8.6951 | 9.6200 | 9.3701 | 8.1207 |

| | | | | | | |
|---|---|---|---|---|---|---|
| H 120 | 6.9881 | 9.1891 | 10.2774 | 6.7898 | 1.7836 | 8.4064 |
| C 121 | 11.7222 | 14.5811 | 14.4508 | 9.0082 | 5.5130 | 12.4562 |
| H 122 | 12.5517 | 15.3953 | 15.2293 | 9.1338 | 6.3111 | 13.0388 |
| H 123 | 11.5252 | 14.5325 | 14.0974 | 9.3081 | 6.0806 | 12.3164 |
| C 124 | 9.1389 | 10.9973 | 11.1506 | 1.1112 | 8.1198 | 7.2375 |
| H 125 | 8.7682 | 10.8297 | 10.5694 | 1.7805 | 8.4561 | 6.7569 |
| H 126 | 10.0060 | 11.6777 | 11.8661 | 1.8067 | 9.0757 | 7.8288 |
| C 127 | 13.3288 | 15.3620 | 15.7757 | 5.8176 | 8.6241 | 12.1323 |
| H 128 | 13.8129 | 15.8829 | 16.0860 | 6.0881 | 9.5936 | 12.3850 |
| H 129 | 13.8384 | 15.9773 | 16.3741 | 6.7002 | 8.5213 | 12.8706 |
| H 130 | 4.7552 | 7.1907 | 7.1355 | 3.8848 | 6.6435 | 3.9955 |

| | H 103 | H 104 | H 105 | C 106 | H 107 | H 108 |
|---|---|---|---|---|---|---|
| H 103 | 0.0000 | | | | | |
| H 104 | 1.7989 | 0.0000 | | | | |
| H 105 | 1.7747 | 1.8038 | 0.0000 | | | |
| C 106 | 5.7839 | 5.0243 | 5.7589 | 0.0000 | | |
| H 107 | 6.0348 | 5.3721 | 6.3102 | 1.1149 | 0.0000 | |
| H 108 | 6.6785 | 5.9912 | 6.5338 | 1.1112 | 1.7916 | 0.0000 |
| H 109 | 5.9445 | 4.8662 | 5.7508 | 1.1120 | 1.7902 | 1.7989 |
| C 110 | 8.8415 | 9.6379 | 9.0083 | 7.5889 | 7.8171 | 7.1954 |
| H 111 | 9.0008 | 9.6760 | 9.2424 | 7.1208 | 7.2496 | 6.6631 |
| H 112 | 9.7764 | 10.5411 | 9.8215 | 8.3999 | 8.6911 | 7.9129 |
| H 113 | 8.8748 | 9.8445 | 9.2127 | 8.1591 | 8.2942 | 7.8783 |
| C 114 | 8.0883 | 8.6084 | 7.2884 | 8.0624 | 8.8663 | 7.7783 |
| H 115 | 8.1536 | 8.8416 | 7.3839 | 8.8335 | 9.6078 | 8.6451 |
| H 116 | 7.8673 | 8.1960 | 6.8573 | 7.7877 | 8.6831 | 7.5252 |
| H 117 | 9.1459 | 9.6216 | 8.3529 | 8.6701 | 9.4693 | 8.2616 |
| C 118 | 8.9148 | 10.3747 | 9.7440 | 10.1602 | 10.0935 | 10.2502 |
| H 119 | 9.2427 | 10.8056 | 10.1331 | 11.0041 | 10.9288 | 11.1621 |
| H 120 | 7.9343 | 9.3889 | 8.6879 | 9.3523 | 9.3616 | 9.4743 |
| C 121 | 11.8330 | 13.1432 | 13.1238 | 12.3089 | 11.7909 | 12.4483 |
| H 122 | 12.4605 | 13.6766 | 13.7564 | 12.5054 | 11.9246 | 12.6004 |
| H 123 | 11.6204 | 12.9646 | 13.0086 | 12.4627 | 11.9077 | 12.6972 |
| C 124 | 7.3759 | 7.5385 | 8.0850 | 4.1263 | 3.5053 | 4.0767 |

Figure 2 - cont.

| | | | | | | |
|---|---|---|---|---|---|---|
| H 125 | 6.8133 | 6.9712 | 7.6949 | 4.0627 | 3.2685 | 4.2997 |
| H 126 | 8.0794 | 8.0256 | 8.6697 | 4.0064 | 3.3319 | 3.7838 |
| C 127 | 12.1141 | 12.5366 | 12.9317 | 8.9921 | 8.3734 | 8.6160 |
| H 128 | 12.3859 | 12.6975 | 13.2380 | 9.0254 | 8.3138 | 8.6789 |
| H 129 | 12.7814 | 13.3155 | 13.6640 | 9.9846 | 9.3632 | 9.6403 |
| H 130 | 3.6724 | 4.7464 | 4.7121 | 5.0611 | 5.0129 | 5.6220 |

| | H 109 | C 110 | H 111 | H 112 | H 113 | C 114 |
|---|---|---|---|---|---|---|
| H 109 | 0.0000 | | | | | |
| C 110 | 8.6108 | 0.0000 | | | | |
| H 111 | 8.1774 | 1.1116 | 0.0000 | | | |
| H 112 | 9.3916 | 1.1105 | 1.8054 | 0.0000 | | |
| H 113 | 9.2036 | 1.1111 | 1.7754 | 1.8029 | 0.0000 | |
| C 114 | 8.6369 | 5.0821 | 5.8453 | 5.0271 | 5.6943 | 0.0000 |
| H 115 | 9.4042 | 5.5286 | 6.4124 | 5.4762 | 5.9591 | 1.1151 |
| H 116 | 8.2350 | 5.9397 | 6.5956 | 5.9504 | 6.6076 | 1.1114 |
| H 117 | 9.2660 | 5.1069 | 5.8628 | 4.8170 | 5.8024 | 1.1117 |
| C 118 | 11.1642 | 4.8572 | 5.3508 | 5.4568 | 3.7874 | 8.0338 |
| H 119 | 11.9775 | 5.9137 | 6.4503 | 6.4699 | 4.8527 | 8.7156 |
| H 120 | 10.3237 | 4.4132 | 4.9900 | 5.1053 | 3.4528 | 7.1273 |
| C 121 | 13.3381 | 8.3675 | 8.2213 | 9.0032 | 7.4008 | 12.6696 |
| H 122 | 13.5397 | 8.7508 | 8.4781 | 9.3653 | 7.8518 | 13.2748 |
| H 123 | 13.4520 | 9.0436 | 8.9166 | 9.7525 | 8.0763 | 13.1255 |
| C 124 | 5.1624 | 5.7709 | 4.9591 | 6.7111 | 6.0047 | 8.8052 |
| H 125 | 5.0104 | 6.5428 | 5.8276 | 7.5448 | 6.6727 | 9.3259 |
| H 126 | 4.9626 | 6.3946 | 5.4972 | 7.2407 | 6.7533 | 9.3062 |
| C 127 | 9.9883 | 7.1251 | 6.1185 | 7.6351 | 7.0809 | 11.8039 |
| H 128 | 9.9592 | 8.0401 | 7.0066 | 8.5916 | 8.0380 | 12.5586 |
| H 129 | 10.9981 | 7.5253 | 6.5936 | 7.9862 | 7.3486 | 12.3863 |
| H 130 | 5.8564 | 5.7985 | 5.8025 | 6.8621 | 5.6788 | 7.0907 |

| | H 115 | H 116 | H 117 | C 118 | H 119 | H 120 |
|---|---|---|---|---|---|---|
| H 115 | 0.0000 | | | | | |
| H 116 | 1.7892 | 0.0000 | | | | |

Figure 2 - cont.

| | | | | | | |
|---|---|---|---|---|---|---|
| H 117 | 1.7930 | 1.7999 | 0.0000 | | | |
| C 118 | 7.8297 | 8.9328 | 8.4313 | 0.0000 | | |
| H 119 | 8.3931 | 9.6053 | 9.1525 | 1.1101 | 0.0000 | |
| H 120 | 6.9187 | 7.9777 | 7.6156 | 1.1080 | 1.8012 | 0.0000 |
| C 121 | 12.6658 | 13.5069 | 13.0084 | 5.0815 | 5.1008 | 5.9461 |
| H 122 | 13.3462 | 14.1026 | 13.5713 | 5.9568 | 6.0917 | 6.7964 |
| H 123 | 13.0860 | 13.9203 | 13.5437 | 5.4834 | 5.3618 | 6.2670 |
| C 124 | 9.4731 | 9.0582 | 9.2418 | 7.7055 | 8.6320 | 7.2626 |
| H 125 | 9.9283 | 9.5300 | 9.8650 | 7.9067 | 8.7435 | 7.4410 |
| H 126 | 10.0620 | 9.4921 | 9.6758 | 8.7233 | 9.6763 | 8.2945 |
| C 127 | 12.4318 | 12.3834 | 11.8660 | 8.5754 | 9.4915 | 8.7767 |
| H 128 | 13.2211 | 13.0731 | 12.6550 | 9.4708 | 10.3649 | 9.6366 |
| H 129 | 12.9515 | 13.0338 | 12.4282 | 8.5092 | 9.3627 | 8.8480 |
| H 130 | 7.3057 | 7.3156 | 7.9453 | 5.9005 | 6.4833 | 5.0365 |

| | C 121 | H 122 | H 123 | C 124 | H 125 | H 126 |
|---|---|---|---|---|---|---|
| C 121 | 0.0000 | | | | | |
| H 122 | 1.1113 | 0.0000 | | | | |
| H 123 | 1.1150 | 1.7914 | 0.0000 | | | |
| C 124 | 8.6886 | 8.7001 | 8.9666 | 0.0000 | | |
| H 125 | 8.6925 | 8.7352 | 8.8325 | 1.1134 | 0.0000 | |
| H 126 | 9.5496 | 9.4708 | 9.8598 | 1.1104 | 1.8017 | 0.0000 |
| C 127 | 7.3901 | 6.8238 | 8.0558 | 5.0887 | 5.7299 | 5.0488 |
| H 128 | 8.0350 | 7.4074 | 8.6046 | 5.2239 | 5.7550 | 5.0239 |
| H 129 | 6.8124 | 6.1434 | 7.5342 | 5.9936 | 6.5722 | 6.0614 |
| H 130 | 8.5805 | 9.1266 | 8.5609 | 4.4935 | 4.1382 | 5.4652 |

| | C 127 | H 128 | H 129 | H 130 |
|---|---|---|---|---|
| C 127 | 0.0000 | | | |
| H 128 | 1.1129 | 0.0000 | | |
| H 129 | 1.1108 | 1.7973 | 0.0000 | |
| H 130 | 8.6859 | 9.0950 | 9.2683 | 0.0000 |

Figure 2 - cont.

ATOMIC CHARGES
P   1   0.0000000000
C   2   0.0000000000
C   3   0.0000000000
Rh  4   0.0000000000
O   5   0.0000000000
O   6   0.0000000000
P   7   0.0000000000
C   8   0.0000000000
C   9   0.0000000000
C  10   0.0000000000
H  11   0.0000000000
H  12   0.0000000000
H  13   0.0000000000
C  14   0.0000000000
C  15   0.0000000000
C  16   0.0000000000
C  17   0.0000000000
C  18   0.0000000000
C  19   0.0000000000
H  20   0.0000000000
C  21   0.0000000000
C  22   0.0000000000
H  23   0.0000000000
C  24   0.0000000000
C  25   0.0000000000
C  26   0.0000000000
C  27   0.0000000000
H  28   0.0000000000
H  29   0.0000000000
H  30   0.0000000000
C  31   0.0000000000
C  32   0.0000000000
C  33   0.0000000000
C  34   0.0000000000

Figure 2 - cont.

| | | |
|---|---|---|
| H | 35 | 0.0000000000 |
| C | 36 | 0.0000000000 |
| C | 37 | 0.0000000000 |
| H | 38 | 0.0000000000 |
| C | 39 | 0.0000000000 |
| H | 40 | 0.0000000000 |
| H | 41 | 0.0000000000 |
| H | 42 | 0.0000000000 |
| C | 43 | 0.0000000000 |
| C | 44 | 0.0000000000 |
| H | 45 | 0.0000000000 |
| C | 46 | 0.0000000000 |
| C | 47 | 0.0000000000 |
| C | 48 | 0.0000000000 |
| H | 49 | 0.0000000000 |
| H | 50 | 0.0000000000 |
| H | 51 | 0.0000000000 |
| C | 52 | 0.0000000000 |
| H | 53 | 0.0000000000 |
| H | 54 | 0.0000000000 |
| H | 55 | 0.0000000000 |
| C | 56 | 0.0000000000 |
| H | 57 | 0.0000000000 |
| C | 58 | 0.0000000000 |
| C | 59 | 0.0000000000 |
| H | 60 | 0.0000000000 |
| C | 61 | 0.0000000000 |
| C | 62 | 0.0000000000 |
| H | 63 | 0.0000000000 |
| H | 64 | 0.0000000000 |
| H | 65 | 0.0000000000 |
| C | 66 | 0.0000000000 |
| H | 67 | 0.0000000000 |
| H | 68 | 0.0000000000 |
| H | 69 | 0.0000000000 |
| C | 70 | 0.0000000000 |

Figure 2 - cont.

| | | |
|---|---|---|
| H | 71 | 0.0000000000 |
| C | 72 | 0.0000000000 |
| H | 73 | 0.0000000000 |
| C | 74 | 0.0000000000 |
| C | 75 | 0.0000000000 |
| H | 76 | 0.0000000000 |
| C | 77 | 0.0000000000 |
| C | 78 | 0.0000000000 |
| H | 79 | 0.0000000000 |
| H | 80 | 0.0000000000 |
| H | 81 | 0.0000000000 |
| O | 82 | 0.0000000000 |
| O | 83 | 0.0000000000 |
| O | 84 | 0.0000000000 |
| H | 85 | 0.0000000000 |
| H | 86 | 0.0000000000 |
| O | 87 | 0.0000000000 |
| O | 88 | 0.0000000000 |
| O | 89 | 0.0000000000 |
| O | 90 | 0.0000000000 |
| O | 91 | 0.0000000000 |
| C | 92 | 0.0000000000 |
| C | 93 | 0.0000000000 |
| C | 94 | 0.0000000000 |
| C | 95 | 0.0000000000 |
| C | 96 | 0.0000000000 |
| C | 97 | 0.0000000000 |
| H | 98 | 0.0000000000 |
| H | 99 | 0.0000000000 |
| H | 100 | 0.0000000000 |
| H | 101 | 0.0000000000 |
| C | 102 | 0.0000000000 |
| H | 103 | 0.0000000000 |
| H | 104 | 0.0000000000 |
| H | 105 | 0.0000000000 |
| C | 106 | 0.0000000000 |

BOND ANGLES 77  75  74  Car  Car  Car   121.435
75  74  72  Car  Car  Car   119.070
74  75  77  Car  Car  Car   121.435
75  77   8  Car  Car  Car   118.140
62  26  66  C3   C3   C3    110.638
26  66  68  C3   C3   HC    112.347
77  26  66  Car  C3   C3    111.426
26  66  68  C3   C3   HC    112.347
66  26  62  C3   C3   C3    110.638

Figure 2 - cont.

```
 26  62  65 C3  C3  HC  111.768
 77  26  62 Car C3  C3  109.003
 26  62  65 C3  C3  HC  111.768
 66  26  77 C3  C3  Car 111.426
 26  77   8 C3  Car Car 122.593
 62  26  77 C3  C3  Car 109.003
 26  77   8 C3  Car Car 122.593
 36 114 116 Car C3  HC  111.647
116 114  36 HC  C3  Car 111.647
114  36  34 C3  Car Car 121.045
 25  37  36 Car Car Car 122.588
 37  36  34 Car Car Car 117.797
 36  37  25 Car Car Car 122.588
 37  25  24 Car Car Car 117.800
111 110  25 HC  C3  Car 111.282
110  25  24 C3  Car Car 121.216
 25 110 111 Car C3  HC  111.282
 61 118 120 Car C3  HC  112.200
120 118  61 HC  C3  Car 112.200
118  61  59 C3  Car Car 121.028
118  61  14 C3  Car Car 121.002
  9  72  73 Car Car HC  120.268
 73  72   9 HC  Car Car 120.268
 72   9  92 Car Car Car 114.297
 14  61  59 Car Car Car 117.855
 61  59  58 Car Car Car 122.327
 59  61  14 Car Car Car 117.855
 61  14  15 Car Car Car 121.797
  9   8  87 Car Car O3  123.927
  8  87   7 Car O3  P   131.744
 87   8   9 O3  Car Car 123.927
  8   9  92 Car Car Car 128.484
 33  34  35 Car Car HC  118.218
 35  34  33 HC  Car Car 118.218
 34  33  32 Car Car Car 118.085
  1  82  14 P   O3  Car 120.610
```

Figure 2 - cont.

```
82  14  15  O3  Car Car  119.385
14  82   1  Car O3  P    120.610
82   1   4  O3  P   Rh   124.783
82   1  83  O3  P   O3   100.058
84  24  33  O3  Car Car  120.132
24  33  32  Car Car Car  122.827
33  24  84  Car Car O3   120.132
24  84   1  Car O3  P    124.709
56  58 121  Car Car C3   121.117
58 121 122  Car C3  HC   111.653
58 121 123  Car C3  HC   111.184
121 58  56  C3  Car Car  121.117
58  56  57  Car Car HC   119.407
123 121 122 HC  C3  HC   107.157
122 121 123 HC  C3  HC   107.157
16  15  56  Car Car Car  120.314
15  56  57  Car Car HC   118.443
56  15  16  Car Car Car  120.314
15  16  17  Car Car Car  122.788
83   1   4  O3  P   Rh   109.226
 1   4 130  P   Rh  HC    78.084
 1   4   2  P   Rh  C3   112.670
 4   1  83  Rh  P   O3   109.226
21  22  16  Car Car Car  122.277
22  16  17  Car Car Car  117.505
16  22  21  Car Car Car  122.277
22  21  19  Car Car Car  117.993
97  92  93  Car Car Car  117.032
92  93  94  Car Car Car  121.187
93  92  97  Car Car Car  117.032
92  97  96  Car Car Car  122.314
88   7  89  O3  P   O3   101.849
 7  89  31  P   O3  Car  124.866
 4   7  89  Rh  P   O3   118.329
 7  89  31  P   O3  Car  124.866
89   7  88  O3  P   O3   101.849
```

Figure 2 - cont.

```
7    88  97   P   O3  Car   121.837
4    7   88   Rh  P   O3    114.726
7    88  97   P   O3  Car   121.837
89   7   4    O3  P   Rh    118.329
7    4   130  P   Rh  HC    82.350
7    4   2    P   Rh  C3    122.312
88   7   4    O3  P   Rh    114.726
7    4   130  P   Rh  HC    82.350
7    4   2    P   Rh  C3    122.312
128  127 21   HC  C3  Car   111.510
127  21  19   C3  Car Car   120.658
21   127 128  Car C3  HC    111.510
70   32  31   Car Car Car   118.185
32   31  46   Car Car Car   121.161
31   32  70   Car Car Car   118.185
32   70  43   Car Car Car   122.264
2    4   130  C3  Rh  HC    80.959
130  4   2    HC  Rh  C3    80.959
4    2   6    Rh  C3  O3    176.696
18   17  83   Car Car O3    117.202
83   17  18   O3  Car Car   117.202
17   18  124  Car Car C3    120.169
20   19  18   HC  Car Car   118.438
19   18  124  Car Car C3    121.933
18   19  20   Car Car HC    118.438
95   94  90   Car Car O3    124.473
94   90  52   Car O3  C3    118.689
90   94  95   O3  Car Car   124.473
94   95  99   Car Car HC    119.525
47   48  50   C3  C3  HC    109.988
50   48  47   HC  C3  C3    109.988
48   47  78   C3  C3  C3    109.530
48   47  10   C3  C3  C3    107.327
125  124 126  HC  C3  HC    108.229
126  124 125  HC  C3  HC    108.229
47   96  95   C3  Car Car   120.808
```

Figure 2 - cont.

```
96  95  99  Car Car HC   119.162
95  96  47  Car Car C3   120.808
96  47  78  Car C3  C3   112.458
96  47  10  Car C3  C3   111.679
44  46  102 Car Car C3   121.188
46  102 103 Car C3  HC   111.677
46  102 104 Car C3  HC   110.960
102 46  44  C3  Car Car  121.188
46  44  45  Car Car HC   118.245
106 43  44  C3  Car Car  121.018
43  44  45  Car Car HC   119.343
44  43  106 Car Car C3   121.018
43  106 107 Car C3  HC   111.182
43  106 109 Car C3  HC   111.596
10  47  78  C3  C3  C3   107.268
47  78  80  C3  C3  HC   109.812
47  78  79  C3  C3  HC   111.150
78  47  10  C3  C3  C3   107.268
47  10  13  C3  C3  HC   109.121
47  10  11  C3  C3  HC   112.336
104 102 103 HC  C3  HC   108.258
103 102 104 HC  C3  HC   108.258
55  52  54  HC  C3  HC   108.865
53  52  54  HC  C3  HC   109.015
54  52  55  HC  C3  HC   108.865
53  52  55  HC  C3  HC   108.806
54  52  53  HC  C3  HC   109.015
55  52  53  HC  C3  HC   108.806
109 106 107 HC  C3  HC   107.008
107 106 109 HC  C3  HC   107.008
79  78  80  HC  C3  HC   107.286
80  78  79  HC  C3  HC   107.286
11  10  13  HC  C3  HC   107.073
13  10  11  HC  C3  HC   107.073
```

Figure 2 - cont.

TORSION ANGLES

| | | | | |
|---|---|---|---|---|
| 28 | 27 | 26 | 66 | -59.605 |
| 28 | 27 | 26 | 62 | -178.001 |
| 28 | 27 | 26 | 77 | 62.702 |
| 29 | 27 | 26 | 66 | 58.847 |
| 29 | 27 | 26 | 62 | -59.549 |
| 29 | 27 | 26 | 77 | -178.847 |
| 30 | 27 | 26 | 66 | 177.525 |
| 30 | 27 | 26 | 62 | 59.129 |
| 30 | 27 | 26 | 77 | -60.168 |
| 40 | 39 | 91 | 74 | -60.791 |
| 42 | 39 | 91 | 74 | -179.536 |
| 41 | 39 | 91 | 74 | 61.737 |
| 39 | 91 | 74 | 75 | -0.365 |
| 39 | 91 | 74 | 72 | -177.770 |
| 76 | 75 | 74 | 91 | -1.418 |
| 76 | 75 | 74 | 72 | 175.916 |
| 77 | 75 | 74 | 91 | -179.964 |
| 77 | 75 | 74 | 72 | -2.629 |
| 76 | 75 | 77 | 26 | -3.330 |
| 76 | 75 | 77 | 8 | 179.467 |
| 74 | 75 | 77 | 26 | 175.219 |
| 74 | 75 | 77 | 8 | -1.984 |
| 27 | 26 | 66 | 67 | 61.462 |
| 27 | 26 | 66 | 69 | -57.251 |
| 27 | 26 | 66 | 68 | -177.937 |
| 62 | 26 | 66 | 67 | 177.299 |
| 62 | 26 | 66 | 69 | 58.586 |
| 62 | 26 | 66 | 68 | -62.100 |
| 77 | 26 | 66 | 67 | -61.262 |
| 77 | 26 | 66 | 69 | -179.975 |
| 77 | 26 | 66 | 68 | 59.339 |
| 27 | 26 | 62 | 64 | 56.938 |
| 27 | 26 | 62 | 63 | -62.337 |
| 27 | 26 | 62 | 65 | 176.909 |
| 66 | 26 | 62 | 64 | -58.923 |

| | | | | |
|---|---|---|---|---|
| 60 | 59 | 58 | 56 | 177.971 |
| 61 | 59 | 58 | 121 | 177.129 |
| 61 | 59 | 58 | 56 | -1.945 |
| 36 | 34 | 33 | 24 | -3.193 |
| 36 | 34 | 33 | 32 | 166.816 |
| 35 | 34 | 33 | 24 | 179.719 |
| 35 | 34 | 33 | 32 | -10.273 |
| 8 | 87 | 7 | 89 | -70.874 |
| 8 | 87 | 7 | 88 | 32.769 |
| 8 | 87 | 7 | 4 | 157.502 |
| 1 | 82 | 14 | 61 | 112.795 |
| 1 | 82 | 14 | 15 | -73.028 |
| 14 | 82 | 1 | 84 | 153.850 |
| 14 | 82 | 1 | 4 | -67.731 |
| 14 | 82 | 1 | 83 | 54.302 |
| 72 | 9 | 92 | 93 | -29.889 |
| 72 | 9 | 92 | 97 | 138.764 |
| 8 | 9 | 92 | 93 | 157.021 |
| 8 | 9 | 92 | 97 | -34.325 |
| 25 | 24 | 33 | 34 | 5.081 |
| 25 | 24 | 33 | 32 | -164.423 |
| 84 | 24 | 33 | 34 | 179.586 |
| 84 | 24 | 33 | 32 | 10.082 |
| 25 | 24 | 84 | 1 | -100.672 |
| 33 | 24 | 84 | 1 | 84.655 |
| 61 | 14 | 15 | 56 | -3.803 |
| 61 | 14 | 15 | 16 | 171.601 |
| 82 | 14 | 15 | 56 | -177.784 |
| 82 | 14 | 15 | 16 | -2.380 |
| 59 | 58 | 121 | 85 | 36.223 |
| 59 | 58 | 121 | 122 | 157.246 |
| 59 | 58 | 121 | 123 | -83.134 |
| 56 | 58 | 121 | 85 | -144.732 |
| 56 | 58 | 121 | 122 | -23.709 |
| 56 | 58 | 121 | 123 | 95.911 |
| 59 | 58 | 56 | 15 | 1.884 |

UNSYMMETRIC BISPHOSPHITE

The invention relates to an unsymmetric bisphosphite, to a process for preparation thereof and to the reaction thereof with metals to give mixtures comprising complexes of the unsymmetric bisphosphite and the metal, and to the use thereof as a catalytically active composition in hydroformylation reactions, wherein the hydroformylation-active composition comprises, as well as the complex of metal and unsymmetric bisphosphite, unbound bisphosphite and at least one further component.

The reactions between olefin compounds, carbon monoxide and hydrogen in the presence of a catalyst to give the aldehydes with one carbon atom more are known as hydroformylation or the oxo process. The catalysts used in these reactions are frequently compounds of the transition metals of group VIII of the Periodic Table of the Elements. Known ligands are, for example, compounds from the classes of the phosphines, phosphites and phosphonites, each with trivalent phosphorus $P^{III}$. A good overview of the state of the hydroformylation of olefins can be found in B. CORNILS, W. A. HERRMANN, "Applied Homogeneous Catalysis with Organometallic Compounds", vol. 1 & 2, VCH, Weinheim, New York, 1996 or R. Franke, D. Selent, A. Borner, "Applied Hydroformylation", Chem. Rev., 2012, DOI: 10.1021/cr3001803.

Every catalytically active composition has its specific benefits. According to the feedstock and target product, therefore, different catalytically active compositions are used.

U.S. Pat. No. 4,694,109 and U.S. Pat. No. 4,879,416 describe bisphosphine ligands and use thereof in the hydroformylation of olefins at low synthesis gas pressures. Particularly in the case of hydroformylation of propene, ligands of this type achieve high activities and high n/i selectivities (n/i=the ratio of linear aldehyde (=n) to branched (=iso) aldehyde). WO 95/30680 discloses bidentate phosphine ligands and the use thereof in catalysis, including in hydroformylation reactions. Ferrocene-bridged bisphosphines are described, for example, in patent specifications U.S. Pat. No. 4,169,861, U.S. Pat. No. 4,201,714 and U.S. Pat. No. 4,193,943 as ligands for hydroformylations.

The disadvantage of bi- and polydentate phosphine ligands is a relatively high level of complexity necessary for preparation thereof. It is therefore often unfeasible to use such systems in industrial operations. An additional factor is comparatively low activity, which has to be compensated for by chemical engineering, through high reaction times. This in turn leads to unwanted side reactions of the products.

Rhodium monophosphite complexes in catalytically active compositions are suitable for the hydroformylation of branched olefins having internal double bonds, but the n/i selectivity for terminally hydroformylated compounds is low. EP 0 155 508 discloses the use of bisarylene-substituted monophosphites in the rhodium-catalysed hydroformylation of sterically hindered olefins, e.g. isobutene.

The bisphosphites disclosed in EP 1 294 731 have olefin conversions up to 98% in the hydroformylation of n-octene mixtures. However, n/i selectivity for nonanal, which is likewise desired, is in need of improvement at 36.8% up to a maximum of 57.6%. This is all the more true in that the use of the catalytically active composition in industrial operations requires a service life measured in days rather than hours.

The literature discloses the synthesis of symmetric bisphosphites as disclosed since U.S. Pat. No. 4,769,498, and the use thereof in catalytically active, transition metal-containing compositions for hydroformylation of unsaturated compounds.

In U.S. Pat. No. 4,769,498, and also in U.S. Pat. No. 5,723,641, preferably symmetric bisphosphites are prepared and used as ligands for hydroformylation. The symmetric bisphosphite ligands used in the hydroformylation are prepared at low temperatures. Compliance with these low temperatures is absolutely necessary, since higher temperatures, according to these US documents, would lead to rearrangements and ultimately to unsymmetric bisphosphites, which is not wanted here.

WO95/28228 and U.S. Pat. No. 5,512,695 describe the synthesis of unsymmetric bisphosphites. In this case, the synthesis is performed at room temperature and/or at elevated temperature.

WO 95/28228 on page 19 describes the synthesis and the use of the unsymmetric ligand A in hydrocyanation, which is the unsymmetric variant of what is called the biphephos ligand (which is symmetric) (see unsymmetric isomer of biphephos).

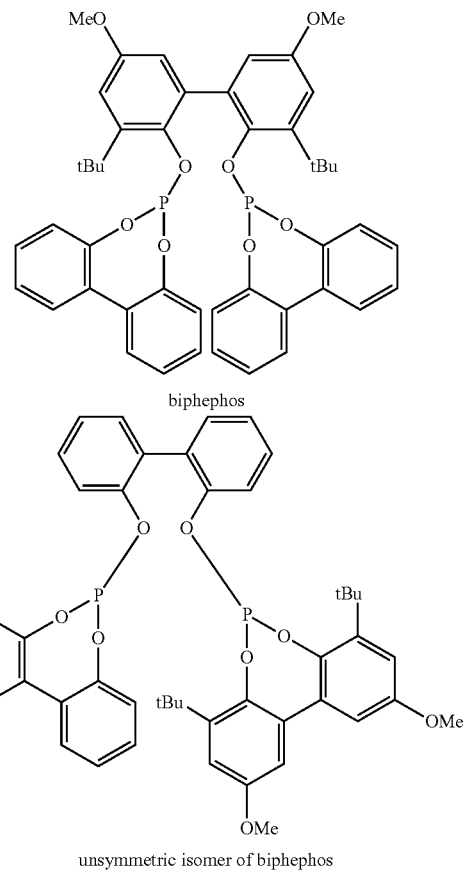

unsymmetric isomer of biphephos

The use of the two ligands, i.e. of the symmetric biphephos ligand and the unsymmetric isomer thereof, in the hydroformylation is likewise described. Rhodium-catalyzed Hydroformylation, ed. by P. W. N. M. van Leeuwen and C. Claver, Kluwer Academic Publishers 2006, A A Dordrecht, NL, pages 45-46, table 2, describes the hydroformylation results for the two ligands under comparable conditions. In this context, it is clearly apparent that the symmetric biphephos ligand (in the reference ligand 5a) features a much higher n/i selectivity and a higher activity than its unsymmetric isomer (in the reference ligand 7). In the hydroformylation reaction of propene, the symmetric ligand has an n/i selectivity of 53 and a reaction rate of 402, whereas the unsymmetric ligand has only an n/i selectivity of 1.2 and a reaction rate of 280.

These unsymmetric bisphosphites, when used as a ligand in transition metal-catalysed hydroformylation, thus have much lower reactivities and lower n-regioselectivity; see Rhodium-catalyzed Hydroformylation, ed. by P. W. N. M.

van Leeuwen and C. Claver, Kluwer Academic Publishers 2006, A A Dordrecht, NL, pages 45-46.

As stated by van Leeuwen, the symmetric bisphosphites, as well as higher n/i selectivities, also have a greater reactivity. Aside from the aim of a high reactivity and n/i selectivity in relation to the unsaturated compounds to be carbonylated, the stability—specifically the service life—of the catalytically active composition, composed of the metal, ligands and further components having activating action used in each case, with regard to the bisphosphites used as ligands is a constant task in research. This is especially true with regard to olefin-containing mixtures, specifically in the hydroformylation of mixtures of linear olefins.

U.S. Pat. No. 5,364,950, and also U.S. Pat. No. 5,763,677 and "Catalyst Separation, Recovery and Recycling", edited by D. J. Cole-Hamilton, R. P. Tooze, 2006, NL, pages 25-26, describe the formation of what are called "poisoning phosphites" as secondary reactions or ligand degradation reactions. These "poisoning phosphites" form in the course of use of aryl phosphite-modified rhodium complexes during the hydroformylation reaction. In the course of ligand degradation here, an aryl group is exchanged for an alkyl group in the hydroformylation product.

As well as the formation of the unwanted "poisoning phosphites", the phosphite ligand can also be degraded in the course of a hydrolysis reaction by the water traces formed in aldehyde condensation.

A consequence of these degradation reactions of the ligands is that the concentration of hydroformylation-active rhodium complex species decreases over the course of time and is accompanied by a loss of reactivity. It is common knowledge that, in a continuous mode of hydroformylation, ligand(s) and optionally further components have to be replenished during the course of the reaction, i.e. have to be added additionally after commencement of the reaction (see DE 10 2008 002 187 A1).

The technical object of the invention is the provision of a novel ligand which does not have the above-detailed disadvantages from the prior art in the hydroformylation of unsaturated compounds, but instead has the following properties:

1) a high activity,
2) a high n-regioselectivity in relation to the hydroformylation,
3) a high service life and long-term stability.

A high service life means that the hydroformylation-active composition comprising the ligand in addition to further components has a low tendency to degradation of this ligand and/or to decomposition of this ligand in hydroformylation-inhibiting components, for example the "poisoning phosphites".

The object is achieved by a compound of formula (1):

(1)

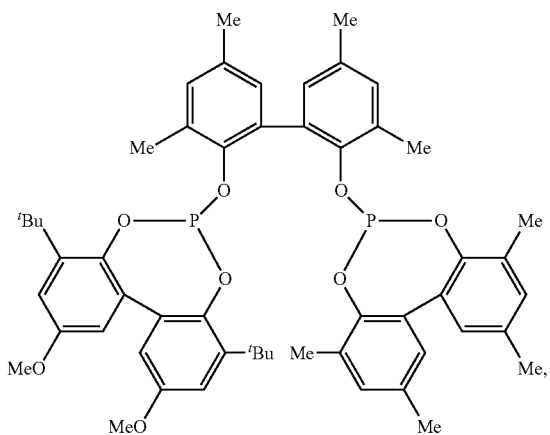 [SMILES: COc1cc(C(C)(C)C)c2op(Oc3c(C)cc(C)cc3-c3cc(C)cc(C)c3Op3oc4c(C)cc(C)cc4c4cc(C)cc(C)c4o3)oc3c(C(C)(C)C)cc(OC)cc3c2c1]

The invention encompasses the following subjects:
a) a bisphosphite of unsymmetric structure;
b) processes for preparation thereof;
c) mixtures comprising at least one complex of the formula (2), where M is a metal of groups 4 to 10 of the Periodic Table of the Elements (Fe, Ru, Os, Co, Rh, Ir, Ni, Pd, Pt) and can enter into additional bonds, and the bisphosphite mentioned in a) not bonded to the metal M.

(2)

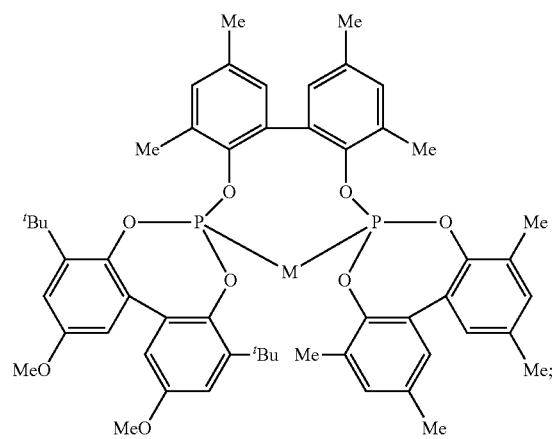

d) compositions comprising the bisphosphite mentioned under a), metal from groups 4 to 10 of the Periodic Table of the Elements (Fe, Ru, Os, Co, Rh, Ir, Ni, Pd, Pt) and free, i.e. unbound, bisphosphite and at least one further component selected from the group comprising bases, organic amines, epoxides, ion exchangers, buffer systems;

e) process for hydroformylating unsaturated compounds and mixtures thereof using compositions according to d), a gas mixture consisting of carbon monoxide and hydrogen, unsaturated compounds and mixtures thereof under the reaction conditions required for hydroformylation;

f) polyphasic reaction mixture consisting of:
f1) at least one composition according to d);
f2) a gas mixture consisting of carbon monoxide and hydrogen;
f3) at least one unsaturated compound as a substrate;
f4) at least one hydroformylation product formed from the substrates.

The process according to the invention for preparing the unsymmetric bisphosphite (1) comprises the steps of:
i) oxidatively coupling 2,4-dimethylphenol to give 3,3',5,5'-tetramethyl-2,2'-dihydroxybiphenyl;
ii) oxidatively coupling 3-tert-butyl-4-hydroxyanisole to give 5,5'-dimethoxy-3,3'-di-tert-butyl-2,2'-dihydroxybiphenyl;
iii) reacting 3,3',5,5'-tetramethyl-2,2'-dihydroxybiphenyl from i) with $PCl_3$ to give the phosphorochloridite derivative under inert gas atmosphere;
iv) reacting at least 2 equivalents of the phosphorochloridite derivative from iii) with 1 equivalent of the 5,5'-dimethoxy-3,3'-di-tert-butyl-2,2'-dihydroxybiphenyl from ii) under inert gas atmosphere.

In one variant of the process, a solvent mixture is used in process step iv).

In one variant of the process, the reaction in process step iv) is effected using an aprotic solvent mixture selected from organic nitrogen compounds, organic esters, aromatics.

In preferred variants of the process, the organic nitrogen compound is a compound selected from nitriles, amines, amides.

In particularly preferred variants of the process, a solvent selected from acetonitrile, triethylamine, dimethylaminobutane, diisopropylethylamine, N-methylpyrrolidone, pyridine, ethyl acetate, toluene is used in process step iv).

In particularly preferred variants of the process, process step iv) is effected in an aprotic polar solvent, or a mixture comprising at least one aprotic polar solvent.

The term "aprotic solvent" is understood in the context of this application to mean nonaqueous solvents which do not contain any ionizable proton in the molecule, and which are subdivided further into aprotic nonpolar and aprotic polar solvents (see Thieme Römpp online).

The term "aprotic nonpolar solvent" or "apolar aprotic solvent" encompasses aliphatic and aromatic, and also halogenated hydrocarbons (alkanes, alkenes, alkynes, benzene, aromatics with aliphatic or aromatic side chains), perhalogenated hydrocarbons such as carbon tetrachloride and hexafluorobenzene, tetramethylsilane and carbon disulphide.

Aprotic nonpolar solvents are characterized by low relative permittivities ($\epsilon r<15$), low dipole moments ($\mu<2.5$ D) and low ETN values (0.0-0.3; ETN=normalized values for the empirical parameters of solvent polarity). Aprotic nonpolar solvents are lipophilic and hydrophobic. There are van der Waals interactions between the molecules thereof.

The solvents encompassed by the term "aprotic polar solvents" or "dipolar aprotic solvents" have strongly polarizing functional groups and therefore exhibit a certain permanent dipole moment in addition to the van der Waals interactions, which are now of minor significance. The dissolution capacity thereof for polar substances is therefore generally better than that of the aprotic nonpolar solvents. Examples of aprotic polar solvents are ketones such as acetone, ethers, esters, N,N-disubstituted amides such as dimethylformamide, tertiary amines, pyridine, furan, thiophene, 1,1,1-trichloroethane, nitroalkanes such as nitromethane, nitriles such as acetonitrile, sulphoxides such as dimethyl sulphoxide, sulphones, hexamethylphosphoramide, liquid sulphur dioxide, selenium oxychloride. These have high permittivities ($\epsilon r>15$) and dipole moments ($\mu>2.5$ D), and ETN values in the range from 0.3-0.5.

One variant of the process according to the invention includes the additional process step v), in which the compound (1) is removed in solid form and suspended in an aprotic solvent mixture. In a further variant of process step v), the compound (1) removed in solid form is recrystallized in an aprotic solvent mixture.

In particularly preferred variants of the process according to the invention, process step v) is effected by suspension in acetonitrile at 75° C. or in toluene at 35° C.

In particularly preferred variants of the process according to the invention, process step v) is effected by recrystallization in an aprotic solvent mixture consisting of toluene/heptane or xylene/heptane.

As well as the compound of the formula (1), a compound of the formula (2) is also claimed. This encompasses the compound of the formula (1).

Compound of the Formula (2):

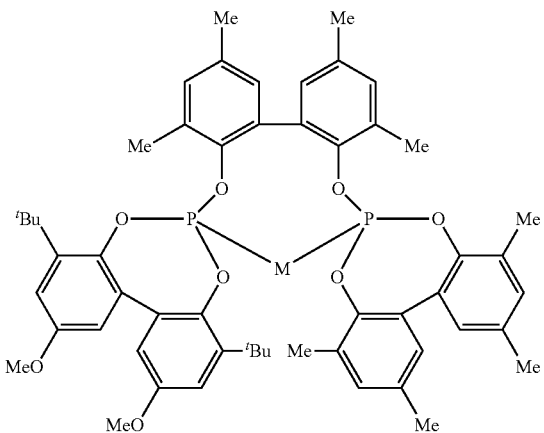

(2)

where M is selected from Fe, Ru, Os, Co, Rh, Ir, Ni, Pd, Pt, and M may enter into additional bonds.

Preference is given here to Co, Rh, Ru, Ir, Fe, and particular preference to Rh.

The compound of the formula (2) is formed in situ during the hydroformylation, as disclosed in the examples.

In a particular embodiment of the invention, the compound is of the formula (3):

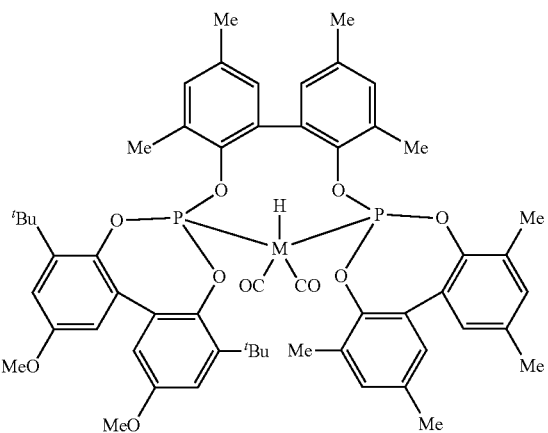

(3)

where M is selected from: Fe, Ru, Os, Co, Rh, Ir, Ni, Pd, Pt.

Preference is given here to Co, Rh, Ru, Ir, Fe, and particular preference to Rh.

As well as the pure compounds, mixtures comprising them are also claimed.

Mixtures comprise a compound of the formula (2) and/or (3), the mixture additionally comprising a compound of the formula (1) not coordinated to M.

As well as the mixtures, compositions are also claimed.

The compositions comprise an above-described mixture which, in addition to the mixture, include a further component selected from bases, organic amines, buffer solutions, ion exchangers, epoxides.

U.S. Pat. No. 4,567,306, U.S. Pat. No. 5,364,950, U.S. Pat. No. 5,741,942 and U.S. Pat. No. 5,763,677 disclose examples of these further components.

In a preferred embodiment, further components used are sterically hindered secondary amine compounds having the general formula I

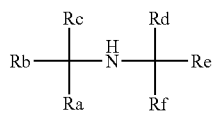

where Ra, Rb, Rc, Rd, Re and Rf are identical or different hydrocarbyl radicals which may also be joined to one another.

In a preferred embodiment, the organic amine has a structure as per formula Ia:

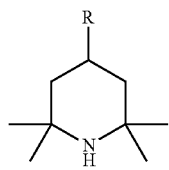

where R is H, like 2,2,6,6-tetramethylpiperidine itself, an organic radical R, a hydroxyl group or a halogen.

The organic radical R may also be an organic radical bonded via a heteroatom, for example an oxygen atom, to the 2,2,6,6-tetramethylpiperidine structural unit. More particularly, the organic radical may have polymeric structures or be an organic radical having 1 to 50 carbon atoms and optionally heteroatoms. More preferably, the organic radical has carbonyl groups, such as keto, ester or acid amide groups. The organic radical optionally having heteroatoms may especially be a substituted or unsubstituted, aliphatic, alicyclic, aliphatic-alicyclic, heterocyclic, aliphatic-heterocyclic, aromatic, aromatic-aromatic or aliphatic-aromatic hydrocarbyl radical having 1 to 50 carbon atoms, where the substituted hydrocarbyl radicals may have substituents selected from primary, secondary or tertiary alkyl groups, alicyclic groups, aromatic groups, —N(R$^1$)$_2$, —NHR$^1$, —NH$_2$, fluorine, chlorine, bromine, iodine, —CN, —C(O)—R$^1$, —C(O)H or —C(O)O—R$^1$, —CF$_3$, —O—R$^1$, —C(O)N—R$^1$, —OC(O)—R$^1$ and/or —Si(R$^1$)$_3$, where R$^1$ is a monovalent hydrocarbyl radical having preferably 1 to 20 carbon atoms. If a plurality of hydrocarbyl radicals R$^1$ are present, these may be the same or different. The substituents are preferably limited to those which have no influence on the reaction itself. Particularly preferred substituents may be selected from the halogens, for example chlorine, bromine or iodine, the alkyl radicals, for example methyl, ethyl, propyl, isopropyl, butyl, sec-butyl, t-butyl, neopentyl, sec-amyl, t-amyl, isooctyl, t-octyl, 2-ethylhexyl, isononyl, isodecyl or octadecyl, the aryl radicals, for example phenyl, naphthyl or anthracyl, the alkylaryl radicals, for example tolyl, xylyl, dimethylphenyl, diethylphenyl, trimethylphenyl, triethylphenyl or p-alkylphenyl, the aralkyl radicals, for example benzyl or phenylethyl, the alicyclic radicals, for example cyclopentyl, cyclohexyl, cyclooctyl, cyclohexylethyl or 1-methylcyclohexyl, the alkoxy radicals, for example methoxy, ethoxy, propoxy, butoxy or pentoxy, the aryloxy radicals, for example phenoxy or naphthoxy, —OC(O)R$^1$ or —C(O)R$^1$, for example acetyl, propionyl, trimethylacetoxy, triethylacetoxy or triphenylacetoxy, and the silyl radicals having three hydrocarbyl radicals —Si(R$^1$)$_3$, for example trimethylsilyl, triethylsilyl or triphenylsilyl. Particular preference is given to compounds of the formula IIa having, as R radicals, those which contain a 2,2,6,6-tetramethylpiperidine radical and optionally a further —N(R$^1$)$_2$, —NHR$^1$ and/or —NH$_2$ group.

As secondary amines having a structural unit as per formula I, it is possible with very particular preference to use the compounds listed hereinafter having the structural formulae Ib to Ig or derivatives thereof.

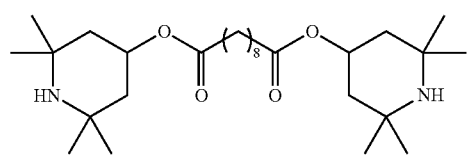

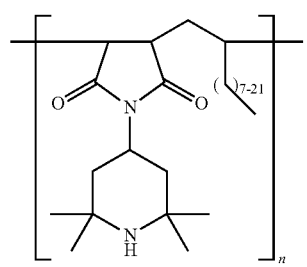

where n=1 to 20, preferably 1 to 10

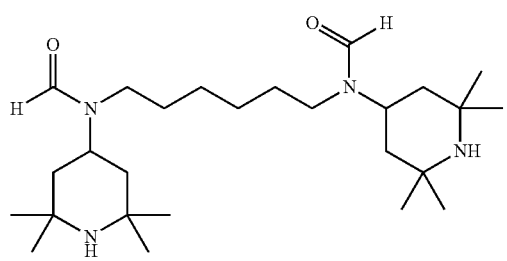

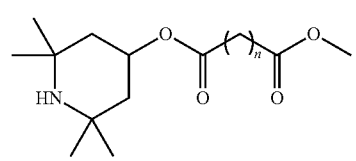

where n=1 to 12, preferably 8

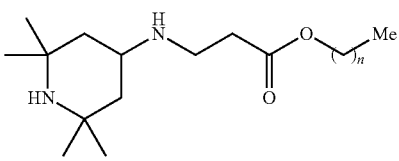

where n=1 to 17, preferably 13

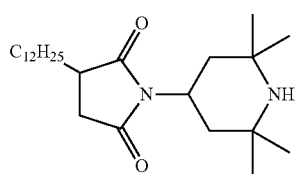

It is also possible to use mixtures comprising two or more sterically hindered amines. The composition comprises an above-described mixture including, in addition to the mixture, at least one amine having a 2,2,6,6-tetramethylpiperidine unit.

More particularly, in the process according to the invention, the amine having the formula Ib, di-4-(2,2,6,6-tetramethylpiperidinyl) sebacate, is used with preference.

A particularly preferred metal in the inventive composition is rhodium.

Additionally claimed is a process for hydroformylating unsaturated compounds and mixtures thereof, which uses these compositions.

Process for hydroformylating an unsaturated compound or a mixture of unsaturated compounds, comprising the process steps of:

a) initially charging a compound of the formulae (1), (2) and/or (3) or composition comprising the compounds of the formulae (1), (2) and (3) together with a further component selected from bases, organic amines, buffer solutions, ion exchangers, epoxides, b) introducing a gas mixture comprising carbon monoxide and hydrogen, c) adding at least one unsaturated compound or a mixture of unsaturated compounds.

The unsaturated compounds which are hydroformylated in the process according to the invention include hydrocarbon mixtures obtained in petrochemical processing plants. Examples of these include what are called $C_4$ cuts. Typical compositions of $C_4$ cuts from which the majority of the polyunsaturated hydrocarbons has been removed and which can be used in the process according to the invention are listed in table 1 below (see DE 10 2008 002188).

TABLE 1

| Component | Steamcracking plant | | Steamcracking plant | | Catalytic cracking plant | |
| --- | --- | --- | --- | --- | --- | --- |
| | $HCC_4$ | $HCC_4$/ SHP | Raff. I | Raff. I/ SHP | $CC_4$ | $CC_4$/ SHP |
| isobutane [% by mass] | 1-4.5 | 1-4.5 | 1.5-8 | 1.5-8 | 37 | 37 |
| n-butane [% by mass] | 5-8 | 5-8 | 6-15 | 6-15 | 13 | 13 |
| E-2-butene [% by mass] | 18-21 | 18-21 | 7-10 | 7-10 | 12 | 12 |
| 1-butene [% by mass] | 35-45 | 35-45 | 15-35 | 15-35 | 12 | 12 |
| isobutene [% by mass] | 22-28 | 22-28 | 33-50 | 33-50 | 15 | 15 |
| Z-2-butene [% by mass] | 5-9 | 5-9 | 4-8 | 4-8 | 11 | 11 |
| 1,3-butadiene [ppm by mass] | 500-8000 | 0-50 | 50-8000 | 0-50 | <10000 | 0-50 |

Key:
$HCC_4$: typical of a $C_4$ mixture which is obtained from the $C_4$ cut from a steamcracking plant (high severity) after the hydrogenation of the 1,3-butadiene without additional moderation of the catalyst.
$HCC_4$/SHP: $HCC_4$ composition in which residues of 1,3-butadiene have been reduced further in a selective hydrogenation process/SHP.
Raff. I (raffinate I): typical of a $C_4$ mixture which is obtained from the $C_4$ cut from a steamcracking plant (high severity) after the removal of the 1,3-butadiene, for example by an NMP extractive rectification.
Raff. I/SHP: raff. I composition in which residues of 1,3-butadiene have been reduced further in a selective hydrogenation process/SHP.
$CC_4$: typical composition of a $C_4$ cut which is obtained from a catalytic cracking plant.
$CC_4$/SHP: composition of a $C_4$ cut in which residues of 1,3-butadiene have been reduced further in a selective hydrogenation process/SHP.

In one variant of the process, the unsaturated compound or mixture thereof in c) has been selected from:
hydrocarbon mixtures from steamcracking plants;
hydrocarbon mixtures from catalytically operated cracking plants, for example FCC cracking plants;
hydrocarbon mixtures from oligomerization operations in homogeneous phase and heterogeneous phases, for example the OCTOL, DIMERSOL, Fischer-Tropsch, Polygas, CatPoly, InAlk, Polynaphtha, Selectopol, MOGD, COD, EMOGAS, NExOCTANE or SHOP process;
hydrocarbon mixtures comprising polyunsaturated compounds;
unsaturated carboxylic acid derivatives.

In one variant of the process, the mixture includes unsaturated compounds having 2 to 30 carbon atoms.

In one variant of the process, the mixture includes unsaturated compounds having 2 to 8 carbon atoms.

In a further variant of the process, the mixture includes polyunsaturated hydrocarbons. In a particular embodiment, the mixture comprises butadiene.

The unsaturated compounds which are hydroformylated in the process according to the invention additionally include unsaturated carboxylic acid derivatives. In a particular embodiment, these unsaturated carboxylic acid derivatives are selected from fatty acid esters.

The process according to the invention is performed in different embodiments which are disclosed in detail in the examples.

The inventive polyphasic reaction mixture comprises, as well as a gas mixture consisting of carbon monoxide and hydrogen, at least one unsaturated compound as disclosed above, and comprises, as well as hydrocarbon mixtures which originate from steamcracking, catalytically operated cracking plants or oligomerization operations, or contain other sources of monounsaturated and/or polyunsaturated carbon compounds or unsaturated carboxylic acid derivatives, at least one hydroformylation product of these unsaturated compounds as detailed in the examples which follow, and the composition used in each case, as disclosed above.

DESCRIPTION OF FIGURES

Calculation of the Complex (3)

The inventive complexes of the formulae (2) and (3) are formed in situ during the hydroformylation reaction.

In a particular embodiment of the invention, the complexes (2) and (3) are present alongside the unbound bisphosphite (1).

Figures 1, 2:
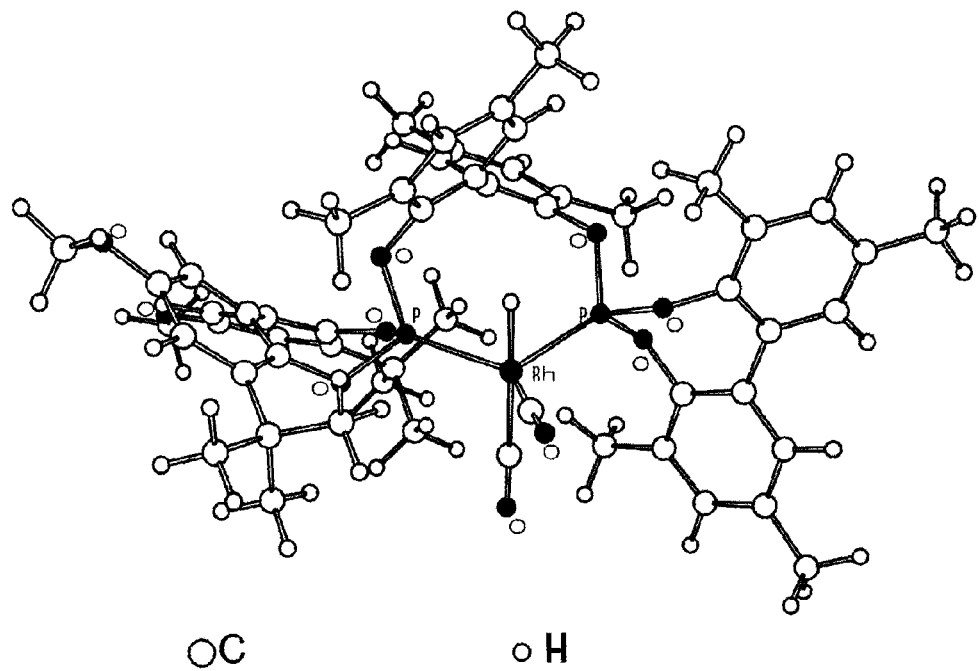
FIG. 1 shows the hydridocarbonyl complex of the ligand (1), with rhodium as the metal, of the inventive compound (3).
FIG. 2 shows all the coordinates, distances and angles calculated for the compound (3).

The hydridocarbonyl complex of the ligand (1), with rhodium as the metal, of the inventive compound (3) was characterized by means of theoretical calculations. The result is shown in FIG. 1 in the appendix.

The structure calculation was conducted with the BP86 functional and the def-SV(P) base set.

The structure calculations for the model structures were effected with the Turbomole program package (R. Ahlrichs, M. Bär, M. Haser, H. Horn, C. Kölmel, Chem. Phys. Lett., 1989, 162, 16; TURBOMOLE V6.3 2011, a development of University of Karlsruhe and Forschungszentrum Karlsruhe GmbH, 1989-2007, TURBOMOLE GmbH, since 2007.

http://www.turbomole.com) on the basis of density functional theory (DFT). The BP86 functional (S. H. Vosko, L. Wilk, M. Nusair, Can. J. Phys., 1980, 58, 1200; A. D. Becke, Phys. Rev. A, 1988, 38, 3098; J. Perdew, Phys. Rev. B, 1986, 33, 8822) and the def-SV(P) base set (A. Schäfer, H. Horn and R. Ahlrichs, J. Chem. Phys., 1992, 97, 2571) were used.

FIG. 2 in the appendix shows all the coordinates, distances and angles calculated for the compound (3).

Figure 3:
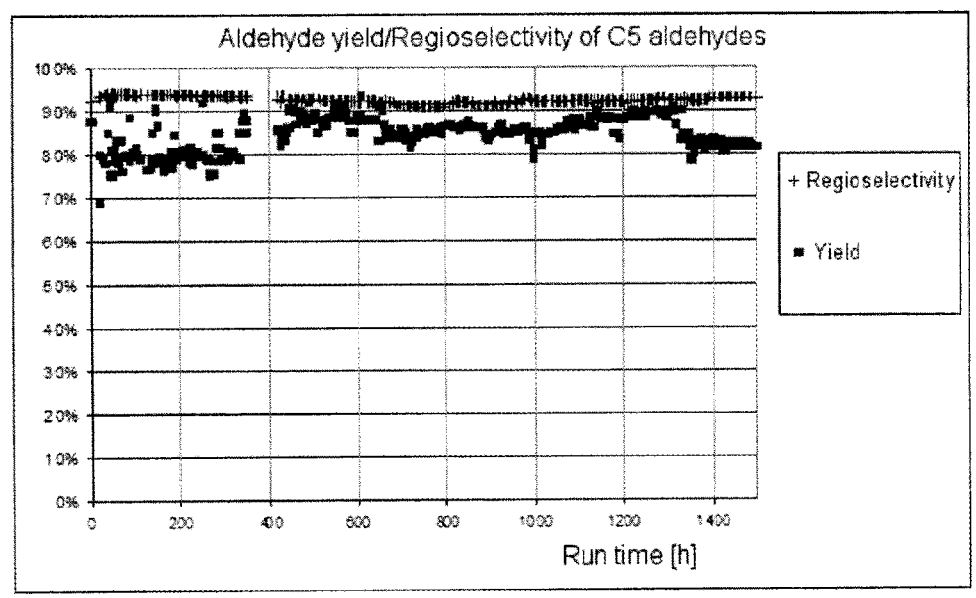
FIG. 3 shows hydroformylation experiments in a continuously operated experiment system.
Figure 4:
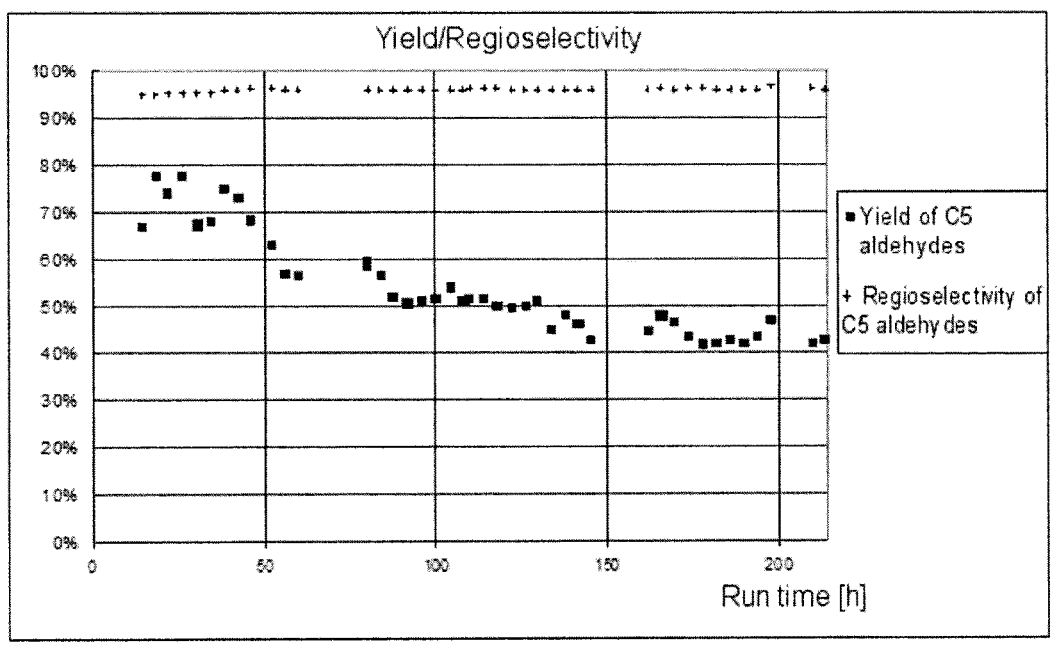
FIG. 4 shows hydroformylation experiments in a continuously operated experiment system.

FIGS. 3 and 4 show hydroformylation experiments in a continuously operated experiment system. In a first experiment series (FIG. 3), the inventive compound (1) was tested. Under the selected reaction conditions, an aldehyde yield between 80% and 90% was established. It was possible to keep this state constant up to the end of the experiment. The percentage distribution between n-pentanal and 2-methylbutanal, i.e. the regioselectivity, was 92% to 8%.

catalyzed Hydroformylation, ed. by P. W. N. M. van Leeuwen and C. Claver, Kluwer Academic Publishers 2006, A A Dordrecht, NL, pages 45-46.

The inventive ligand (1) in the catalytically active composition features much better long-term stability than the ligands described in the prior art to date and thus achieves the stated object. An optimal long-term stability of the catalytically active composition is of significance especially in industrial scale use, since the ligand in the hydroformylation reaction can be replenished on the industrial scale, but any replenishment adversely affects the economic viability of an industrial scale process and may make it unfeasible.

EXAMPLES

General Reaction Equation

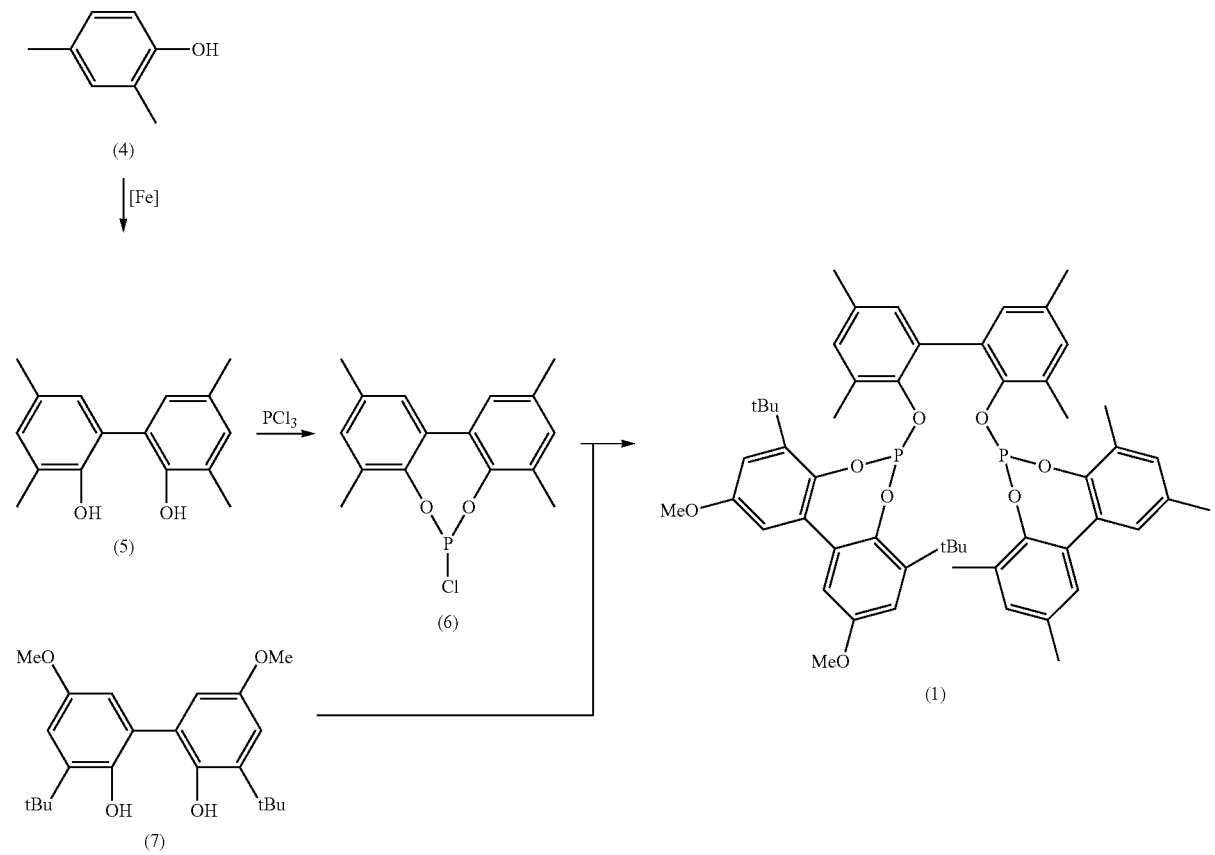

In the second experiment series (FIG. 4), the comparative compound biphephos was used under the same experimental conditions. Under the reaction conditions selected, the aldehyde yield fell from initially 70% to 80% after 150 h to 40% to 50%. The percentage distribution between n-pentanal and 2-methylbutanal, i.e. the regioselectivity, was 95% to 5%. In other words, this ligand features a much lower long-term stability than the inventive ligand (1). However, this is crucial for an industrial scale operation, since it strongly influences the economic viability of such an operation.

Consequently, the inventive ligand features a distinct improvement in stability and activity. This result is surprising, since unsymmetric substituted bisphosphites show distinct losses of activity and selectivity compared to symmetrically substituted examples, as already stated in Rhodium-

ABBREVIATIONS

DM water=demineralized water
CPG=core-pulled precision glass
ACN=acetonitrile
EtOAc=ethyl acetate
acac=acetylacetonate
NEt$_3$=triethylamine
TIPB=1,2,4,5-tetraisopropylbenzene Synthesis of 2,2'-bis(3,5-dimethylphenol) (5)

The biphenol (5) used as a precursor was prepared by the synthesis method which follows.

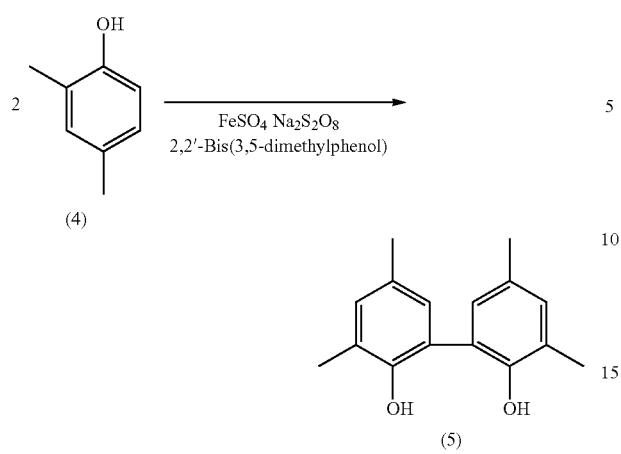

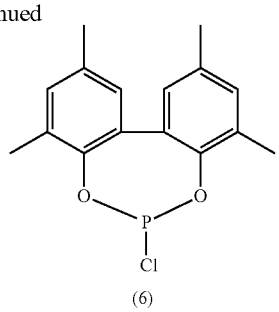

A 500 ml Schlenk with CPG stirrer, intermediate section and glass stirrer was initially charged with 1.42 g (0.005 mol) of iron(II) sulphate heptahydrate and 12.35 g (0.1 mol) of 2,4-dimethylphenol in 150 ml of DM water and 5 ml of cyclohexane, and the mixture was heated to 40° C.

In a 100 ml beaker, 25.36 g (0.146 mol) of sodium peroxodisulphate were dissolved in 80 ml of DM water. At the start of the reaction, a small portion of $Na_2S_2O_8$ solution was added to the phenol. Subsequently, a smaller portion of the solution was added every 10 min. After 30 min, the addition of $Na_2S_2O_8$ solution had ended.

After a reaction time of 5 h, 300 ml of cyclohexane and 200 ml of water were added to the reaction solution, which was left to stir for 20 min, then transferred while warm into a separating funnel.

The organic phase was removed and concentrated to dryness. The product (5) was obtained in 69% yield (10.6 g).

All the preparations which follow were conducted with standard Schlenk technology under protective gas. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

The products were characterized by means of NMR spectroscopy. Chemical shifts (□) are reported in ppm. The $^{31}$P NMR signals were referenced according to: $SR_{31P}=SR_{1H}*BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl. Chem., 2008, 80, 59-84). By means of $^{31}$P NMR, the content of the ligand (1) was determined, with characterization of this unsymmetric ligand by two phosphorus signals.

Synthesis of 2,2'-bis(3,5-dimethylphenol) chlorophosphite (6)

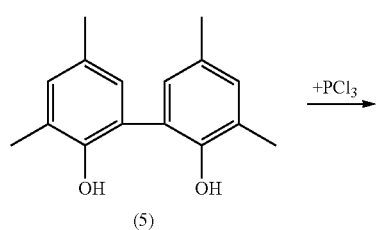

A secured 2 l Schlenk with magnetic stirrer was initially charged with 440 ml of phosphorus trichloride. 120 g of 2,2-bis(3,5-dimethylphenol) were weighed into a second secured 1 l Schlenk and 500 ml of dried toluene were added while stirring. The biphenol-toluene suspension was metered into the phosphorus trichloride at 63° C. within 4 h. On completion of addition, the reaction mixture was stirred at temperature overnight. The next morning, the solution was concentrated while warm (45° C.), and the product was obtainable in 96.5% yield (153 g). $^{31}$P NMR: 175.59 (94.8% 2,2'-bis(3,5-dimethylphenol) chlorophosphite), 4.4% various PCl compounds, 0.8% P—H compound.

Inventive Synthesis Variations for Preparation of the Pure Ligand (1)

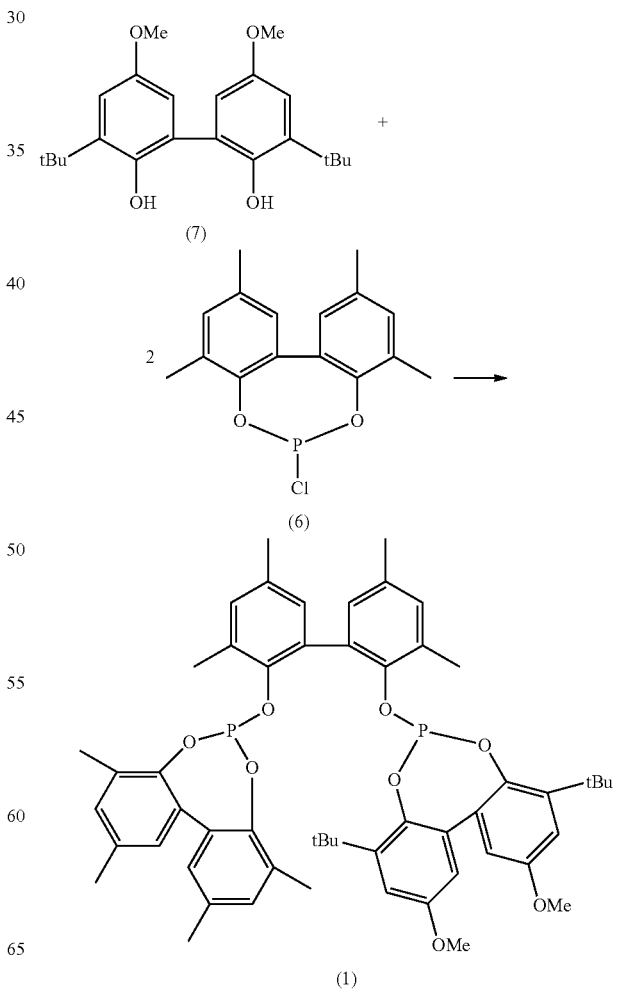

Variant 1: ACN/NEt$_3$

In a 1000 ml Schlenk, under protective gas, 38.75 g (0.121 mol) of 2,2'-bis(3,5-dimethylphenol) chlorophosphite were dissolved in 150 ml of degassed ACN and heated to 35° C. In a second Schlenk (500 ml), 20.1 g (0.056 mol) of 3,3'-di-tert-butyl-5,5'-dimethoxy-[1,1'-biphenyl]-2,2'-diol were dissolved in 150 ml of degassed ACN, and 40.9 ml of degassed triethylamine (0.29 mol) were added while stirring. Then the biphenol/triethylamine solution was slowly added dropwise to the chlorophosphite solution. After a further reaction time of 1 h, the reaction solution was stirred at 45° C. overnight.

These solids were suspended in degassed ACN at 75° C. for 1.5 h and removed and washed with warm ACN. Subsequently, the product was suspended in dried toluene at 35° C. for 1.5 h and washed. The target product (1) was obtained as a white solid (33 g, 66%). $^{31}$P NMR (202.4 MHz, toluene-d$_8$): 142.5 and 140.9 (100%).

Variant 2: EtOAc/NEt$_3$

In a 100 ml Schlenk, under protective gas, 7.3 g (21.0 mmol) of 2,2'-bis(3,5-dimethylphenol) chlorophosphite were dissolved in 15 ml of degassed ethyl acetate and heated to 35° C. In a second Schlenk (100 ml), 3.9 g (9.5 mmol) of 3,3'-di-tert-butyl-5,5'-dimethoxy-[1,1'-biphenyl]-2,2'-diol were dissolved in 7.0 ml of NEt$_3$. Subsequently, the biphenol/triethylamine solution was slowly added dropwise to the chlorophosphite solution within 20 minutes. The solution was stirred at 35° C. for a further hour and then at 45° C. overnight.

These solids were suspended in degassed ACN at 75° C. for 1.5 h and removed and washed with warm ACN. Subsequently, the product was suspended in dried toluene at 35° C. for 1.5 h and removed.

The target product (1) was obtained as a white solid (5.0 g, 58%). $^{31}$P NMR (202.4 MHz, toluene-d$_8$): 142.5 and 140.9 (100%).

Variant 3: EtOAc/Pyridine

In a 250 ml Schlenk, under protective gas, 10.07 g (31.0 mmol) of 2,2'-bis(3,5-dimethylphenol) chlorophosphite were dissolved in 20 ml of degassed ethyl acetate and heated to 45° C. In a second Schlenk (50 ml), 5.54 g (15 mmol) of 3,3'-di-tert-butyl-5,5'-dimethoxy-[1,1'-biphenyl]-2,2'-diol were dissolved in 26 ml of ethyl acetate and 5.2 ml of degassed pyridine. Subsequently, the biphenol/pyridine solution was slowly added dropwise to the chlorophosphite solution within 30 minutes. The solution was stirred at 45° C. overnight.

The next day, the solution was filtered and the solids were washed with ACN. The target product was obtainable as a white solid (4.2 g, 31%). $^{31}$P NMR (202.4 MHz, toluene-d$_8$): 142.2 and 141.1 (100%).

Variant 4: Performance of a Low-Temperature Experiment at −20° C.

In a 250 ml Schlenk, under protective gas, 8.0 g (0.025 mol) of 2,2'-bis(3,5-dimethylphenol) chlorophosphite were dissolved in 30 ml of degassed ACN and cooled to −20° C. In a second Schlenk (100 ml), 4.32 g (0.012 mol) of 3,3'-di-tert-butyl-5,5'-dimethoxy-[1,1'-biphenyl]-2,2'-diol were dissolved in 30 ml of degassed ACN, and 8.5 ml of degassed triethylamine were added while stirring. Then the biphenol/triethylamine solution was slowly added dropwise at −20° C. to the chlorophosphite solution. On completion of addition, stirring was continued at −20° C. for a further 4 hours. The reaction solution was stirred overnight at −10° C. until the next day. This procedure, reaction temperature at −20° C. through the day and at −10° C. overnight, was conducted repeatedly for 3 days. Thereafter, the reaction mixture was brought to RT within 3 hours.

Subsequently, the solution was filtered and the solids were washed with cold ACN. The target product was obtainable as a white solid (7.6 g, 70%). $^{31}$P NMR (202.4 MHz, toluene-d$_8$): 142.5 and 140.9 (100%).

The unsymmetric bisphosphite (1) was thus obtained, completely surprisingly and contrary to the prior art, in good yields and excellent purity even at low temperatures.

Purification of the Ligand (1):

As well as the suspending of the ligand in various solvents (see example above), it is also possible to purify the ligand by means of recrystallization. This recrystallization was effected to WO 2012095255. Rather than o-xylene, it is also possible to use toluene for recrystallization in an analogous manner.

Procedure for the Hydroformylation Experiments

Experiment Description—General

The experiments were conducted in 100 ml autoclaves from Parr Instruments. The autoclaves are equipped with an electric heater. The pressure is kept constant by means of mass flow meters and pressure regulators. During the experiment duration, a syringe pump can be used to inject an exactly defined amount of reactant under reaction conditions. Capillary lines and HPLC valves can be used to take samples during the experiment duration, and these can be analysed both by means of GC analysis and by means of LC-MS analysis.

Experiment Description—Extended Experiment

The Rh precursor (Rh(acac)(CO)$_2$) (acac=acetylacetonate) and the ligand are initially charged in 40 ml of isononyl benzoate in an autoclave. The Rh concentration is 100 ppm based on the overall reaction mixture used. The ligand excess used is 4:1 in molar terms, based on rhodium.

As a further component in a ratio of 2:1 to the ligand, compound (Ib) is added as the amine. As a GC standard, 0.5 g of 1,2,4,5-tetraisopropylbenzene is added.

Reaction temperature is 120° C. The reaction pressure is 20 bar of synthesis gas (H$_2$:CO=50:50% by volume).

As the olefin, 4 ml of cis-2-butene each time were metered in with the syringe pump at intervals of about 1 day. GC samples were taken after 1, 2, 4 hours and before the next metered addition.

The following ligands were studied with regard to their stability:

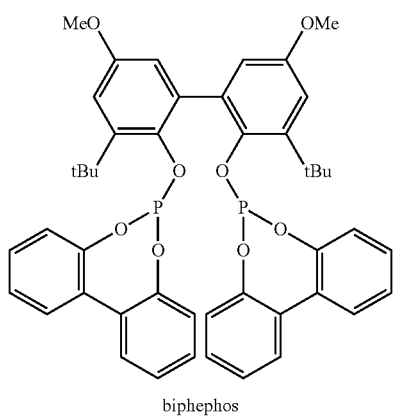 [SMILES: COc1cc(-c2cc(OC)cc(C(C)(C)C)c2Op2oc3ccccc3c3ccccc3o2)c(Op2oc3ccccc3c3ccccc3o2)c(C(C)(C)C)c1]

biphephos

-continued

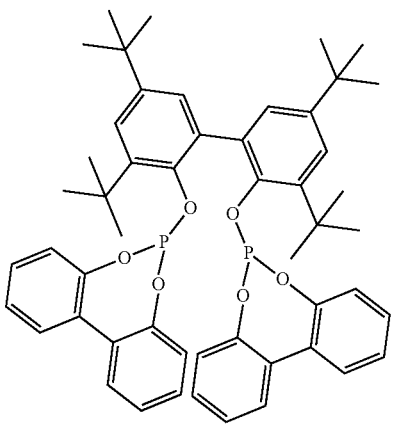

(8)

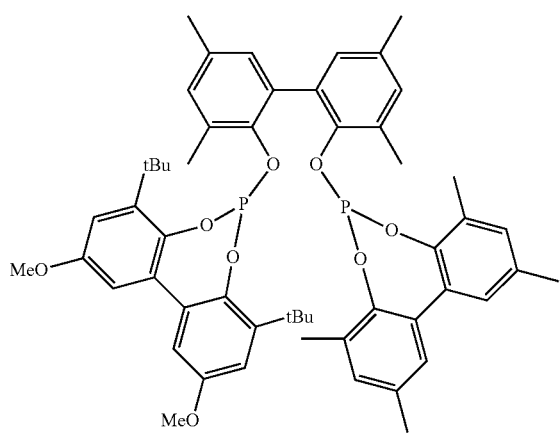

(1)

Results—Extended Experiments

The relative activities are determined by the ratio of 1st order k to k0, i.e. the k value at time 0 in the reaction (start of reaction), and describe the relative decrease in activity during the experiment duration.

The 1st order k values are obtained from a plot of (−ln(1-conversion)) against time.

TABLE 2

| Ser. No. | Ligand | Metered addition at Run time (h) | 1st order k (min⁻¹) | k/k0 Rel. activity | n/i selectivity |
|---|---|---|---|---|---|
| 1 | biphephos | 0 | 1.39E−02 | 1 | 21 |
| 2 | biphephos | 20.5 | 4.45E−03 | 0.32 | 21 |
| 3 | biphephos | 44.3 | 2.91E−03 | 0.209 | 20 |
| 4 | biphephos | 66.6 | 1.72E−03 | 0.124 | 20 |
| 5* | ligand (1) | 0 | 7.74E−03 | 1 | 17 |
| 6* | ligand (1) | 20.8 | 5.10E−03 | 0.659 | 16 |
| 7* | ligand (1) | 44.8 | 3.19E−03 | 0.412 | 15 |
| 8* | ligand (1) | 117.8 | 2.99E−03 | 0.386 | 14 |
| 9 | ligand (8) | 0 | 1.72E−02 | 1 | 14 |
| 10 | ligand (8) | 22.4 | 9.00E−03 | 0.523 | 13 |
| 11 | ligand (8) | 44.7 | 5.39E−03 | 0.313 | 13 |
| 12 | ligand (8) | 68.3 | 3.31E−03 | 0.192 | 13 |

*inventive

Result: The decline in catalyst activity with the biphephos ligand and ligand (8) is (Table 2; entries 1-4, 9-12) much more marked than with the ligand (1). It is remarkable that the relative activity of the ligand (1) after nearly twice the reaction time (Table 2; entry 8) is still more than twice as high as for the other two ligands after half the reaction time (Table 2; entries 4 and 12), still with very good n/i selectivities. This behaviour is confirmed in the extended experiments in the continuously operated hydroformylation plant (see FIGS. 3 and 4).

It was thus possible to prepare an unsymmetric ligand and use it in a hydroformylation-active composition, and this ligand, completely surprisingly and contrary to the prior art, has very good properties and achieves the technical object.

Inventive Results

Substrate Variation

Example 1

In a 100 ml autoclave from Parr Instruments, 5.3 g of propene were hydroformylated at 120° C. and 30 bar. As the precursor, 0.0054 g of Rh(acac)(CO)$_2$ was initially charged in 43.89 g of toluene. As the ligand, 0.0701 g of ligand (1) was used in the catalyst mixture solution. 0.0372 g of the compound (Ib) was added as the organic amine, and 0.5016 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. 89.6 mol % butanal, 7.9 mol % 2-methylpropanal and 2.3 mol % propane were formed. The regioselectivity for n-butanal is 92.0%.

Example 2

In a 100 ml autoclave from Parr Instruments, 5.6 g of cis-2-butene were hydroformylated at 120° C. and 20 bar. As the precursor, 0.0056 g of Rh(acac)(CO)$_2$ was initially charged in 48.8 g of toluene. As the ligand, 0.0779 g of ligand (1) was used in the catalyst mixture solution. 0.0416 g of the compound (Ib) was added as the organic amine, and 0.5760 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 20 hours. 80.0 mol % pentanal, 5.2 mol % 2-methylbutanal and 3.7 mol % n-butane were formed. The regioselectivity for n-pentanal is 94.0%.

Example 3

In a 100 ml autoclave from Parr Instruments, 6.3 g of isobutene were hydroformylated at 120° C. and 20 bar. As the precursor, 0.0046 g of Rh(acac)(CO)$_2$ was initially charged in 39.8 g of toluene. As the ligand, 0.0636 g of ligand (1) was used in the catalyst mixture solution. 0.0339 g of the compound (Ib) was added as the organic amine, and 0.4701 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. 72.9 mol % 3-methylbutanal, 0.1 mol % pivalaldehyde and 4.4 mol % isobutane were formed.

Example 4

In a 100 ml autoclave from Parr Instruments, 6.7 g of a C-4 mixture having the following composition: 2.9 mol % isobutane, 9.9 mol % n-butane, 28.7 mol % 1-butene, 43.5 mol % isobutene, 14.6 mol % 2-butenes and 0.2 mol %

1,3-butadiene were hydroformylated at 120° C. and 20 bar. As the precursor, 0.0049 g of Rh(acac)(CO)$_2$ was initially charged in 42.38 g of toluene. As the ligand, 0.0697 g of ligand (1) was used in the catalyst mixture solution. 0.0374 g of the compound (Ib) was added as the organic amine, and 0.5069 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 32.86% 3-methylbutanal (isobutene conversion 75.6 mol %), 39.0 mol % n-pentanal and 1.8 mol % 2-methylbutanal (butenes conversion 76.5 mol %, regioselectivity for n-pentanal 95.6%). As hydrogenation products, 4.7 mol % isobutane and 11.3 mol % n-butane were found in the output.

Example 5

In a 100 ml autoclave from Parr Instruments, 6.5 g of a C-4 mixture having the following composition: 5.9 mol % isobutane, 15.6 mol % n-butane, 52.9 mol % 1-butene, 0.1 mol % isobutene, 24.8 mol % 2-butenes and 0.5 mol % 1,3-butadiene were hydroformylated at 120° C. and 20 bar. As the precursor, 0.0052 g of Rh(acac)(CO)$_2$ was initially charged in 45.05 g of toluene. As the ligand, 0.0727 g of ligand (1) was used in the catalyst mixture solution. 0.0377 g of the compound (Ib) was added as the organic amine, and 0.5314 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 0.14 mol % 3-methylbutanal, 69.5 mol % n-pentanal and 3.67 mol % 2-methylbutanal (butenes conversion 94.2 mol %, regioselectivity for n-pentanal 96.5%). As hydrogenation products, 5.64 mol % isobutane and 18.55 mol % n-butane were found in the output.

Example 6

In a 100 ml autoclave from Parr Instruments, 7.0 g of a C-4 mixture having the following composition: the reactant comprises 5.9 mol % isobutane, 22.1 mol % n-butane, 45.5 mol % 1-butene, 2.1 mol % isobutene, 17.1 mol % 2-butenes and 0.2 mol % 1,3-butadiene were hydroformylated at 120° C. and 20 bar. As the precursor, 0.0047 g of Rh(acac)(CO)$_2$ was initially charged in 40.81 g of toluene. As the ligand, 0.0659 g of ligand (1) was used in the catalyst mixture solution. 0.0342 g of the compound (Ib) was added as the organic amine, and 0.4814 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 1.5 mol % 3-methylbutanal (isobutene conversion 71.6 mol %), 61.9 mol % n-pentanal and 2.9 mol % 2-methylbutanal (butenes conversion 93.3 mol %, regioselectivity for n-pentanal 95.5%). As hydrogenation products, 5.3 mol % isobutane and 23.4 mol % n-butane were found in the output.

Example 7

In a 100 ml autoclave from Parr Instruments, 7.1 g of a C-4 mixture having the following composition: 3.5 mol % isobutane, 13.0 mol % n-butane, 47.3 mol % 1-butene, 13.9 mol % isobutene, 21.6 mol % 2-butenes and 0.4 mol % 1,3-butadiene were hydroformylated at 120° C. and 20 bar. As the precursor, 0.0048 g of Rh(acac)(CO)$_2$ was initially charged in 43.88 g of toluene. As the ligand, 0.0680 g of ligand (1) was used in the catalyst mixture solution. 0.0363 g of the compound (Ib) was added as the organic amine, and 0.5092 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 10.1 mol % 3-methylbutanal (isobutene conversion 72.8 mol %), 63.2 mol % n-pentanal and 3.2 mol % 2-methylbutanal (butenes conversion 96.3 mol %, regioselectivity for n-pentanal 95.2%). As hydrogenation products, 3.5 mol % isobutane and 15.1 mol % n-butane were found in the output.

Example 8

In a 100 ml autoclave from Parr Instruments, 5.8 g of a C-4 mixture having the following composition: 0.1 mol % isobutane, 27.6 mol % n-butane, 27.9 mol % 1-butene, 0.1 mol % isobutene and 44.0 mol % 2-butenes were hydroformylated at 120° C. and 20 bar. As the precursor, 0.0051 g of Rh(acac)(CO)$_2$ was initially charged in 43.77 g of toluene. As the ligand, 0.0699 g of ligand (1) was used in the catalyst mixture solution. 0.0373 g of the compound (Ib) was added as the organic amine, and 0.5166 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 59.9 mol % n-pentanal and 3.3 mol % 2-methylbutanal (butenes conversion 91.7 mol %, regioselectivity for n-pentanal 94.7%). As hydrogenation products, 0.1 mol % isobutane and 31.7 mol % n-butane were found in the output.

Example 9

In a 100 ml autoclave from Parr Instruments, 6.0 g of a C-4 mixture having the following composition: 63.6 mol % n-butane, 1.0 mol % 1-butene and 35.8 mol % 2-butenes were hydroformylated at 120° C. and 20 bar. As the precursor, 0.0041 g of Rh(acac)(CO)$_2$ was initially charged in 35.88 g of toluene. As the ligand, 0.0573 g of ligand (1) was used in the catalyst mixture solution. 0.0306 g of the compound (Ib) was added as the organic amine, and 0.4235 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 29.7 mol % n-pentanal and 1.9 mol % 2-methylbutanal (butenes conversion 85.3 mol %, regioselectivity for n-pentanal 94.0%).

Example 10

In a 100 ml autoclave from Parr Instruments, 5.0 g of n-octene were hydroformylated at 120° C. and 20 bar. As the precursor, 0.0049 g of Rh(acac)(CO)$_2$ was initially charged in 41.29 g of toluene. As the ligand, 0.0669 g of ligand (1) was used in the catalyst mixture solution. 0.0378 g of the compound (Ib) was added as the organic amine, and 0.5030 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 54.2 mol % aldehydes (regioselectivity for n-nonanal 90.9%). As hydrogenation products, 3.9 mol % n-octane and 3.2% nonanol were found in the output.

Example 11

In a 100 ml autoclave from Parr Instruments, 7.0 g of 1,3-butadiene were hydroformylated at 120° C. and 20 bar. As the precursor, 0.0054 g of Rh(acac)(CO)$_2$ was initially charged in 46.82 g of toluene. As the ligand, 0.0770 g of ligand (1) was used in the catalyst mixture solution. 0.0413 g of the compound (Ib) was added as the organic amine, and 0.5599 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The output comprises 0.2 mol % n-butane, 11.3% n-butenes, 12.9% aldehydes and 11.5 mol % 4-vinylcyclohexene. The total conversion of 1,3-butadiene is 37.2%.

Example 12

In a 100 ml autoclave from Parr Instruments, 5.6 g of methyl oleate were hydroformylated at 120° C. and 20 bar. As the precursor, 0.0052 g of Rh(acac)(CO)$_2$ was initially charged in 44.06 g of toluene. As the ligand, 0.0689 g of ligand (1) was used in the catalyst mixture solution. 0.0375 g of the compound (Ib) was added as the organic amine, and 0.5260 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. From $^1$H and $^{13}$C NMR spectra, an aldehyde yield of 49.5 mol % was calculated. The regioselectivity for terminal aldehydes is 20.6 mol %. The double bond content is 35.9 mol %.

Example 13

In a 100 ml autoclave from Parr Instruments, 6.9 g of a hydrocarbon mixture from catalytically operated cracking plants having the following composition: 1.5 mol % propane, 0.8 mol % propene, 28.1 mol % isobutane, 8.1 mol % n-butane, 16.4 mol % 1-butene, 16.9 mol % isobutene, 28.2 mol % 2-butenes, 0.5 mol % 1,3-butadiene and fractions of C5 olefins and hydrocarbons were hydroformylated at 120° C. and 20 bar. As the precursor, 0.0048 g of Rh(acac)(CO)$_2$ was initially charged in 43.39 g of toluene. As the ligand, 0.0672 g of ligand (1) was used in the catalyst mixture solution. 0.0359 g of the compound (Ib) was added as the organic amine, and 0.5035 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours.

The output comprises 1.3 mol % propane, 0.7 mol % butanal, 27.5 mol % isobutane, 9.6 mol % n-butane, 13.1 mol % 3-methylbutanal (77.4% isobutene conversion), 39.1 mol % pentanal, 2.1 mol % 2-methylbutanal (n-butenes conversion 96.9%, regioselectivity for n-pentanal 95.0%).

Example 14

In a 100 ml autoclave from Parr Instruments, 1.8 g of ethene were hydroformylated at 120° C. and 50 bar. As the precursor, 0.0050 g of Rh(acac)(CO)$_2$ was initially charged in 42.68 g of toluene. As the ligand, 0.0668 g of ligand (1) was used in the catalyst mixture solution. 0.0363 g of the compound (Ib) was added as the organic amine, and 0.5095 g of TIPB as the GC standard. The reactant was metered in after attainment of the reaction temperature envisaged. During the reaction, the pressure was kept constant via synthesis gas regulation with a mass flow meter. Samples were taken from the reaction mixture after 20 hours. The conversion to propanal is 98.7%.

Comparative Experiment

Unsymmetric and Symmetric Ligands

As well as the testing of the inventive unsymmetric ligand (1) with various substrates, symmetric ligands and the corresponding unsymmetric isomer thereof were additionally tested under comparable conditions.

First of all, the symmetric biphephos ligand already mentioned in the prior art and the unsymmetric isomer thereof (9) were tested. The compound (9) was prepared analogously to the synthesis method in WO 95/28228 on page 19.

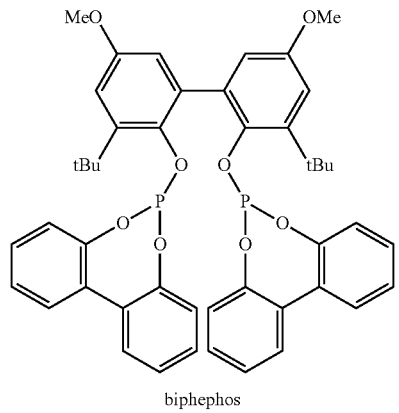

biphephos

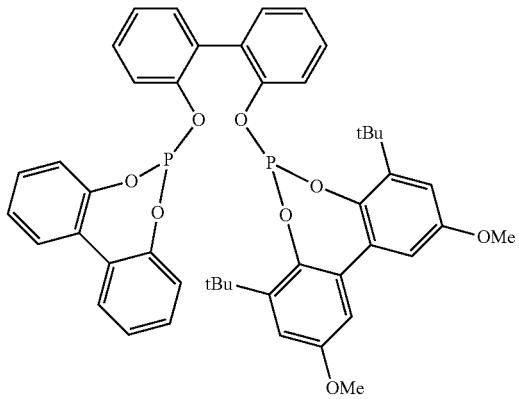

(9)

The experiments were conducted by the following method:

Example 15

In a 100 ml autoclave from Parr Instruments, 5.7 g of cis-2-butene were hydroformylated at 120° C. and 20 bar. As the precursor, 0.0054 g of Rh(acac)(CO)$_2$ was initially charged in 51.5 g of Diphyl (mixture of about 73.5% diphenyl oxide and 26.5% diphenyl). As the ligand, 0.0779 g of the appropriate ligand in the catalyst mixture solution was used. 0.0416 g of the compound (Ib) was added as the organic amine, and 0.5760 g of TIPB as the GC standard. The reactant was metered in after attainment of the reaction temperature envisaged.

During the reaction, the pressure was kept constant via synthesis gas regulation with a mass flow meter. Samples were taken from the reaction mixture after 12 hours.

The results are shown in Table 3.

TABLE 3

| Entry | Ligand | Yield of aldehydes | Regioselectivity n-pentanal in % |
|---|---|---|---|
| 1 | biphephos | 95.0 | 94.5 |
| 2 | (9) | 66.6 | 78.5 |

The unsymmetric isomer (ligand 9; entry 2) of the symmetric biphephos thus features a much lower activity and a much poorer selectivity than the symmetric biphephos ligand. This corresponds to the prior art. The use of the two ligands, i.e. of the symmetric biphephos ligand and the unsymmetric isomer thereof, has already been described in Rhodium-catalyzed Hydroformylation, ed. by P. W. N. M. van Leeuwen and C. Claver, Kluwer Academic Publishers 2006, A A Dordrecht, NL. On pages 45-46, Table 2, the hydroformylation results for the two ligands under comparable conditions are shown. In this context, it is clearly apparent that the symmetric biphephos ligand (in the reference ligand 5a) features a much higher n/i selectivity and a higher activity than its unsymmetric isomer (in the reference ligand 7). In the hydroformylation reaction of propene, the symmetric ligand has an n/i selectivity of 53 and a reaction rate of 402, whereas the unsymmetric ligand has only an n/i selectivity of 1.2 and a reaction rate of 280. This was confirmed once again by our own results in Table 3.

In addition, the inventive ligand (1) and the symmetric isomer thereof (10) were tested under comparable conditions. The experiments which follow were conducted by the method in Example 2. Only the ligands have been changed. Table 4 shows the results of hydroformylation of cis-2-butene with the inventive ligand (1) and the symmetric isomer thereof, ligand (9).

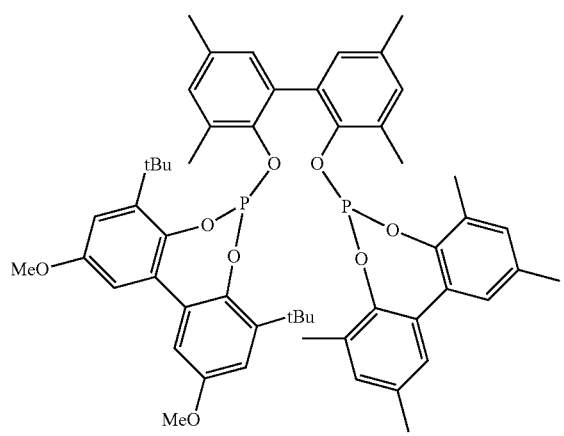

(1)

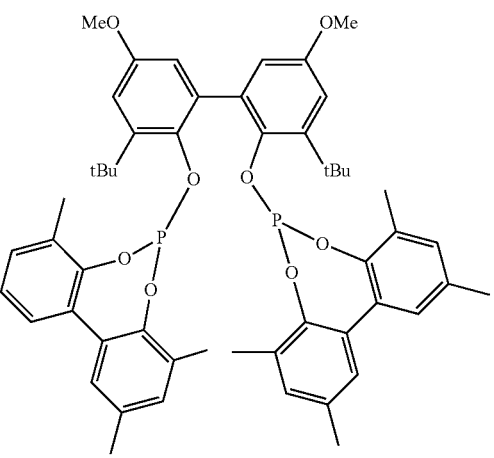

(10)

TABLE 4

| Entry | Ligand | mol % pentanal | mol % 2-methylbutanal | Regioselectivity n-pentanal in % |
|---|---|---|---|---|
| 1 | (1) | 80.0 | 5.2 | 94.0 |
| 2 | (10) | 59.9 | 6.35 | 90.4 |

The inventive unsymmetric ligand (1) (entry 1) has very good n-pentanal regioselectivity of 94% and good aldehyde yields. The symmetric isomer thereof (entry 2), in contrast, has poorer pentanal selectivities of only 90% and much poorer activities, i.e. yields.

This result is surprising since unsymmetric substituted bisphosphites show distinct losses in activity and selectivity compared to symmetrically substituted examples, as described in the prior art and confirmed by the above comparative experiments with the biphephos ligand and the unsymmetric isomer thereof (9). Thus, the inventive unsymmetric ligand (1), in complete contrast to the prior art, features very good selectivities and activities. In addition, the inventive ligand (1) is a ligand of very prolonged stability, as shown in the extended experiment in a continuously operated plant which follows.

Comparative Experiment

Extended Experiment

In a first experiment series, the inventive compound (1) was tested. In the second experiment series, the comparative compound biphephos was used under the same experimental conditions.

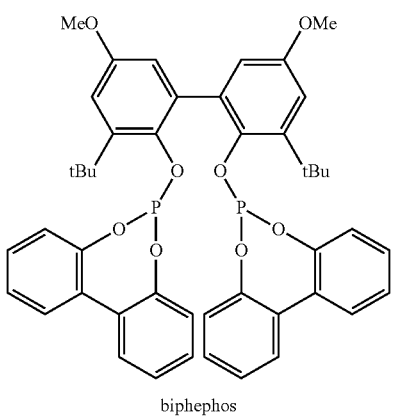

biphephos

A hydroformylation of butene/butane mixtures was performed in a continuously operated experiment system.

This experiment system consisted essentially of a pressure reactor of capacity 20 liters with a downstream condenser and phase separation vessel (gas/liquid) for the gas phase originating from the reactor, and a cycle gas compressor which returns the gas phase from the phase separation vessel back down into the reaction zone. A portion of this cycle gas is run out of the reaction system as offgas after the phase separation.

In order to achieve optimal gas distribution in the reactor system, a gas distributor ring with bores was installed here.

By means of installed heating and cooling apparatuses, the temperature of the reactor could be controlled.

Prior to the hydroformylation, the reactor system was purged with nitrogen to free it of oxygen. Subsequently, the reactor was charged with 12 liters of catalyst solution. This catalyst solution was composed of 12 kg of isononyl benzoate, 4.5 g of Rh(acac)(CO)$_2$, 63 g of bisphosphite ligand (1), 200 g of amine IIb, and was mixed beforehand in a vessel. The isononyl benzoate was stripped beforehand with nitrogen, in order to remove oxygen and water from the solvent.

Subsequently, the reactor system was purged with synthesis gas to free it of nitrogen. Once the nitrogen content had fallen <10% by volume, the reactor system was pressurized to 1.0 MPa with synthesis gas and then heated to 120° C.

On attainment of the operating temperature, the reactor system was brought to reaction pressure 1.7 MPa with synthesis gas.

Thereafter, the addition of the starting materials was commenced. The crude butane was run through a vaporizer in order to run the crude butane into the cycle gas in gaseous form.

The following throughputs were set:

0.3 kg/h of crude butane (a mixture of 35% 2-butenes and n-butane and 1-butene concentrations of about 1%), 75 l (STP)/h of synthesis gas (50% by vol. of H2 and 50% by vol. of CO).

For the daily metered addition of the compound (1) and amine IIb, a 1.4% solution of the bisphosphite ligand I in n-pentanal, which had been freed of residual C4 hydrocarbons (<3%) beforehand by stripping with nitrogen, was made up. The amine IIb was used in a threefold molar excess relative to the compound (1). For better stabilization of this solution, the amine IIb was added to the solution before the bisphosphite ligand (1).

The reaction products were removed continuously from the reactor via the cycle gas stream and partially condensed out in a condenser at 50° C. The condensed phase was run continuously out of the phase separation vessel. To determine the yield, samples were taken from the cycle gas upstream and downstream of the reactor and analysed by means of a gas chromatograph.

By a daily metered addition of the above-described ligand solution, it was possible to keep the conversion and regioselectivity constant.

To determine the reactor contents, samples were taken from the reactor and analysed by means of liquid chromatography (HPLC).

Under the selected reaction conditions, an aldehyde yield between 80% and 90% was established. It was possible to keep this state constant up to the end of the experiment. The percentage distribution between n-pentanal and 2-methylbutanal, i.e. the regioselectivity, was 92% to 8%.

In the steady-state phase of the experiment, no rhodium degradation was recorded.

The results are shown in FIG. 3.

FIG. 3 shows a 1500 h prolonged experiment in the hydroformylation of crude butane with the inventive unsymmetric ligand (1). Over the entire experiment duration, a constantly high activity, i.e. aldehyde yield averaging 80%, was ensured, still with very good regioselectivity.

In the second experiment series, rather than the inventive compound (1), 55 g of the comparative biphephos compound were used. The results are shown in FIG. 4.

Under the reaction conditions selected, the aldehyde yield fell from initially 70% to 80% after 150 h to 40% to 50%. The percentage distribution between n-pentanal and 2-methylbutanal, i.e. the regioselectivity, was 95% to 5%.

In the steady-state phase of the experiment, no rhodium degradation was recorded.

FIG. 4 shows a 250 h prolonged experiment in the hydroformylation of crude butane with the symmetric comparative biphephos ligand (1). In this case, compared to the inventive ligand, long-lasting activity cannot be ensured. Under the reaction conditions selected, the aldehyde yield fell from initially 70% to 80% after 150 h to 40% to 50%. The regioselectivity was still very good. In other word, this ligand features much lower long-term stability.

Consequently, the inventive unsymmetric ligand (1) features much better stability than the symmetric comparative biphephos ligand.

The inventive ligand (1) in the catalytically active composition features much better long-term stability than the ligands described in the prior art to date and thus achieves the stated object. An optimal long-term stability of the catalytically active composition is of significance especially in industrial scale use, since the ligand in the hydroformylation reaction can be replenished on the industrial scale, but any replenishment adversely affects the economic viability of an industrial scale process and may make it unfeasible. It is thus essential to use a ligand of maximum long-term stability, which, as well as the long-term stability, also features good activity and good n/i selectivity. This object is achieved by the inventive ligand (1).

The invention claimed is:

1. A compound of formula (1):

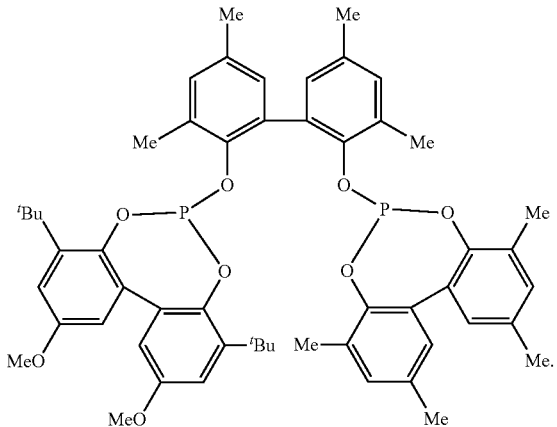

(1)

2. A process for preparing a compound of claim 1, comprising:
   i) oxidatively coupling 2,4-dimethylphenol to obtain 3,3', 5,5'-tetramethyl-2,2'-dihydroxybiphenyl;

ii) oxidatively coupling 3-tert-butyl-4-hydroxyanisole to obtain 5,5'-dimethoxy-3,3'-di-tert-butyl-2,2'-dihydroxybiphenyl;

iii) reacting 3,3',5,5'-tetramethyl-2,2'-dihydroxybiphenyl from i) with $PCl_3$ to obtain a phosphorochloridite derivative under inert gas atmosphere;

iv) reacting at least 2 equivalents of the phosphorochloridite derivative from iii) with 1 equivalent of the 5,5'-dimethoxy-3,3'-di-tert-butyl-2,2'-dihydroxybiphenyl from ii) under inert gas atmosphere.

3. The process according to claim 2,
wherein a solvent mixture is present during the reacting iv).

4. The process according to claim 3, wherein the solvent mixture comprises at least two solvents selected from the group consisting of an organic nitrogen compound, an organic ester, and an aromatic compound.

5. The process according to claim 4,
wherein the organic nitrogen compound is at least one compound selected from the group consisting of a nitrile, an amine, and an amide.

6. The process according to claim 2,
further comprising v), removing the compound (1) in solid form and suspending the compound (1) in an aprotic solvent mixture, recrystallizing the compound (1) in an aprotic solvent mixture, or suspending and recrystallizing the compound in an aprotic solvent mixture.

7. A compound of formula (2):

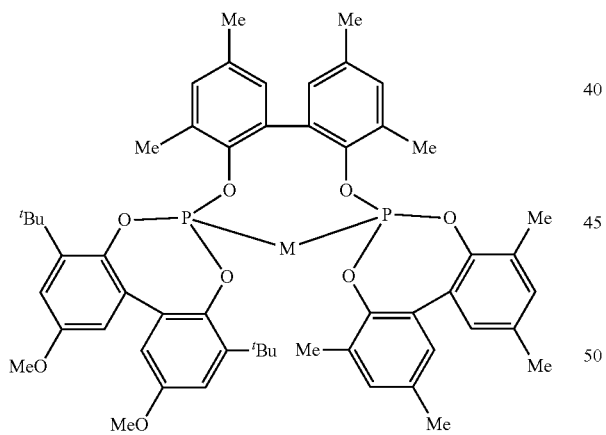

(2)

wherein M is selected from the group consisting of Fe, Ru, Os, Co, Rh, Ir, Ni, Pd, Pt, and M may enter into additional bonds.

8. A compound of the formula (3):

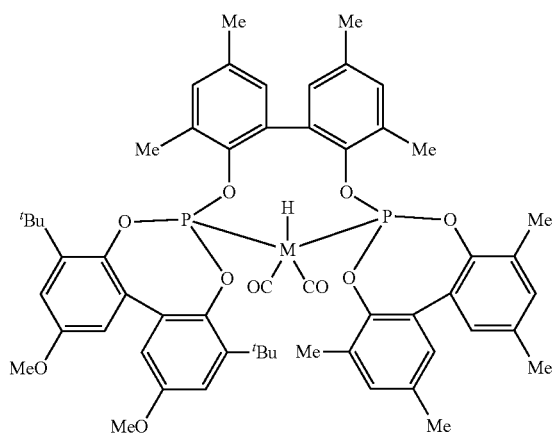

(3)

wherein M is selected from the group consisting of Fe, Ru, Os, Co, Rh, Ir, Ni, Pd, and Pt.

9. The compound according to claim 8, wherein M is Rh.

10. A mixture comprising a compound of formula (2) and/or (3), and a compound of formula (1) not bonded to M.

11. A composition comprising a mixture of claim 10,
and a further component selected from the group consisting of bases, organic amines, buffer solutions, epoxides, and ion exchangers.

12. The composition according to claim 11, wherein the organic amine has an 2,2,6,6-tetramethylpiperidine unit.

13. The composition according to claim 11, wherein the further component is a di-4-(2,2,6,6-tetramethylpiperidinyl) sebacate.

14. A process for hydroformylating an unsaturated compound or a mixture of unsaturated compounds, comprising:
a) initially charging a compound of claim 1,
b) introducing a gas mixture comprising carbon monoxide and hydrogen; and
c) adding an unsaturated compound or a mixture of unsaturated compounds.

15. The process according to claim 14,
wherein the unsaturated compound or mixture thereof are selected from the group consisting of:
hydrocarbon mixtures from steamcracking plants;
hydrocarbon mixtures from catalytically operated cracking plants;
hydrocarbon mixtures from oligomerization operations;
hydrocarbon mixtures comprising polyunsaturated compounds; and
unsaturated carboxylic acid derivatives.

16. The process according to claim 14,
wherein the mixture comprises unsaturated compounds having 2 to 30 carbon atoms.

17. The process according to claim 14,
wherein the mixture comprises unsaturated compounds having 2 to 8 carbon atoms.

18. The process according to claim 15,
wherein the unsaturated carboxylic acid derivatives are selected from fatty acid esters.

* * * * *